US012203134B2

(12) United States Patent
Nagendran et al.

(10) Patent No.: US 12,203,134 B2
(45) Date of Patent: *Jan. 21, 2025

(54) METHODS OF MEASURING MISLOCALIZATION OF AN ANALYTE

(71) Applicant: 10x Genomics, Inc., Pleasanton, CA (US)

(72) Inventors: Monica Nagendran, Pleasanton, CA (US); Jonathan Cheng, Pleasanton, CA (US); Eswar Prasad Ramachandran Iyer, Oakland, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/087,440

(22) Filed: Dec. 22, 2022

(65) Prior Publication Data

US 2023/0126825 A1 Apr. 27, 2023

Related U.S. Application Data

(63) Continuation of application No. PCT/US2022/024646, filed on Apr. 13, 2022.

(60) Provisional application No. 63/174,789, filed on Apr. 14, 2021.

(51) Int. Cl.
C12Q 1/68 (2018.01)
C12Q 1/6841 (2018.01)
C12Q 1/6806 (2018.01)
C12Q 1/6844 (2018.01)

(52) U.S. Cl.
CPC ......... *C12Q 1/6841* (2013.01); *C12Q 1/6806* (2013.01); *C12Q 1/6844* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,928,906 A | 7/1999 | Koester et al. |
| 5,958,775 A | 9/1999 | Wickstrrom |
| 5,962,272 A | 10/1999 | Chenchik et al. |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,266,459 B1 | 7/2001 | Walt |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Marx, "Method of the Year: spatially resolved transcriptomics," Nature Methods, 2021, 18(1):9-14.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
U.S. Appl. No. 16/353,937, filed Mar. 14, 2019, Frisen et al.
U.S. Appl. No. 17/707,189, filed Mar. 29, 2022, Chell et al.
U.S. Appl. No. 63/033,348, filed Jun. 2, 2020, Bent.
[No Author Listed], "Chromium Next GEM Single Cell 3' Reagent Kits v3.1—User Guide," 10x Genomics, Document No. CG000204, Nov. 2019, 58 pages.

(Continued)

*Primary Examiner* — Suryaprabha Chunduru
(74) *Attorney, Agent, or Firm* — Fish & Richardson P.C.

(57) ABSTRACT

Provided herein are methods for determining the mislocalization of an analyte by capturing the analyte on an array and measuring the mislocalization distance.

30 Claims, 19 Drawing Sheets

(56) References Cited

U.S. PATENT DOCUMENTS

| | | |
|---|---|---|
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |

(56) References Cited

U.S. PATENT DOCUMENTS

| | | |
|---|---|---|
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,227,639 B2 | 3/2019 | Levner et al. |
| 10,273,541 B2 | 4/2019 | Hindson et al. |
| 10,308,982 B2 | 6/2019 | Chee |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,501,440 B2 | 11/2022 | Weisenfeld et al. |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,519,138 B2 | 12/2022 | Meier et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 11,845,979 B2 | 12/2023 | Engblom et al. |
| 11,859,178 B2 | 1/2024 | Gallant et al. |
| 11,866,767 B2 | 1/2024 | Uytingco et al. |
| 11,866,770 B2 | 1/2024 | Chee |
| 11,873,482 B2 | 1/2024 | Kim et al. |
| 11,891,654 B2 | 2/2024 | Alvarado Martinez et al. |

(56) References Cited

U.S. PATENT DOCUMENTS

| | | |
|---|---|---|
| 11,898,205 B2 | 2/2024 | Bava |
| 11,926,822 B1 | 3/2024 | Gohil et al. |
| 11,926,863 B1 | 3/2024 | Boutet |
| 11,926,867 B2 | 3/2024 | Yin et al. |
| 11,933,957 B1 | 3/2024 | Tentori et al. |
| 11,952,627 B2 | 4/2024 | Stoeckius |
| 11,959,076 B2 | 4/2024 | Kim et al. |
| 11,959,130 B2 | 4/2024 | Galonska et al. |
| 11,965,213 B2 | 4/2024 | Williams |
| 11,970,739 B2 | 4/2024 | Chew et al. |
| 11,981,958 B1 | 5/2024 | Galonska |
| 11,981,960 B1 | 5/2024 | Lin et al. |
| 11,981,965 B2 | 5/2024 | Chell et al. |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0092624 A1 | 5/2003 | Wang et al. |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0170373 A1 | 8/2005 | Monforte |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0260653 A1 | 11/2005 | LaBaer |
| 2005/0266417 A1 | 12/2005 | Barany et al. |
| 2006/0041385 A1* | 2/2006 | Bauer ............... G01N 21/27 702/19 |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0270273 A1 | 10/2009 | Burns et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Fan et al. |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0023433 A1 | 1/2013 | Luo et al. |

(56) References Cited

U.S. PATENT DOCUMENTS

| | | |
|---|---|---|
| 2013/0035239 A1 | 2/2013 | Kong et al. |
| 2013/0040842 A1 | 2/2013 | Lim et al. |
| 2013/0065768 A1 | 3/2013 | Zheng et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378350 A1 | 12/2014 | Hindson et al. |
| 2015/0000854 A1 | 1/2015 | Gann-Fetter et al. |
| 2015/0292988 A1 | 10/2015 | Bharadwaj et al. |
| 2015/0344942 A1 | 12/2015 | Frisen et al. |
| 2016/0019337 A1 | 1/2016 | Roberts et al. |
| 2016/0024576 A1 | 1/2016 | Chee |
| 2016/0041159 A1 | 2/2016 | Labaer et al. |
| 2016/0060687 A1 | 3/2016 | Zhu et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0201125 A1 | 7/2016 | Samuels et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0283860 A1 | 4/2017 | Kool et al. |
| 2017/0159109 A1 | 6/2017 | Zheng et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0080019 A1 | 3/2018 | Blainey et al. |
| 2018/0094316 A1 | 4/2018 | Oliphant et al. |
| 2018/0112261 A1 | 4/2018 | Van Driel et al. |
| 2018/0127817 A1 | 5/2018 | Borchert et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2018/0334670 A1 | 11/2018 | Bharadwaj et al. |
| 2019/0055594 A1 | 2/2019 | Samusik et al. |
| 2019/0064173 A1 | 2/2019 | Bharadwaj et al. |
| 2019/0071656 A1 | 3/2019 | Chang et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0360034 A1 | 11/2019 | Zhou et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0053655 A1 | 2/2020 | Ghosh et al. |
| 2020/0061064 A1 | 2/2020 | Maciejewski et al. |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0130881 A1 | 5/2021 | Cox |
| 2021/0140982 A1 | 5/2021 | Uytingco et al. |

(56) References Cited

U.S. PATENT DOCUMENTS

| | | |
|---|---|---|
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1 | 7/2022 | Ach et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0017773 A1 | 1/2023 | Kim et al. |
| 2023/0416807 A1 | 1/2023 | Chee |
| 2023/0416808 A1 | 1/2023 | Sukovich et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304072 A1 | 9/2023 | Gohil et al. |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |

(56) References Cited

U.S. PATENT DOCUMENTS

| | | |
|---|---|---|
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0018589 A1 | 1/2024 | Schnall-Levin |
| 2024/0026445 A1 | 1/2024 | Ramachandran Iyer et al. |
| 2024/0033743 A1 | 2/2024 | Tentori et al. |
| 2024/0035937 A1 | 2/2024 | Cox et al. |
| 2024/0043908 A1 | 2/2024 | Chew et al. |
| 2024/0043925 A1 | 2/2024 | Bent et al. |
| 2024/0052343 A1 | 2/2024 | Gallant et al. |
| 2024/0053351 A1* | 2/2024 | Uytingco ............. G01N 33/582 |
| 2024/0060115 A1 | 2/2024 | Chee et al. |
| 2024/0067953 A1 | 2/2024 | Mikkelsen et al. |
| 2024/0068016 A1 | 2/2024 | Frisen et al. |
| 2024/0068017 A1 | 2/2024 | Lundeberg et al. |
| 2024/0076723 A1 | 3/2024 | Mignardi |
| 2024/0080346 A1 | 3/2024 | Engblom et al. |
| 2024/0084365 A1 | 3/2024 | Frisen et al. |
| 2024/0084366 A1 | 3/2024 | Chee |
| 2024/0084383 A1 | 3/2024 | Ramachandran Iyer et al. |
| 2024/0093274 A1 | 3/2024 | Frisen et al. |
| 2024/0093290 A1 | 3/2024 | Stahl et al. |
| 2024/0110228 A1 | 4/2024 | Uytingco et al. |
| 2024/0124933 A1 | 4/2024 | Chell et al. |
| 2024/0125772 A1 | 4/2024 | Delaney et al. |
| 2024/0141327 A1 | 5/2024 | Kim et al. |
| 2024/0158838 A1 | 5/2024 | Alvarado Martinez et al. |
| 2024/0175080 A1 | 5/2024 | Galonska et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 1929039 | 6/2008 |
| EP | 2002017 | 12/2008 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/093098 | 8/2008 |
| WO | WO 2009/032167 | 3/2009 |
| WO | WO 2009/036525 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2010/127186 | 11/2010 |
| WO | WO 2011/008502 | 1/2011 |
| WO | WO 2011/062933 | 5/2011 |
| WO | WO 2011/068088 | 6/2011 |
| WO | WO 2011/127006 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/210223 | 12/2014 |
| WO | WO 2014/210353 | 12/2014 |
| WO | WO 2015/031691 | 3/2015 |

(56) References Cited

FOREIGN PATENT DOCUMENTS

| | | |
|---|---|---|
| WO | WO 2015/069374 | 5/2015 |
| WO | WO 2015/161173 | 10/2015 |
| WO | WO 2016/077763 | 5/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/075293 | 5/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO-2018175779 A1 * | 9/2018 ............ C12N 15/11 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO-2020028194 A1 * | 2/2020 ........... C12Q 1/6806 |
| WO | WO 2020/047002 | 3/2020 |
| WO | WO 2020/047005 | 3/2020 |
| WO | WO 2020/047010 | 3/2020 |
| WO | WO 2020/056381 | 3/2020 |
| WO | WO 2020/061066 | 3/2020 |
| WO | WO 2020/061108 | 3/2020 |
| WO | WO-2020047005 A1 * | 3/2020 ........... C12Q 1/6841 |
| WO | WO-2020047007 A2 * | 3/2020 ........... C12Q 1/6837 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/015913 | 11/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |

OTHER PUBLICATIONS

[No Author Listed], "Chromium Next GEM Single Cell 3' Reagent Kits v3.1 (Dual Index)—User Guide," 10x Genomics, Mar. 2021, Document No. CG000315, 61 pages.

(56) References Cited

OTHER PUBLICATIONS

[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal G·T Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Helicase-dependent amplification: use in OnChip amplification and potential for point-of-care diagnostics," Expert Rev Mol Diagn., Oct. 2009, 9(7):645-650.
Appella, "Non-natural nucleic acids for synthetic biology," Current Opinion in Chemical Biology, Dec. 2009, 13(5-6): 687-696.

Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al, "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asp et al., "Spatially Resolved Transcriptomes—Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, p. 6.1-6.8.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).

(56) References Cited

OTHER PUBLICATIONS

Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Bunt et al., "FRET from single to multiplexed signaling events," Biophys Rev. Apr. 2017, 9(2): 119-129.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Caliari et al., "A practical guide to hydrogels for cell culture," Nat Methods., Apr. 2016, 13(5):405-14.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.
Chen et al., "Efficient in situ barcode sequencing using padlock probe-based BaristaSeq," Nucleic Acids Res., 2018, 46(4): e22, 11 pages.
Chen et al., "Expansion microscopy," Science, 2015, 347(6221):543-548.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "µCB-seq: microfluidic cell barcoding and sequencing for high-resolution imaging and sequencing of single cells," Lab Chip, Nov. 2020, 20(21):3899-3913.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Codeluppi et al., "Spatial organization of the somatosensory cortex revealed by osmFISH," Nature Methods, Nov. 2018, 15:932-935.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.

(56) References Cited

OTHER PUBLICATIONS

Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Evers et al., "The effect of formaldehyde fixation on RNA: optimization of formaldehyde adduct removal," J Mol Diagn., May 2011, 13(3):282-8.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2): 186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 DNA ligase," Nucleic Acids Res., Jun. 2017, 45(10):e79, 10 pages.
Gao et al., "A highly homogeneous expansion microscopy polymer composed of tetrahedron-like monomers," bioRxiv, Oct. 22, 2019, 23 pages (Preprint).
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, p. 38 pages.
Grokhovsky, "Specificity of DNA cleavage by ultrasound," Molecular Biology, 2006, 40(2):276-283.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.

(56) References Cited

OTHER PUBLICATIONS

Hoffman et al., "Formaldehyde crosslinking: a tool for the study of chromatin complexes," J Biol Chem., Oct. 2015, 290(44):26404-11.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of Mycobacterium avium: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Kozlov et al., "A highly scalable peptide-based assay system for proteomics," PLoS One, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.

(56) References Cited

OTHER PUBLICATIONS

Lou et al., "A review of room temperature storage of biospecimen tissue and nucleic acids for anatomic pathology laboratories and biorepositories," Clin Biochem., Mar. 2014, 47(4-5):267-73.

Lovatt et al., "Transcriptome in vivo analysis (TIVA) of spatially defined single cells in live tissue," Nature Methods, 2013, 11(2):190-196.

Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.

Lundberg et al., "High-fidelity amplification using a thermostable DNA polymerase isolated from Pyrococcus furiosus," Gene, 1991, 108(1):1-6.

Lundberg et al., "Homogeneous antibody-based proximity extension assays provide sensitive and specific detection of low-abundant proteins in human blood," Nucleic Acids Res., 2011, 39(15):e102, 8 pages.

Lundberg et al., "Multiplexed homogeneous proximity ligation assays for high-throughput protein biomarker research in serological material," Mol Cell Proteomics, 2011, 10(4):M110.004978, 11 pages.

Lundin et al., "Increased throughput by parallelization of library preparation for massive sequencing," PLoS One, Apr. 2010, 5(4):e10029, 7 pages.

Lyamichev et al., "Invader assay for SNP genotyping," Methods Mol Biol., 2003, 212:229-40.

Lyamichev et al., "Polymorphism identification and quantitative detection of genomic DNA by invasive cleavage of oligonucleotide probes," Nat Biotechnol., Mar. 1999, 17(3):292-6.

Lyck et al., "Immunohistochemical markers for quantitative studies of neurons and glia in human neocortex," J Histochem Cytochem, 2008, 56(3):201-21.

Lykidis et al., "Novel zinc-based fixative for high quality DNA, RNA and protein analysis," Nucleic Acids Res., Jun. 2007, 35(12):e85, 10 pages.

Ma et al., "Isothermal amplification method for next-generation sequencing," PNAS, Aug. 12, 2013, 110(35):14320-14323.

MacBeath et al., "Printing proteins as microarrays for high-throughput function determination," Science, Sep. 2000, 289(5485):1760-1763.

MacIntyre, "Unmasking antigens for immunohistochemistry.," Br J Biomed Sci., 2001, 58(3):190-6.

Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.

McCloskey et al., "Encoding PCR products with batch-stamps and barcodes," Biochem. Genet., 2007, 45(11-12):761-767.

Meers et al., "Improved CUT&RUN chromatin profiling tools," Elife, Jun. 2019, 8:e46314, 16 pages.

Merritt et al., "Multiplex digital spatial profiling of proteins and RNA in fixed tissue," Nat Biotechnol, May 2020, 38(5):586-599.

Metzker, "Sequencing technologies—the next generation," Nature Reviews Genetics, 2010, 11(1):31-46.

Miele et al., "Mapping cis- and trans-chromatin interaction networks using chromosome conformation capture (3C)," Methods Mol Biol., 2009, 464:105-21.

Mignardi et al., "Oligonucleotide gap-fill ligation for mutation detection and sequencing in situ," Nucleic Acids Research, Aug. 3, 2015, 43(22):e151, 12 pages.

Miller et al., "Basic concepts of microarrays and potential applications in clinical microbiology," Clinical Microbiology Reviews, 2009, 22(4):611-633.

Miller et al., "Chapter 11—Solid and Suspension Microarrays for Microbial Diagnostics," Methods in Microbiology, 2015, 42:395-431.

Miner et al., "Molecular barcodes detect redundancy and contamination in hairpin-bisulfite PCR," Nucleic Acids Res., Sep. 2004, 32(17):e135, 4 pages.

Mishra et al., "Three-dimensional genome architecture and emerging technologies: looping in disease," Genome Medicine, 2017, 9(1):87, 14 pages.

Mitra et al., "Digital genotyping and haplotyping with polymerase colonies," Proc. Natl. Acad. Sci. USA, May 2003, 100(10):5926-5931.

Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.

Mizusawa et al., "A bacteriophage lambda vector for cloning with BamHI and Sau3A," Gene, 1982, 20(3):317-322.

Mohsen et al., "The Discovery of Rolling Circle Amplification and Rolling Circle Transcription," Acc Chem Res., Nov. 15, 2016, 49(11):2540-2550, 25 pages.

Morlan et al., "Selective depletion of rRNA enables whole transcriptome profiling of archival fixed tissue," PLoS One, Aug. 2012, 7(8):e42882, 8 pages.

Motea et al., "Terminal deoxynucleotidyl transferase: the story of a misguided DNA polymerase," Biochim Biophys Acta., May 2010, 1804(5):1151-66.

Mulder et al., "CapTCR-seq: hybrid capture for T-cell receptor repertoire profiling," Blood Advances, Dec. 2018, 2(23):3506-3514.

Nadji et al., "Immunohistochemistry of tissue prepared by a molecular-friendly fixation and processing system," Appl Immunohistochem Mol Morphol., Sep. 2005, 13(3):277-82.

Nallur et al., "Signal amplification by rolling circle amplification on DNA microarrays," Nucleic Acids Res., Dec. 1, 2001, 29(23):e118, 9 pages.

Nandakumar et al., "How an RNA Ligase Discriminates RNA versus DNA Damage," Molecular Cell, 2004, 16:211-221.

Nandakumar et al., "RNA Substrate Specificity and Structure-guided Mutational Analysis of Bacteriophage T4 RNA Ligase 2," Journal of Biological Chemistry, Jul. 2004, 279(30):31337-31347.

Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.

Ng et al., "Gene identification signature (GIS) analysis for transcriptome characterization and genome annotation," Nature Methods, 2005, 2(2):105-111.

Nichols et al., "RNA Ligases," Curr Protoc Mol Biol., Oct. 2008, 84(1):3.15.1-3.15.4.

Niedringhaus et al., "Landscape of next-generation sequencing technologies," Anal Chem., Jun. 2011, 83(12):4327-41.

Nikiforov et al., "The use of 96-well polystyrene plates for DNA hybridization-based assays: an evaluation of different approaches to oligonucleotide immobilization," Anal Biochem, May 1995, 227(1):201-9.

Niklas et al., "Selective permeabilization for the high-throughput measurement of compartmented enzyme activities in mammalian cells," Anal Biochem, Sep. 2011, 416(2):218-27.

Nilsson et al., "RNA-templated DNA ligation for transcript analysis," Nucleic Acids Res., Jan. 2001, 29(2):578-81.

Nowak et al., "Entering the Postgenome Era," Science, 1995, 270(5235):368-71.

Ohtsubo et al., "Bacterial insertion sequences," Curr Top Microbiol Immunol., 1996, 204:1-26.

Olivier, "The Invader assay for SNP genotyping," Mutat. Res., Jun. 2005, 573(1-2):103-110.

Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.

Ozsolak et al., "Digital transcriptome profiling from attomole-level RNA samples," Genome Res., Apr. 2010, 20(4):519-25.

Pandey et al., "Inhibition of terminal deoxynucleotidyl transferase by adenine dinucleotides. Unique inhibitory action of Ap5A," FEBS Lett., Mar. 1987, 213(1):204-8.

Park et al., "Single cell trapping in larger microwells capable of supporting cell spreading and proliferation," Microfluid Nanofluid, 2010, 8:263-268.

(56) References Cited

OTHER PUBLICATIONS

Passow et al., "RNAlater and flash freezing storage methods nonrandomly influence observed gene expression in RNAseq experiments," bioRxiv, Jul. 2018, 28 pages.
PCT International Preliminary Report on Patentability in International Appln. No. PCT/US2019/048425, dated Mar. 2, 2021, 9 pages.
PCT International Preliminary Report on Patentability in International Appln. No. PCT/US2019/048434, dated Mar. 2, 2021, 15 pages.
PCT International Search Report and Written Opinion in International Appln. No. PCT/US2020/066681, dated Apr. 14, 2021, 17 pages.
PCT International Search Report and Written Opinion in International Appln. No. PCT/US2021/012659, dated Apr. 16, 2021, 15 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gen," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLOS Biol., Jul. 2006, 4(7):e204, 7 pages.
Plasterk, "The Tcl/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.

Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res., Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.

(56) References Cited

OTHER PUBLICATIONS

Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Sutherland et al., "Utility of formaldehyde cross-linking and mass spectrometry in the study of protein-protein interactions," J. Mass Spectrom., Jun. 2008, 43(6):699-715.
Takei et al., "Integrated Spatial Genomics Reveals Global Architecture Of Single Nuclei," Nature, Jan. 27, 2021, 590(7845):344-350, 53 pages.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS One, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.

Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39): 19490-19499.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "A trichostatin A expression signature identified by TempO-Seq targeted whole transcriptome profiling," PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.

(56) References Cited

OTHER PUBLICATIONS

Yin et al., "Genetically encoded short peptide tag for versatile protein labeling by Sfp phosphopantetheinyl transferase," PNAS, 2005, 102(44):15815-20.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probest," Chem. Commun., 2013, 49:10013-10015.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Bibikova et al., "Quantitative gene expression profiling in formalin-fixed paraffin-embedded tissues using universal bead arrays," The American Journal of Pathology, Nov. 1, 2004, 165(5):1799-1807.
Choi et al., "Multiplexed detection of mRNA using porosity-tuned hydrogel microparticles," Analytical chemistry, Sep. 28, 2012, 84(21):9370-9378.
Fan et al., "A versatile assay for high-throughput gene expression profiling on universal array matrices," Genome Research, May 1, 2004, 14(5):878-885.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Sun et al., "Statistical Analysis of Spatial Expression Pattern for Spatially Resolved Transcriptomic Studies," Nature Methods, Jan. 27, 2020, 17(2): 193-200.
Svensson et al., "SpatialDE: identification of spatially variable genes," Nature Methods, May 2018, 15:343-346, 15 pages.
Chen et al. "Arrayed profiling of multiple glycans on whole living cell surfaces." Analytical chemistry, Oct. 15, 2013, 85(22):11153-11158.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Belton et al., "Hi-C: A comprehensive technique to capture the conformation of genomes," Methods, Nov. 2012, 58(3):268-276, 16 pages.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Fan et al., "Illumina Universal Bead Arrays," Methods in Enzymology, 2006, 410:57-73.
Hadrup et al., "Parallel detection of antigen-specific T-cell responses by multidimensional encoding of MHC multimers," Nat. Methods., Jul. 2009, 6(7), 520-526.
Hobro et al., "An evaluation of fixation methods: Spatial and compositional cellular changes observed by Raman imaging," Vibrational Spectroscopy, Jul. 2017, 91:31-45.
Howell et al., "iFRET: An Improved Fluorescence System for DNA-Melting Analysis," Genome Research, 2002, 12:1401-1407.
Landegren et al., "A Ligase-Mediated Gene Detection Technique," Science, 1988, 241(4869):1077-1080.
Mamedov et al., "Preparing unbiased T-cell receptor and antibody cDNA libraries for the deep next generation sequencing profiling," Frontiers in Immunol., Dec. 23, 2013, 4(456):1-10.
Nam et al., "Nanoparticle-Based Bio-Bar Codes for the Ultrasensitive Detection of Proteins," Science, Sep. 26, 2003, 301(5641):1884-1886.
Oksuz et al., "Systematic evaluation of chromosome conformation capture assays," Nature Methods, Sep. 2021, 18:1046-1055.
Redmond et al., "Single-cell TCRseq: paired recovery of entire T-cell alpha and beta chain transcripts in T-cell receptors from single-cell RNAseq," Genome Med, 2016, 8:80, 12 pages.
Rohland et al., "Partial uracil-DNA-glycosylase treatment for screening of ancient DNA," Phil. Trans. R. Soc. B, Jan. 19, 2015, 370(1660): 20130624, 11 pages.
Schmidl et al., "ChIPmentation: fast, robust, low-input ChIP-seq for histones and transcription factors," Nature Methods, Oct. 2015, 12:963-965.
Su et al., "Restriction enzyme selection dictates detection range sensitivity in chromatin conformation capture-based variant-to-gene mapping approaches," bioRxiv, Dec. 15, 2020, 22 pages.
PCT International Report on Patentability in International Appln. No. PCT/US2022/024646, dated Oct. 26, 2023, 7 pages.
10xGenomics.com, [online], "Visium Spatial Gene Expression Reagent Kits—Tissue Optimization—User Guide," Feb. 2022, retrieved on Mar. 29, 2024, retrieved from URL<https://cdn.10xgenomics.com/image/upload/v1660261286/support-documents/CG000238_VisiumSpatialTissueOptimizationUserGuide_RevE.pdf>, 46 pages.
Asp et al., "A spatiotemporal organ-wide gene expression and cell atlas of the developing human heart," Cell, Dec. 12, 2019, 179(7):1647-1660.
Kuhn et al., "A novel, high-performance random array platform for quantitative gene expression profiling," Genome Res, 2004, 14:2347-2356.

* cited by examiner

METHODS OF MEASURING MISLOCALIZATION OF AN ANALYTE

CROSS-REFERENCE TO RELATED APPLICATIONS

Pursuant to 35 U.S.C. § 119 (e), this application is a continuation of International Application PCT/US2022/024646, with an international filing date of Apr. 13, 2022, which claims the benefit of U.S. Provisional Patent Application No. 63/174,789, filed Apr. 14, 2021. The contents of these priority applications are incorporated herein by reference in their entireties.

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

Generally, spatial analysis requires determining the sequence of the analyte sequence or a complement thereof and the sequence of the spatial barcode or a complement thereof in order to identify the spatial location of the analyte in the original biological sample. Typically, this requires sequencing which can be time and resource intensive. Therefore, there is a need to assess analyte (biological sample) spatial preservation and presence prior to traditional spatial analysis.

SUMMARY

In one aspect, this disclosure features methods of determining analyte mislocalization within a biological sample, the method including: (a) obtaining a first image of the biological sample; (b) hybridizing the analyte to a capture probe on an array, wherein the array includes a plurality of capture probes, wherein a capture probe of the plurality of capture probe includes a capture domain; (c) extending the capture probe using the analyte as a template, thereby generating an extended capture probe; (d) hybridizing a padlock probe or a snail probe to the extended capture probe; (e) circularizing the padlock probe or the snail probe; (f) amplifying the padlock probe or the snail probe, thereby generating an amplified circularized padlock probe or an amplified circularized snail probe; (g) hybridizing a plurality of detection probes to the amplified circularized padlock probe or the amplified circularized snail probe, wherein a detection probe from the plurality of detection probes comprises: a sequence that is substantially complementary to a sequence of the padlock probe or the snail probe, or a complement thereof, and a detectable label; (h) obtaining a second image of the biological sample and detecting a signal from the plurality of detection probes in the second image; and (i) determining mislocalization of the analyte within the biological sample by comparing the first image of the biological sample to the second image of the biological sample.

Also provided herein is a method of determining mislocalization of an analyte within a biological sample, the method comprising: (a) obtaining a first image of the biological sample; (b) hybridizing an analyte derived molecule to a capture domain of a capture probe on an array, wherein the array comprises a plurality of capture probes, wherein the plurality of capture probes comprise a capture domain; (c) hybridizing a padlock probe or a snail probe to the analyte derived molecule; (d) circularizing the padlock probe or the snail probe; (e) amplifying the padlock probe or the snail probe, thereby generating an amplified circularized padlock probe or an amplified circularized snail probe; (f) hybridizing a plurality of detection probes to the amplified circularized padlock probe or the amplified circularized snail probe, wherein a detection probe from the plurality of detection probes comprises: a sequence that is substantially complementary to a sequence of the padlock probe or the snail probe, or a complement thereof, and a detectable label; (g) obtaining a second image of the biological sample and detecting a signal from the plurality of detection probes in the second image; and (h) determining mislocalization of the analyte within the biological sample by comparing the first image of the biological sample to the second image of the biological sample.

In some instances, the analyte derived molecule is a ligation product. In some instances, the method further includes, prior to step (b): contacting a plurality of first probes and second probes to the biological sample on the array, wherein the plurality of first probes and second probes target a plurality of nucleic acids in the biological sample, wherein a first probe and a second probe of the plurality comprise sequences that are substantially complementary to the analyte, wherein the analyte is a target nucleic acid, and wherein the second probe comprises a capture probe capture domain sequence that is complementary to all or a portion of the capture domain; hybridizing the first probe and the second probe to the target nucleic acid; generating a ligation product by ligating the first probe and the second probe; and releasing the ligation product from the target nucleic acid.

In some instances, the first probe and the second probe are substantially complementary to adjacent sequences of the target nucleic acid. In some instances, the first probe and the second probe hybridize to sequences that are not adjacent to each other on the target nucleic acid, and wherein the first probe is extended with a DNA polymerase, thereby (i) filling in a gap between the first probe and the second probe and (ii) generating an extended first probe. In some instances, the first probe further comprises a primer sequence. In some instances, the first probe and/or the second probe is a DNA probe. In some instances, the releasing the ligation product from the target nucleic acid comprises contacting the biological sample with an endoribonuclease, optionally wherein the endoribonuclease is an RNase H enzyme.

In some instances, the analyte derived molecule is an analyte capture agent. In some instances, the methods further include, prior to step (b): contacting the biological sample with a plurality of analyte capture agents, wherein the analyte capture agent comprises an analyte binding moiety and an oligonucleotide comprising an analyte binding moiety barcode and an analyte capture sequence, wherein the analyte capture sequence comprises a sequence complementary to the capture domain; and binding the analyte binding moiety of the analyte capture agent to the analyte, wherein the analyte is a protein. In some instances, step (b) comprises hybridizing the analyte capture sequence to the capture domain.

In some instances, the padlock probe or the snail probe comprises: (i) a first sequence that is substantially complementary to a first portion of the extended capture probe, the analyte derived molecule, or a complement thereof; (ii) a backbone sequence; and (iii) a second sequence that is substantially complementary to a second portion of the extended capture probe, the analyte derived molecule, or a complement thereof.

In some embodiments, the first sequence and the second sequence are substantially complementary to adjacent sequences of the extended capture probe, the analyte derived molecule, or a complement thereof. In some embodiments, the first sequence and the second sequence are substantially complementary to sequences of the extended capture probe, the analyte derived molecule, or a complement thereof, that are about 2 to 50 nucleotides apart.

In some embodiments, circularizing the padlock probe or the snail probe includes filling in a gap between the first sequence that is substantially complementary to a first portion of the analyte and the second sequence that is substantially complementary to a second portion of the analyte using a polymerase.

In some embodiments, the backbone sequence includes a backbone barcode sequence.

In some embodiments, circularizing the padlock probe or the snail probe includes ligating the padlock probe or the snail probe.

In some embodiments, the ligating includes enzymatic ligation or chemical ligation (e.g., click chemistry). In some embodiments, the enzymatic ligation utilizes ligase. In some embodiments, ligase includes a T4 DNA ligase.

In some embodiments, the amplifying includes rolling circle amplification (RCA). In some embodiments, the amplifying includes hybridizing one or more amplification primers to the padlock probe or the snail probe; and amplifying the padlock probe or the snail probe with a padlock probe or snail probe polymerase. In some embodiments, the padlock probe or snail probe polymerase has strand displacement activity. In some embodiments, the padlock probe or snail probe polymerase is a Phi29 DNA polymerase.

In some embodiments, the one or more amplification primers are substantially complementary to a portion of the padlock probe or the snail probe.

In some embodiments, the detection probe is about 10 to about 60 nucleotides in length.

In some embodiments, the detectable label includes a fluorophore.

In some embodiments, the detection probe is substantially complementary to a portion of the first sequence that is substantially complementary to a first portion of the analyte.

In some embodiments, the detection probe is substantially complementary to a portion of the second sequence that is substantially complementary to a second portion of the analyte.

In some embodiments, the detection probe is substantially complementary to a portion of the backbone sequence.

In some embodiments, the detection probe is substantially complementary to a portion of the analyte or a complement thereof.

In some embodiments, the extending step includes extending the capture probe using the analyte as the template. In some embodiments, the extending includes using a reverse transcriptase. In some embodiments, the reverse transcriptase includes a Moloney murine leukemia virus reverse transcriptase. In some embodiments, extending the capture probe includes using fluorescently tagged nucleotides to reverse transcribe the extended capture probe.

In some embodiments, the biological sample is permeabilized using a permeabilization agent. In some embodiments, the permeabilization agent includes proteinase K. In some embodiments, the permeabilization agent includes pepsin.

In some embodiments, the biological sample is permeabilized at room temperature.

In some embodiments, the biological sample is permeabilized at 37° C.

In some embodiments, the biological sample is permeabilized for about 1 minute to about 30 minutes.

In some embodiments, the method also includes varying permeabilization time to determine an optimal permeabilization time for minimizing analyte mislocalization in the biological sample.

In some embodiments, the method also includes varying permeabilization temperature to determine an optimal permeabilization temperature for minimizing analyte mislocalization in the biological sample.

In some embodiments, determining the mislocalization of the analyte includes measuring the signal intensity of the plurality of detection probes and comparing the signal intensity to a first image of the biological sample. In some embodiments, signal intensity in the image of the biological sample includes a single cell or cell type that expresses a biomarker that is detected when the biological sample is stained.

In some embodiments, the biological sample is stained prior to obtaining an image of the biological sample. In some embodiments, the biological sample is stained using immunofluorescence or immunohistochemistry techniques. In some embodiments, the biological sample is stained using hematoxylin and eosin (H&E).

In some embodiments, the image is a fluorescent image or a brightfield image.

In some embodiments, the image is obtained using a fluorescent microscope, a confocal microscope, or a brightfield microscope.

In some embodiments, the capture probe is affixed to the substrate at a 5' end of the capture probe.

In some embodiments, the plurality of capture probes are uniformly distributed on a surface of the substrate.

In some embodiments, the capture domain of the capture probe includes a homopolymeric sequence. In some embodiments, the capture domain of the capture probe includes a poly(T) sequence. In some embodiments, the capture domain of the capture probe includes a non-homopolymeric sequence. In some embodiments, the non-homopolymeric sequence includes a sequence substantially complementary to the analyte.

In some embodiments, the biological sample includes a FFPE sample. In some embodiments, the biological sample includes a fresh frozen sample. In some embodiments, the biological sample includes fixed or live cells. In some embodiments, the biological sample is from a mammal. In some embodiments, the biological sample is from a human, a mouse, or a rat.

In some embodiments, the biological sample includes a tissue section. In some embodiments, the tissue section is about 2.5 µm to about 20 µm in thickness.

In some embodiments, the method also includes varying the thickness of the tissue sample to determine an optimal tissue thickness to minimize mislocalization in the biological sample.

In some embodiments, the analyte is RNA. In some embodiments, the RNA is mRNA. In some embodiments, the analyte is a protein. In some embodiments, the protein is a cell surface marker. In some embodiments, the protein is an immune cell receptor.

In some embodiments, the method also includes obtaining a second biological sample. In some embodiments, the second biological sample is a second tissue section of the biological sample.

In some embodiments, the method also includes determining abundance and/or location of an analyte in the second biological sample, wherein the determining includes: (a) contacting a spatial array with the second biological sample, wherein the spatial array includes a plurality of spatial capture probes, wherein a spatial capture probe of the plurality of spatial capture probes includes a capture domain and a spatial barcode; (b) hybridizing the analyte to the spatial capture probe; and (c) determining (i) all or a part of the sequence of the analyte, or a complement thereof, and (ii) the sequence of the spatial barcode, or a complement thereof, and using the determined sequence of (i) and (ii) to determine the abundance and/or the location of the analyte in the biological sample. In some embodiments, the spatial capture probe further includes one or more functional domains, a unique molecular identifier (UMI), a cleavage domain, or combinations thereof. In some embodiments, the method also includes extending the spatial capture probe via a nucleic acid extension reaction using the analyte as a template to generate an extended spatial capture probe including the spatial capture probe and the reverse complement of the analyte. In some embodiments, the determining step (c) includes amplifying all or part of the analyte specifically bound to the spatial capture domain, or a complement thereof. In some embodiments, the determining step (c) includes sequencing. In some embodiments, the method can include imaging the biological sample.

In another aspect, this disclosure features kits, where the kits include: (a) an array including a plurality of capture probes, wherein a capture probe of the plurality of capture probes includes a capture domain; (b) a plurality of padlock probes and/or snail probes, wherein a padlock probe or a snail probe of the plurality of padlock probes and/or snail probes includes: (i) a first sequence that is substantially complementary to a first portion of an analyte, or a complement thereof, (ii) a backbone sequence, and (iii) a second sequence that is substantially complementary to a second portion of the analyte, or a complement thereof; (c) one or more enzymes selected from a ligase, a polymerase, a reverse transcriptase, or combinations thereof; (d) a plurality of detection probes; and (e) instructions for performing any one of the methods of described herein.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

The singular form "a", "an", and "the" include plural references unless the context clearly dictates otherwise. For example, the term "a cell" includes one or more cells, including mixtures thereof. "A and/or B" is used herein to include all of the following alternatives: "A", "B", "A or B", and "A and B".

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

BRIEF DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIGS. 12A-12C show magnified views of images from FIG. 11. Arrows indicate the same three exemplary lung tissue airways as indicated in FIG. 11. FIGS. 12D-12E show single molecule FISH (smFISH) images for Scgb1a1 transcripts (FIG. 12E) and Scgb1a1 transcripts merged with DAPI staining (FIG. 12D).

DETAILED DESCRIPTION

I. Introduction

Figure 1:
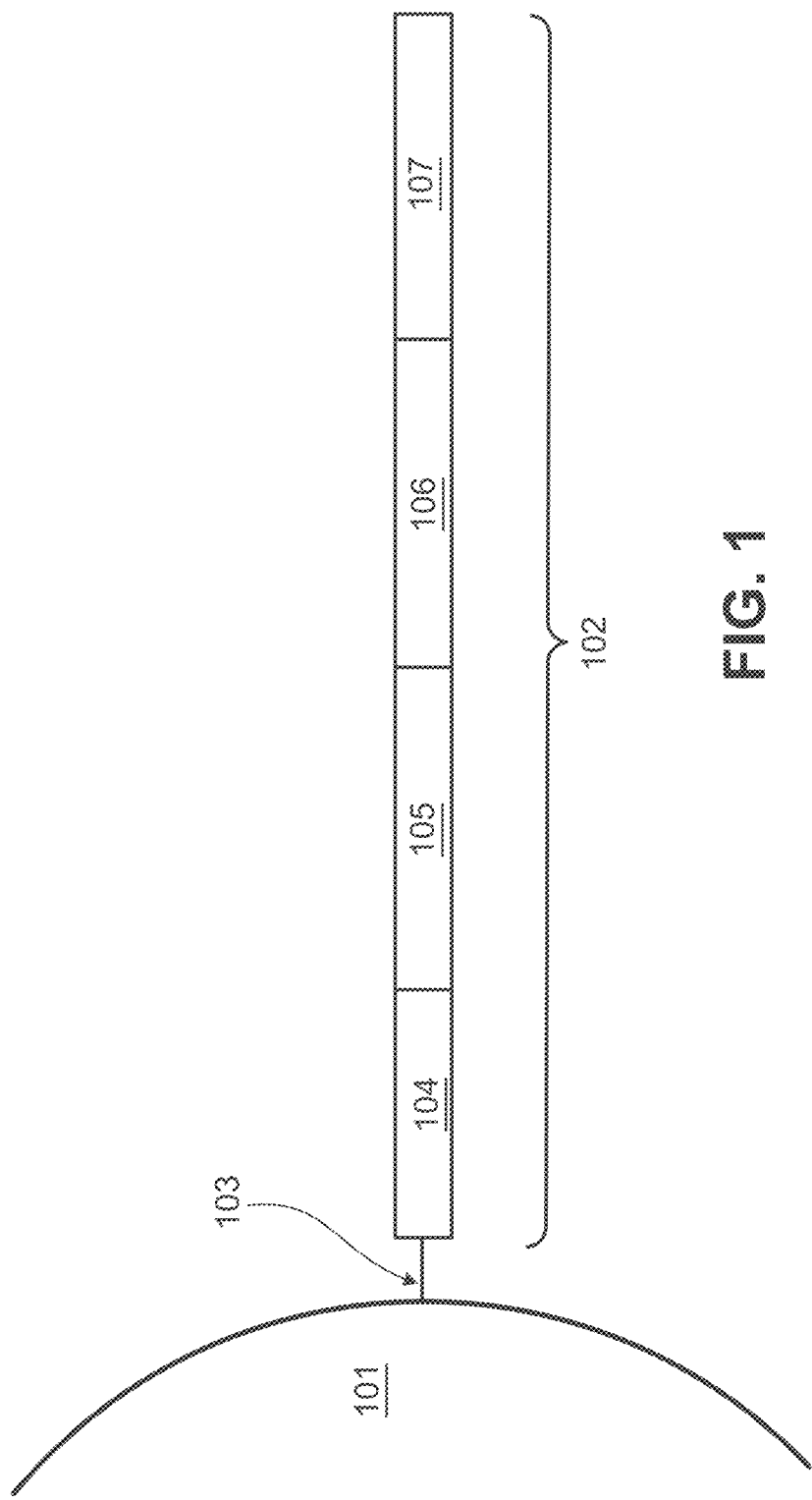
FIG. 1 is a schematic diagram showing an example of a capture probe, as described herein.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodriques et al., Science 363 (6434): 1463-1467, 2019; Lee et al., Nat. Protoc. 10 (3): 442-458, 2015; Trejo et al., PLOS ONE 14 (2): e0212031, 2019; Chen et al., Science 348 (6233): aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, an analyte derived molecule such as a connected probe (e.g., a ligation product) or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Some array-based spatial analysis methods involve the transfer of one or more analytes from a biological sample to an array of features on a substrate, where typically each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for amplification, or a flow cell attachment sequence, such as for next-generation sequencing (NGS)).

In some instance, the capture domain is designed to detect one or more specific analytes of interest. For example, a capture domain can be designed so that it comprises a sequence that is complementary or substantially complementary to one analyte of interest. Thus, the presence of a single analyte can be detected. Alternatively, the capture domain can be designed so that it comprises a sequence that is complementary or substantially complementary to a conserved region of multiple related analytes. In some instances, the multiple related analytes are analytes that function in the same or similar cellular pathways or that have conserved homology and/or function. The design of the capture probe can be determined based on the intent of the user and can be any sequence that can be used to detect an analyte of interest. In some embodiments, the capture domain sequence can therefore be random, degenerate, defined (e.g., gene or protein specific) or combinations thereof, depending on the target analyte(s) of interest.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that is useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequence 104 is common to all of the probes attached to a given feature. In some embodiments, the UMI sequence 106 of a capture probe attached to a given feature is different from the UMI sequence of a different capture probe attached to the given feature.

Figure 2:
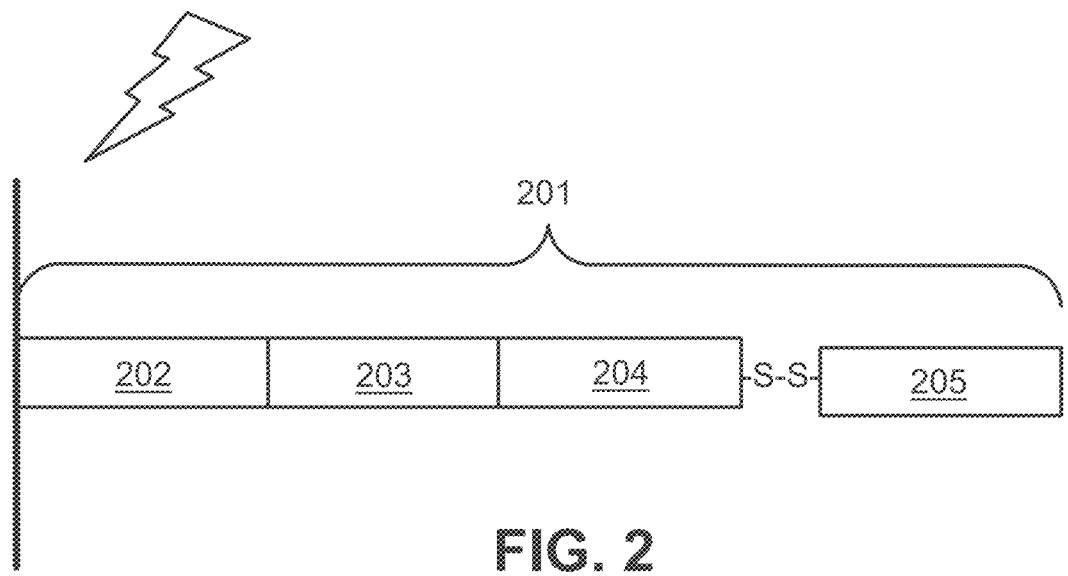
FIG. 2 is a schematic illustrating a cleavable capture probe, wherein the cleaved capture probe can enter into a non-permeabilized cell and bind to target analytes within the cell.

FIG. 2 is a schematic illustrating a cleavable capture probe, wherein the cleaved capture probe can enter into a non-permeabilized cell and bind to analytes within the cell. The capture probe 201 contains a cleavage domain 202, a cell penetrating peptide 203, a reporter molecule 204, and a disulfide bond (—S—S—). 205 represents all other parts of a capture probe, for example a spatial barcode and/or a capture domain.

Figure 3:
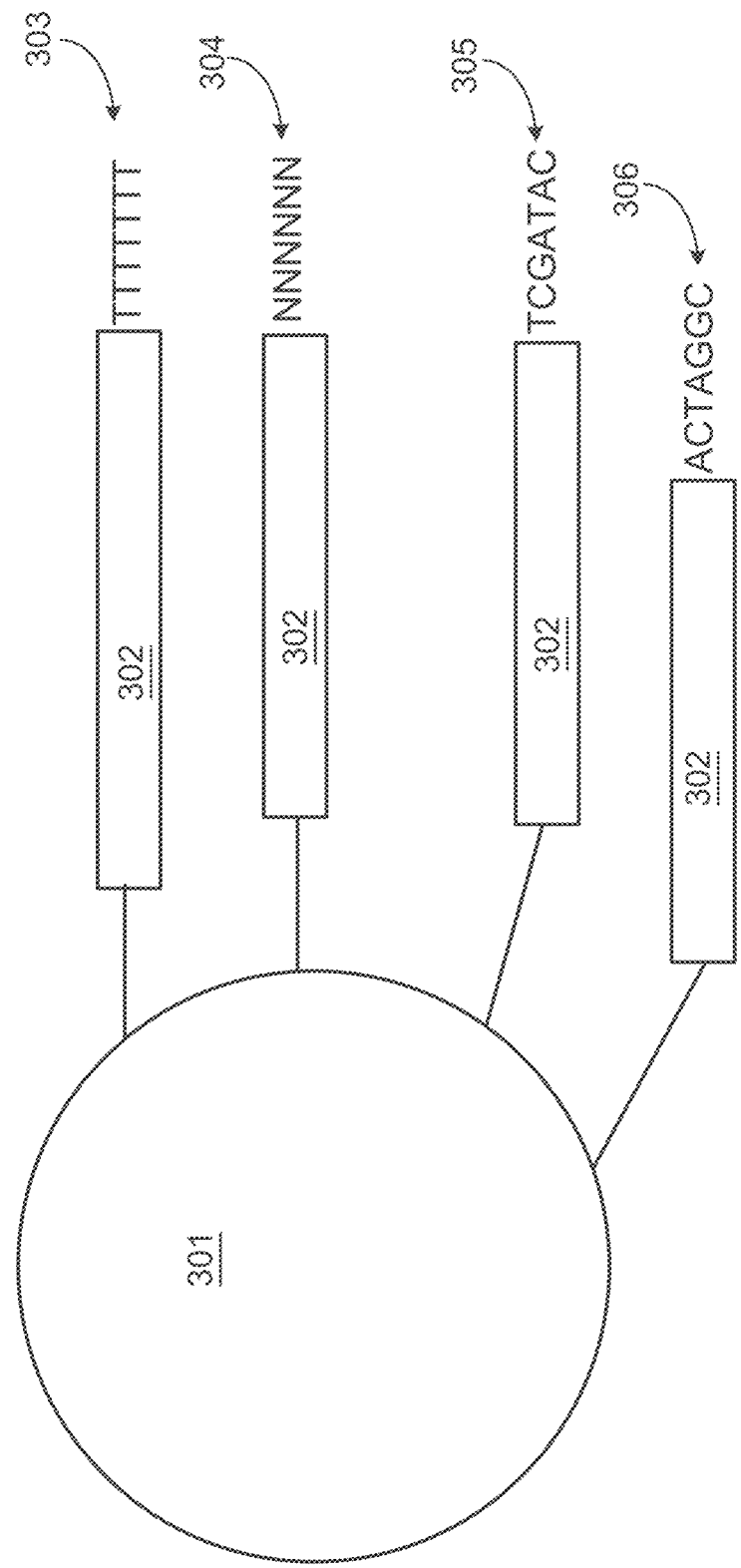
FIG. 3 is a schematic diagram of an exemplary multiplexed spatially-barcoded feature.

FIG. 3 is a schematic diagram of an exemplary multiplexed spatially-barcoded feature. In FIG. 3, the feature 301 can be coupled to spatially-barcoded capture probes, wherein the spatially-barcoded probes of a particular feature can possess the same spatial barcode 302, but have different capture domains designed to associate the spatial barcode of the feature with more than one target analyte. For example, a feature may be coupled to four different types of spatially-barcoded capture probes, each type of spatially-barcoded capture probe possessing the same spatial barcode 302. One type of capture probe associated with the feature includes the spatial barcode 302 in combination with a poly(T) capture domain 303, designed to capture mRNA target analytes. A second type of capture probe associated with the feature includes the same spatial barcode 302 in combination with a random N-mer capture domain 304 for gDNA analysis. A third type of capture probe associated with the feature includes the spatial barcode 302 in combination with a capture domain complementary to a capture handle sequence of an analyte capture agent of interest 305. A fourth type of capture probe associated with the feature includes the spatial barcode 302 in combination with a capture domain that can specifically bind a nucleic acid molecule 306 that can function in a CRISPR assay (e.g., CRISPR/Cas9). While only four different capture probe-barcoded constructs are shown in FIG. 3, capture-probe barcoded constructs can be tailored for analyses of any given analyte associated with a nucleic acid and capable of binding with such a construct. For example, the schemes shown in FIG. 3 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V (D) J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) a capture handle sequence. As used herein, the term "analyte binding moiety barcode" refers to a barcode that is associated with or otherwise identifies the analyte binding moiety. As used herein, the term "analyte capture sequence" or "capture handle sequence" refers to a region or moiety configured to hybridize to, bind to, couple to, or otherwise interact with a capture domain of a capture probe. In some embodiments, a capture handle sequence is complementary to a capture domain of a capture probe. In some cases, an analyte binding moiety barcode (or portion thereof) may be able to be removed (e.g., cleaved) from the analyte capture agent.

Figure 4:
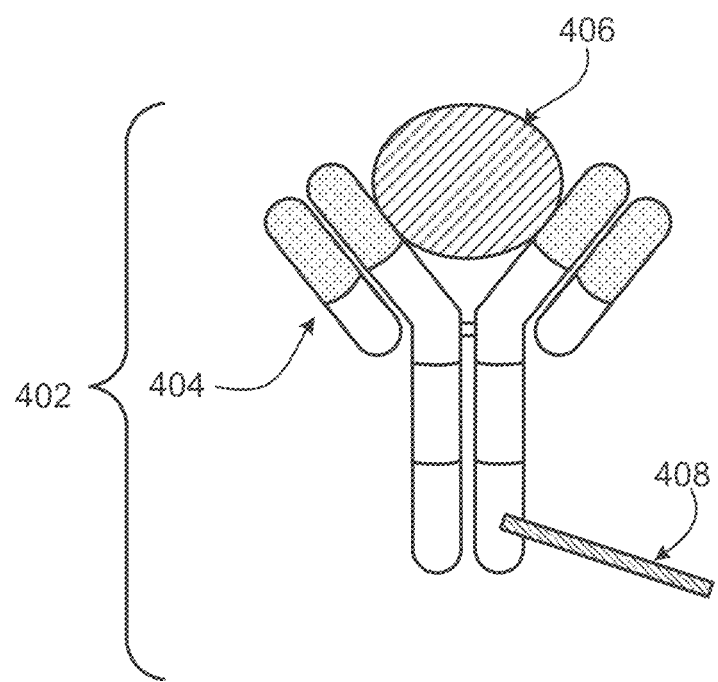
FIG. 4 is a schematic diagram of an exemplary analyte capture agent.

FIG. 4 is a schematic diagram of an exemplary analyte capture agent 402 comprised of an analyte-binding moiety 404 and an analyte-binding moiety barcode domain 408. The exemplary analyte-binding moiety 404 is a molecule capable of binding to an analyte 406 and the analyte capture agent is capable of interacting with a spatially-barcoded capture probe. The analyte-binding moiety can bind to the analyte 406 with high affinity and/or with high specificity. The analyte capture agent can include an analyte-binding moiety barcode domain 408, a nucleotide sequence (e.g., an oligonucleotide), which can hybridize to at least a portion or entirety of a capture domain of a capture probe. The analyte-binding moiety barcode domain 408 can comprise an analyte binding moiety barcode and a capture handle sequence described herein. The analyte-binding moiety 404 can include a polypeptide and/or an aptamer. The analyte-binding moiety 404 can include an antibody or antibody fragment (e.g., an antigen-binding fragment).

Figure 5:
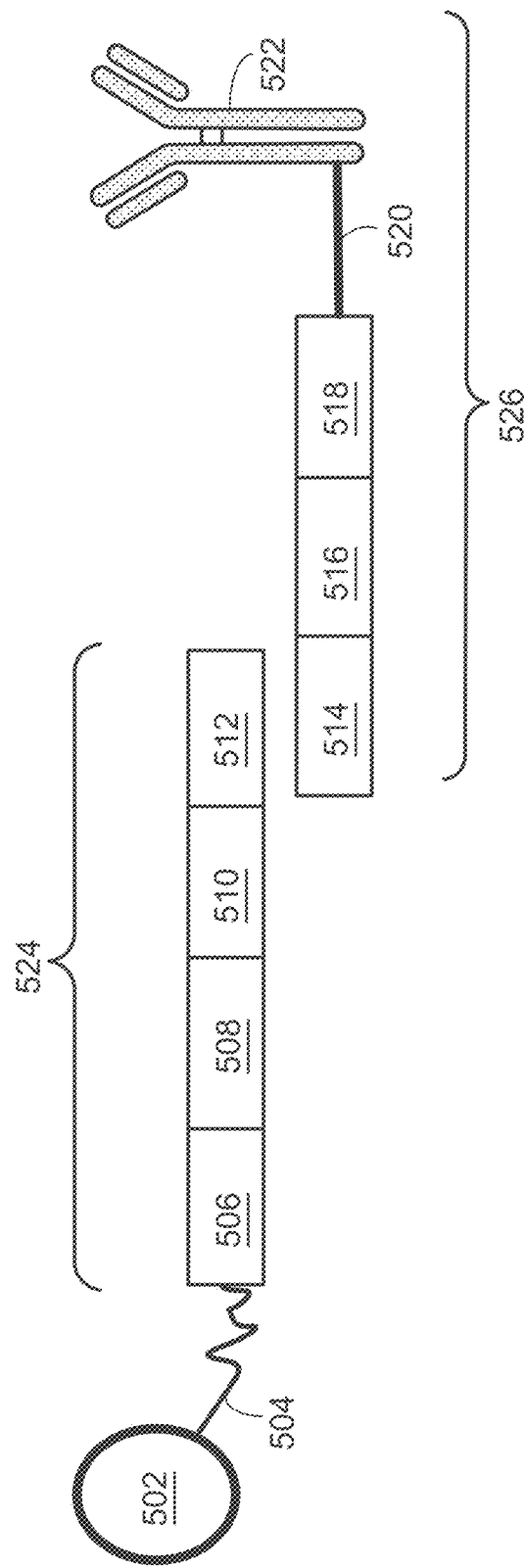
FIG. 5 is a schematic diagram depicting an exemplary interaction between a feature-immobilized capture probe 524 and an analyte capture agent 526.

FIG. 5 is a schematic diagram depicting an exemplary interaction between a feature-immobilized capture probe 524 and an analyte capture agent 526. The feature-immobilized capture probe 524 can include a spatial barcode 508 as well as functional sequences 506 and UMI 510, as described elsewhere herein. The capture probe can also include a capture domain 512 that is capable of binding to an analyte capture agent 526. The analyte capture agent 526 can include a functional sequence 518, analyte binding moiety barcode 516, and a capture handle sequence 514 that is capable of binding to the capture domain 512 of the capture probe 524. The analyte capture agent can also include a linker 520 that allows the capture agent barcode domain 516 to couple to the analyte binding moiety 522.

Figure 6A:
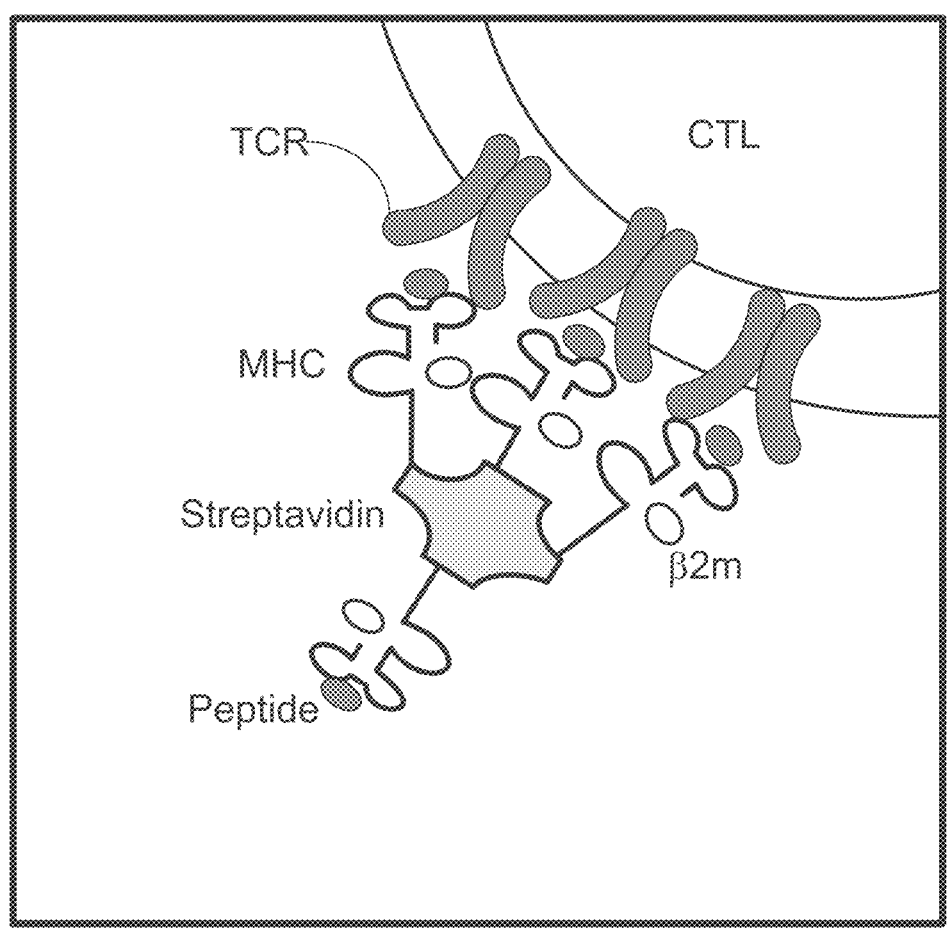
FIGS. 6A, 6B, and 6C are schematics illustrating how streptavidin cell tags can be utilized in an array-based system to produce a spatially-barcoded cells or cellular contents.
Figure 6B:
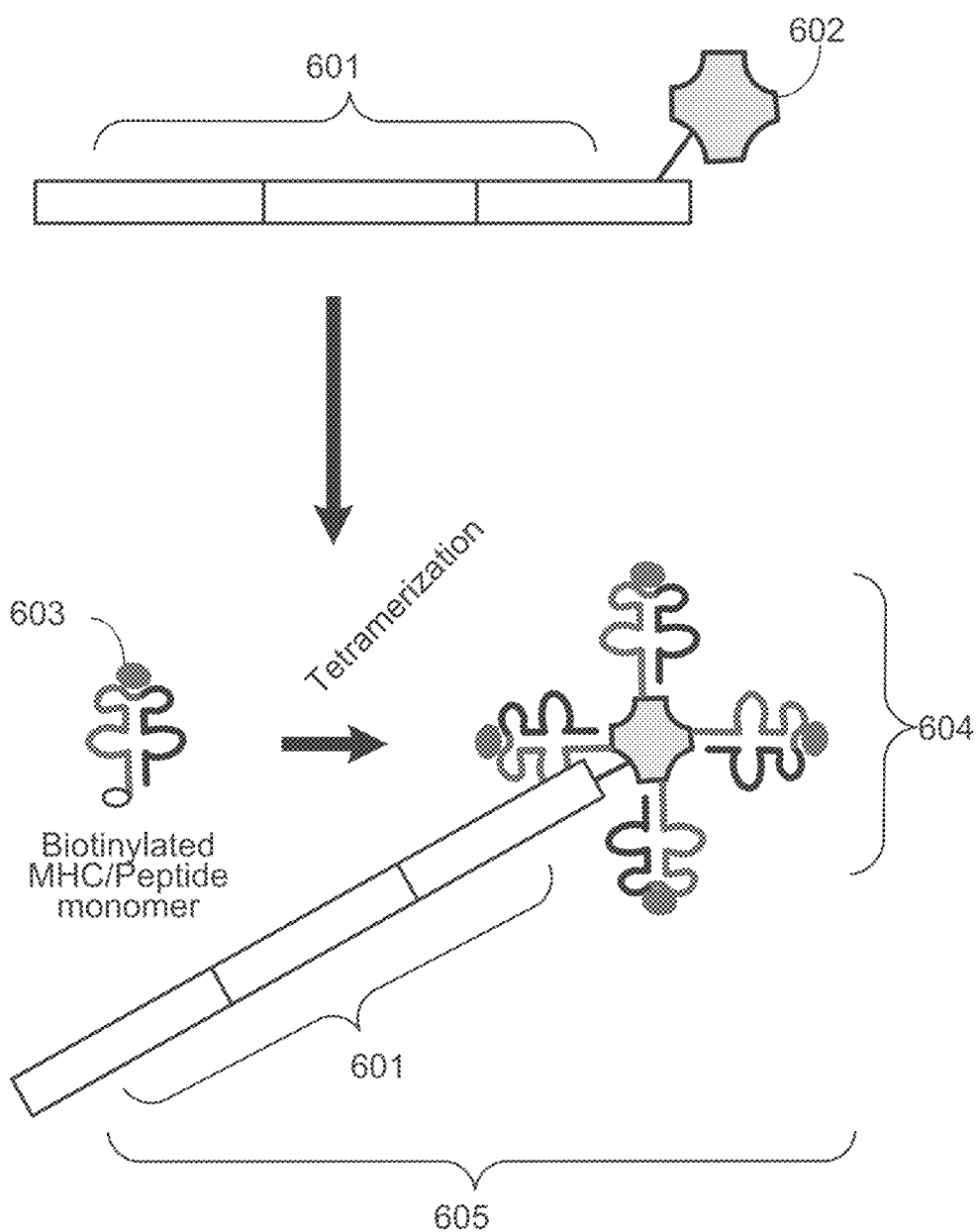
Figure 6C:
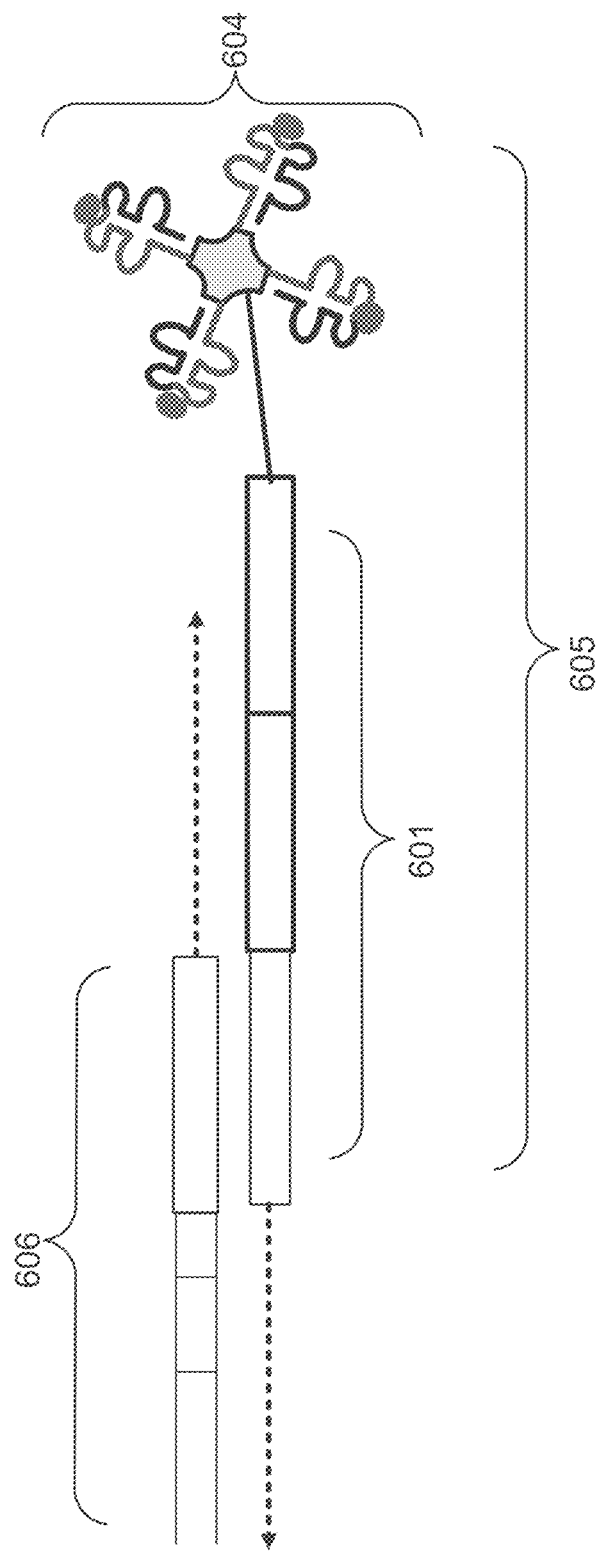

FIGS. 6A, 6B, and 6C are schematics illustrating how streptavidin cell tags can be utilized in an array-based system to produce a spatially-barcoded cell or cellular contents. For example, as shown in FIG. 6A, peptide-bound major histocompatibility complex (MHC) can be individually associated with biotin ($\beta$2m) and bound to a streptavidin moiety such that the streptavidin moiety comprises multiple pMHC moieties. Each of these moieties can bind to a T-Cell Receptor (TCR) such that the streptavidin binds to a target T-cell via multiple MCH/TCR binding interactions. Multiple interactions synergize and can substantially improve binding affinity. Such improved affinity can improve labelling of T-cells and also reduce the likelihood that labels will dissociate from T-cell surfaces. As shown in FIG. 6B, a capture agent barcode domain 601 can be modified with streptavidin 602 and contacted with multiple molecules of biotinylated MHC 603 such that the biotinylated MHC molecules 604 are coupled with the streptavidin conjugated capture agent barcode domain 601. The result is a barcoded MHC multimer complex 605. As shown in FIG. 6B, the capture agent barcode domain sequence 601 can identify the MHC as its associated label and also includes optional functional sequences such as sequences for hybridization with other oligonucleotides. As shown in FIG. 6C, one example oligonucleotide is capture probe 606 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1"), R2), a flow cell attachment sequence (e.g., P5 or P7 or partial sequences thereof)), etc. In some cases, capture probe 606 may at first be associated with a feature (e.g., a gel bead) and released from the feature. In other embodiments, capture probe 606 can hybridize with a capture agent barcode domain 601 of the MHC-oligonucleotide complex 605. The hybridized oligonucleotides (Spacer C C C and Spacer rGrGrG) can then be extended in primer extension reactions (see dashed lines adjacent to 606 and 601) such that constructs comprising sequences that correspond to each of the two spatial barcode sequences (the spatial barcode associated with the capture probe, and the barcode associated with the MHC-oligonucleotide complex) are generated. In some cases, one or both of these corresponding sequences may be a complement of the original sequence in capture probe 606 or capture agent barcode domain 601. In other embodiments, the capture probe and the capture agent barcode domain are ligated together. The resulting construct can be optionally further processed (e.g., to add any additional sequences and/or for clean-up) and subjected to sequencing. As described elsewhere herein, a sequence derived from the capture probe 606 spatial barcode sequence may be used to identify a feature and the sequence derived from spatial barcode sequence on the capture agent barcode domain 601 may be used to identify the particular peptide MHC complex 604 bound on the surface of the cell (e.g., when using pMHC libraries for screening immune cells or immune cell populations).

Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a connected probe (e.g., a ligation product) or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form a connected probe (e.g., a ligation product) with a template (e.g., a DNA or RNA template, such as an analyte or an intermediate agent, or portion thereof), thereby creating ligations products that serve as proxies for template extension.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe, a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities including capture probes, used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45 (14): e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a connected probe (e.g., a ligation product). In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the connected probe (e.g., a ligation product) is released from the tissue. In some instances, the connected probe (e.g., a ligation product) is released using an endonuclease (e.g., RNAse H). The released connected probe (e.g., a ligation product) can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the spatial array. Where necessary, the spatial arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e) (ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

The sandwich process is described in PCT Patent Application Publication No. WO 2020/123320, which is incorporated by reference in its entirety.

II. Methods and Compositions for Measuring Analyte Mislocalization Using Rolling Circle Amplification (a) Introduction Disclosed herein are methods for determining analyte mislocalization in a biological sample. As used herein, analyte mislocalization is determined by measuring the diffusion, or the migration of an analyte (e.g., an mRNA molecule), from a biological sample to an array comprising capture probes. In instances in which an analyte migrates to the closest probe in proximity to the analyte (i.e., migrating in a line that is perpendicular to the surface of the array, there is minimal to zero mislocalization. On the other hand, an analyte may migrate to probes that are not the probe closest in proximity to the analyte's original position in the biological sample, resulting in increased analyte mislocalization. In this instance, the distance between the location of the closest probe and the probe that ultimately captures the analyte is the mislocalization distance. Ideally, the mislocalization distance when transferring an analyte from a biological sample to the capture probe is zero or near-zero. However, in several instances, the mislocalization distance is not zero. It is appreciated by this disclosure that limiting the mislocalization distance for each sample tested (e.g., by varying parameters of permeabilization and by capturing only one or a few analytes) would increase resolution for determining the location of an analyte in a biological sample. Described herein are methods, kits, and compositions to determine the mislocalization distance of analytes using a fluorescent readout via rolling circle amplification of the captured analyte. The method allows a user to directly determine mislocalization of an analyte in a biological sample. Once the mislocalization distance parameters are optimized, a user can utilize these parameters on a related sample (e.g., in a serial section) and look more globally (e.g., at the entire transcriptome or proteome) at analyte expression. It is to be appreciated that different tissue types (e.g., porous, non-porous and dense tissue samples) may each have distinct analyte mislocalization profiles.

Thus, disclosed herein are methods of determining analyte mislocalization within a biological sample, the method including: (a) obtaining a first image of the biological sample; (b) hybridizing the analyte or analyte derived molecule to a capture probe on an array, wherein the array includes a plurality of capture probes, wherein a capture probe of the plurality of capture probe includes a capture domain; (c) optionally extending the capture probe using the analyte as a template, thereby generating an extended capture probe; (d) hybridizing a padlock probe or a snail probe to the analyte derived molecule or extended capture probe; (e) circularizing the padlock probe or the snail probe; (f) amplifying the padlock probe or the snail probe, thereby generating an amplified circularized padlock probe or an amplified circularized snail probe; (g) hybridizing a plurality of detection probes to the amplified circularized padlock probe or the amplified circularized snail probe, wherein a detection probe from the plurality of detection probes comprises: a sequence that is substantially complementary to a sequence of the padlock probe or the snail probe, or a complement thereof, and a detectable label; (h) obtaining a second image of the biological sample and detecting a signal from the plurality of detection probes in the second image; and (i) determining mislocalization of the analyte within the biological sample by comparing the first image of the biological sample to the second image of the biological sample.

Also disclosed herein are compositions and kits that are used in the methods.

(b) Methods of Measuring Analyte Mislocalization by Direct Capture of Analytes

In some embodiments, disclosed herein are methods of determining mislocalization of an analyte within a biological sample by capture of an analyte directly onto a substrate (e.g., hybridization of an analyte to a capture probe). In some instances, the analyte is RNA, such as mRNA. After obtaining a first image of the biological sample, the analyte hybridizes to a capture domain of a capture probe on an array, which comprises a plurality of capture probes, wherein the plurality of capture probes comprise a capture domain.

After hybridization, the capture probe is extended using a polymerase (e.g., a reverse transcriptase) to generate an extended capture probe. In some instances, extending the capture probe comprises using fluorescently tagged nucleotides to reverse transcribe the analyte. Either oligonucleotides containing fluorescently tagged nucleotides or individual fluorescently tagged nucleotides can be used. For instance, in some embodiments, individual fluorescently tagged nucleotides are used. The fluorescently tagged nucleotides can include a mixture of dNTPs comprises dATP, dTTP, dCTP, and dGTP, wherein at least one of the dATP, dTTP, dCTP, and dGTP is labeled with a fluorophore. In some instances, the capture probe is extended using non-labelled dNTP's to generate an extended capture probe lacking fluorescently tagged nucleotides.

At this point, the extended capture probe includes the capture probe and a complement of the analyte (or a portion thereof). Once the extended capture probe (e.g., cDNA molecule) is generated, the analyte (e.g., mRNA) can be dissociated from the capture probe. In some instances, this is performed using a solution comprising KOH. After dissociation of the analyte, the extended capture probe—which is single stranded—can interact with a padlock probe or a snail probe via hybridization. After hybridization of the padlock probe or snail probe, the padlock probe or snail probe is circularized, amplified, and detected using labeled detection probes, as described herein. A second image is obtained to determine the signal intensity from the plurality of detection probes in the second image. Comparing the first image and the second image allows one to determine mislocalization of the analyte within the biological sample by comparing the first image of the biological sample to the second image of the biological sample. For example, analyte mislocalization can be determined by comparing the expression of a cellular marker (e.g., for a particular cell type or morphology) found in the first image with the same, or similar, cellular marker in the second image. For example, Prox1 is expressed in several brain regions of mammals including the cortex, dentate gyrus (DG) region of the hippocampus, cerebellum, and hypothalamus. Since Prox1 expression is known to occur in the DG region of the hippocampus, mRNA transcripts encoding the Prox1 protein will also be present in the DG region of the hippocampus. Comparing and/or aligning the expression profile of the cellular markers allows one to determine (e.g., calculate) the relative distance an analyte has migrated from its original position in the biological sample.

(c) Methods of Measuring Analyte Mislocalization by Capture of Analyte Proxies (i) Templated Ligation In some embodiments, disclosed herein are methods that utilizes a nucleic acid proxy to determine mislocalization of an analyte. In some instances, the proxy is a ligation product derived from templated ligation. Methods of RNA-templated ligation (RTL) are disclosed in US 2021/0348221, US 2021/0285046, and WO 2021/133849, each of which is incorporated by reference in its entirety.

In an exemplary embodiment of the disclosure, provided are methods to determine mislocalization of an analyte on the array using templated ligation. In some instances, the methods include contacting a biological sample with array of capture probes. In some instances, the array is on a substrate and the array includes a plurality of capture probes, wherein a capture probe of the plurality includes a capture domain. After placing the biological sample on the array, the biological sample is contacted with a first probe and a second probe, wherein the first probe and the second probe each include one or more sequences that are substantially complementary to sequences of the analyte, and wherein the second probe includes a capture probe capture domain; the first probe and the second probe hybridize to complementary sequences in the analyte. After hybridization, a ligation product comprising the first probe and the second probe is generated, and the ligation product is released from the analyte. The liberated ligation product is then available to hybridize to the capture domain of a probe on the array. After capture on the array, padlock probes or snail probes described in section (II)(d) below can be used to determine mislocalization of the analyte on the array.

In another non-limiting example, a biological sample is deparaffinized, stained, and imaged. After destaining and decrosslinking, probes are added to the sample and hybridized to an analyte. In some instances, the probes are DNA probes. In some instances, the probes are diribo-containing probes. Probes are ligated to form a ligation product and released from the biological sample, for example using an endonuclease such as RNAse H. The ligation product can be captured on an array by a capture probe, where the ligation product can hybridize to a padlock probe or snail probe as described in section (II)(d) below.

In some embodiments, the ligation product includes a capture probe capture domain, which can hybridize to a capture probe (e.g., a capture probe immobilized, directly or indirectly, on a substrate). In some embodiments, methods provided herein include contacting a biological sample with a substrate, wherein the capture probe is affixed to the substrate (e.g., immobilized to the substrate, directly or indirectly). In some embodiments, the capture probe capture domain of the ligated product specifically binds to the capture domain. The capture probe can also include a unique molecular identifier (UMI), a spatial barcode, a functional sequence, a cleavage domain, or a combination thereof.

The methods provided herein utilize probe pairs (or probe sets; the terms are interchangeable). In some instances, the probe pairs are designed so that each probe hybridizes to a sequence in an analyte that is specific to the analyte (e.g., compared to the entire transcriptome). That is, in some instances, a single probe pair can be specific to a single analyte.

In other embodiments, probes can be designed so that one of the probes of a pair is a probe that hybridizes to a specific sequence. Then, the other probe can be designed to detect a mutation of interest. Accordingly, in some instances, multiple second probes can be designed and can vary so that each probe binds to a specific sequence. For example, a second probe can be designed to hybridize to a wild-type sequence, and another second probe can be designed to hybridize (and therefore detect) a mutated sequence. Thus, in some instances, a probe set can include one first probe and two second probes (or vice versa).

On the other hand, in some instances, probes can be designed so that they cover conserved regions of an analyte. Thus, in some instances, a probe (or probe pair can hybridize to similar analytes in a biological sample (e.g., to detect conserved or similar analytes) or in different biological samples (e.g., across different species).

In some embodiments, probe sets cover all or nearly all of a genome (e.g., human genome). In instances where probe sets are designed to cover an entire genome (e.g., the human genome), the methods disclosed herein can detect analytes in an unbiased manner. In some instances, one probe oligonucleotide pair is designed to cover one analyte (e.g., transcript). In some instances, more than one probe oligonucleotide pair (e.g., a probe pair comprising a first probe and a second probe) is designed to cover one analyte (e.g., transcript). For example, at least two, three, four, five, six, seven, eight, nine, ten, or more probe sets can be used to hybridize to a single analyte. Factors to consider when designing probes is presence of variants (e.g., SNPs, mutations) or multiple isoforms expressed by a single gene. In some instances, the probe oligonucleotide pair does not hybridize to the entire analyte (e.g., a transcript), but instead the probe oligonucleotide pair hybridizes to a portion of the entire analyte (e.g., transcript).

In some instances, about 100, 200, 300, 400, 500, 600, 700, 800, 900, 1000, 2000, 3000, 4000, 5000, 10000, 15000, 20000, or more probe oligonucleotides pair (e.g., a probe pair comprising a first probe and a second probe) are used in the methods described herein. In some instances, about 20,000 probe oligonucleotides pair are used in the methods described herein. In some embodiments, the subset of analytes includes 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 110, about 120, about 130, about 140, about 150, about 160, about 170, about 180, about 190, about 200, about 225, about 250, about 275, about 300, about 325, about 350, about 375, about 400, about 425, about 450, about 475, about 500, about 600, about 700, about 800, about 900, or about 1000 analytes.

In some embodiments, a first probe and/or the second probe includes a nucleic acid sequence that is about 10 nucleotides to about 100 nucleotides (e.g., a sequence of about 10 nucleotides to about 90 nucleotides, about 10 nucleotides to about 80 nucleotides, about 10 nucleotides to about 70 nucleotides, about 10 nucleotides to about 60 nucleotides, about 10 nucleotides to about 50 nucleotides, about 10 nucleotides to about 40 nucleotides, about 10 nucleotides to about 30 nucleotides, about 10 nucleotides to about 20 nucleotides, about 20 nucleotides to about 100 nucleotides, about 20 nucleotides to about 90 nucleotides, about 20 nucleotides to about 80 nucleotides, about 20 nucleotides to about 70 nucleotides, about 20 nucleotides to about 60 nucleotides, about 20 nucleotides to about 50 nucleotides, about 20 nucleotides to about 40 nucleotides, about 20 nucleotides to about 30 nucleotides, about 30 nucleotides to about 100 nucleotides, about 30 nucleotides to about 90 nucleotides, about 30 nucleotides to about 80 nucleotides, about 30 nucleotides to about 70 nucleotides, about 30 nucleotides to about 60 nucleotides, about 30 nucleotides to about 50 nucleotides, about 30 nucleotides to about 40 nucleotides, about 40 nucleotides to about 100 nucleotides, about 40 nucleotides to about 90 nucleotides, about 40 nucleotides to about 80 nucleotides, about 40 nucleotides to about 70 nucleotides, about 40 nucleotides to about 60 nucleotides, about 40 nucleotides to about 50 nucleotides, about 50 nucleotides to about 100 nucleotides, about 50 nucleotides to about 90 nucleotides, about 50 nucleotides to about 80 nucleotides, about 50 nucleotides to about 70 nucleotides, about 50 nucleotides to about 60 nucleotides, about 60 nucleotides to about 100 nucleotides, about 60 nucleotides to about 90 nucleotides, about 60 nucleotides to about 80 nucleotides, about 60 nucleotides to about 70 nucleotides, about 70 nucleotides to about 100 nucleotides, about 70 nucleotides to about 90 nucleotides, about 70 nucleotides to about 80 nucleotides, about 80 nucleotides to about 100 nucleotides, about 80 nucleotides to about 90 nucleotides, or about 90 nucleotides to about 100 nucleotides).

(ii) Protein Detection

In some embodiments, proteins in a biological sample can be detected using analyte capture agents, as described herein. In some embodiments, the analyte capture agents are contacted with the biological sample before the biological sample is contacted with an array. In some embodiments, the analyte capture agents are contacted with the biological sample after the biological sample is contacted with the array. In some embodiments, an analyte binding moiety of the analyte capture agent interacts (e.g., binds) with an analyte (e.g., protein) in a biological sample. In some embodiments, the analyte binding moiety is an antibody, aptamer or antigen-binding fragment.

Analyte capture agents can also include a conjugated oligonucleotide that can comprise one or more domains. For example, the conjugated oligonucleotide can include an analyte binding moiety barcode and an analyte capture sequence. In some embodiments, the analyte binding moiety barcode, or a complement thereof, refers to (e.g., identifies) a barcode that is associated with or otherwise identifies the analyte binding moiety. In some embodiments, the conjugated oligonucleotide can include an analyte capture sequence. In some embodiments, the analyte capture sequence is capable of interacting with (e.g., hybridizing) a capture domain of a capture probe on a substrate.

In some instances, an extended capture probe is generated using the analyte capture sequence as a template. In this instance, the padlock or snail probes (described in the Section (II)(d) below) can hybridize to the extended capture probe.

In some instances, no extended capture probe is generated using the analyte capture sequence as a template. In this instance, the padlock or snail probes (described in the Section (II)(d) below) hybridize directly to the analyte capture sequence.

In some embodiments, analyte capture agents are capable of binding to analytes present inside a cell. In some embodiments, analyte capture agents are capable of binding to cell surface analytes that can include, without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the analyte capture agents are capable of binding to cell surface analytes that are post-translationally modified. In such embodiments, analyte capture agents can be specific for cell surface analytes based on a given state of posttranslational modification (e.g., phosphorylation, glycosylation, ubiquitination, nitrosylation, methylation, acetylation or lipidation), such that a cell surface analyte profile can include posttranslational modification information of one or more analytes.

In some embodiments, the analyte capture agent includes a capture agent barcode domain that is conjugated or otherwise attached to the analyte binding moiety. In some embodiments, the capture agent barcode domain is covalently-linked to the analyte binding moiety. In some embodiments, a capture agent barcode domain is a nucleic acid sequence. In some embodiments, a capture agent barcode domain includes an analyte binding moiety barcode and an analyte capture sequence.

As used herein, the term "analyte binding moiety barcode" refers to a barcode that is associated with or otherwise identifies the analyte binding moiety. In some embodiments, by identifying an analyte binding moiety and its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein. For example, an analyte capture agent that is specific to one type of analyte can have coupled thereto a first capture agent barcode domain (e.g., that includes a first analyte binding moiety barcode), while an analyte capture agent that is specific to a different analyte can have a different capture agent barcode domain (e.g., that includes a second barcode analyte binding moiety barcode) coupled thereto. In some aspects, such a capture agent barcode domain can include an analyte binding moiety barcode that permits identification of the analyte binding moiety to which the capture agent barcode domain is coupled. The selection of the capture agent barcode domain can allow significant diversity in terms of sequence, while also being readily attachable to most analyte binding moieties (e.g., antibodies or aptamers) as well as being readily detected, (e.g., using sequencing or array technologies).

In some embodiments, the capture agent barcode domain of an analyte capture agent includes an analyte capture sequence. As used herein, the term "analyte capture sequence" refers to a region or moiety configured to hybridize to, bind to, couple to, or otherwise interact with a capture domain of a capture probe. In some embodiments, an analyte capture sequence includes a nucleic acid sequence that is complementary to or substantially complementary to the capture domain of a capture probe such that the analyte capture sequence hybridizes to the capture domain of the capture probe. In some embodiments, an analyte capture sequence comprises a poly(A) nucleic acid sequence that hybridizes to a capture domain that comprises a poly(T) nucleic acid sequence. In some embodiments, an analyte capture sequence comprises a poly(T) nucleic acid sequence that hybridizes to a capture domain that comprises a poly(A) nucleic acid sequence. In some embodiments, an analyte capture sequence comprises a non-homopolymeric nucleic acid sequence that hybridizes to a capture domain that comprises a non-homopolymeric nucleic acid sequence that is complementary (or substantially complementary) to the non-homopolymeric nucleic acid sequence of the analyte capture region.

In some embodiments of any of the methods described herein, the capture agent barcode domain coupled to the analyte binding moiety includes a cleavable domain. For example, after the analyte capture agent binds to an analyte (e.g., a cell surface analyte), the capture agent barcode domain can be cleaved and collected for downstream analysis according to the methods as described herein.

After the analyte capture sequence hybridizes to the capture domain, it can then interact with padlock probes or snail probes as described below.

(d) Padlock Probes and Snail Probes

This disclosure features a method for measuring the mislocalization of an analyte in a biological sample using rolling circle amplification (RCA). Initially, after hybridization of an analyte to a capture probe or the complement thereof, in some instances, a padlock probe hybridizes to the extended capture probe, analyte derived molecule, or the complement thereof. As used herein, a "padlock probe" refers to an oligonucleotide that includes, at its 5' and 3' ends, sequences (e.g., a first sequence at the 5' end and a second sequence at the 3' end) that are complementary to adjacent or nearby portions (e.g., a first portion and a second portion) of the analyte or an analyte derived molecule. Padlock probes are designed such that they comprise multiple substantially or fully complementary sequences to the analyte or analyte derived molecule. As described herein, an analyte includes nucleic acids (e.g., DNA or RNA) in some instances. An example of an analyte derived molecule includes a molecule comprising a protein binding moiety conjugated to an oligonucleotide. A further example is a product of RNA-templated ligation (RTL) as disclosed in US 2021/0348221, US 2021/0285046, and WO 2021/133849, each of which is incorporated by reference in its entirety. Examples and description of analyte derived molecule (also referred to as analyte binding moieties) has been described in WO 2020/176788 and/or U.S. 2020/0277663, each of which is incorporated by reference.

In some instances, Specific Nucleic Acid detection via Intramolecular Ligation (snail) probes are used. SNAIL-RCA (i.e., RCA using snail probes) uses an adaptation of the padlock probe/proximity ligation/rolling circle amplification process and has been shown to amplify the signal from RNA present at relatively low levels of expression. See e.g., O'Huallachain, M. et al. Communications Biology volume 3, Article number: 213 (2020); Nilsson, M. et al. Science. 7522346 (1994); and Wang, X. et al. Science. aat5691 (2018); each of which is incorporated by reference in its entirety. SNAIL-RCA was adopted for directed amplification of RNA in cells by proximity ligation. Typically, two primers are used, one of which binds to its target (e.g., an extended capture probe; a ligation product; or an oligonucleotide from an analyte capture agent; or any complements thereof) at a 3' position and contains the sequence cognate to a common ligation junction. The second primer contains a sequence proximal, which binds slightly upstream on the target, but which also anneals to the ligation junction. After ligation of the two SNAIL primers, rolling circle amplification occurs which results in amplification of the target or complement thereof.

Upon hybridization of the padlock probe or snail probe to the first and second portions (i.e., sequences) of the analyte or analyte derived molecule, the two ends of the padlock probe are either brought into contact, or an end is extended until the two ends are brought into contact, allowing circularization of the padlock probe or snail probe by ligation (e.g., ligation using any of the methods described herein). The ligation product can be referred to as the "circularized padlock probe" or "circularized snail probe." After circularization of the padlock probe or snail probe, rolling circle amplification can be used to amplify the circularized padlock probe or snail probe.

In some embodiments, a first sequence of a padlock probe or snail probe includes a sequence that is substantially complementary to a first portion of the analyte or analyte derived molecule. In some embodiments, the first portion of the analyte or analyte derived molecule is 5' to the second portion of the analyte or the analyte derived molecule. In some embodiments, the first sequence is at least 70% identical (e.g., at least 75% identical, at least 80% identical, at least 85% identical, at least 90% identical, at least 95% identical, or at least 99% identical) to the first portion.

In some embodiments, a backbone sequence of a padlock probe or snail probe includes a sequence that is substantially complementary to an amplification primer. The amplification primer can be a primer used in a rolling circle amplification reaction (RCA) of the ligated padlock probe or snail probe hybridized to the analyte or analyte derived molecules. Rolling circle amplification is well known in the art and includes a process by which circularized nucleic acid molecules are amplified with a DNA polymerase with strand displacement capabilities (and other necessary reagents for amplification to occur), thereby creating multiple concatenated copies of the circularized nucleic acid molecules. In some embodiments, the backbone sequence includes a functional sequence. In some embodiments, the backbone sequence includes a unique molecule identifier (UMI) or barcode sequence (e.g., any of the exemplary barcode sequences described herein). In some embodiments, the barcode sequence includes a sequence that is substantially complementary to an amplification primer. In some instances, the backbone UMI or backbone barcode sequence comprises a sequence (e.g., n=5-50 nucleotides) that is specific to the padlock probe or snail probe. In some instances, the backbone UMI or backbone barcode sequence in the padlock probe or snail probe can be used to identify the padlock or snail sequence.

In some embodiments, a second sequence of a padlock probe or snail probe includes a sequence that is substantially complementary to a second portion of the analyte or analyte derived molecule. In some embodiments, the second portion of the analyte or analyte derived molecule is 3' to the first portion of the analyte or the analyte derived molecule. In some embodiments, the second sequence is at least 70% identical (e.g., at least 75% identical, at least 80% identical, at least 85% identical, at least 90% identical, at least 95% identical, or at least 99% identical) to the second portion.

In some embodiments, the first sequence is substantially complementary to a first portion of the analyte or analyte derived molecule that is directly adjacent to the second portion of the analyte or analyte derived molecule to which the second sequence is substantially complementary. In such cases, the first sequence is ligated to the second sequence, thereby creating a circularized padlock probe or snail probe.

In some embodiments, the first sequence is substantially complementary to a first portion of the analyte or analyte derived molecule that is not directly adjacent to the second portion of the analyte or analyte derived molecule to which the second sequence is substantially complementary. In such cases, a "gap" exists between where the first sequence is hybridized to the first portion and where the second sequence is hybridized to the second portion. In some embodiments, there is a nucleotide sequence (e.g., a gap) in the analyte between the first portion and the second portion of at least 1-100, 1-90, 1-80, 1-70, 1-60, 1-50, 1-40, 1-30, 1-20, 1-10, 1-9, 1-8, 1-7, 1-6, 1-5, 1-4, 1-3, 1-2 or 1 nucleotide(s). In a non-limiting example, a first sequence having a sequence that is complementary to a sequence 5' of the gap and a second sequence having a sequence that is complementary to a sequence 3' of the gap each bind to an analyte leaving a sequence (e.g., the "gap") in between the first and second sequences that is gap-filled thereby enabling ligation and generation of the circularized padlock probe or snail probe. In some instances, to generate a padlock probe or snail probe that includes a first sequence and a second sequence that are close enough to one another to initiate a ligation step, the second sequence is extended enzymatically (e.g., using a reverse transcriptase).

In some embodiments, the "gap" sequence between the first sequence and the second sequence include one nucleotide, two nucleotides, three nucleotides, four nucleotides, five nucleotides, six nucleotides, seven nucleotides, eight nucleotides, nine nucleotides, ten nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, at least 25 nucleotides, at least 30 nucleotide, at least 35 nucleotides, at least 40 nucleotides, at least 45 nucleotides, or at least 50 nucleotides.

In some embodiments, extending the second sequence of the padlock probe or snail probe includes a nucleic acid extension reaction (e.g., any of the nucleic acid extension reactions described herein). In some embodiments, extending the second sequence of the padlock probe or snail probe includes reverse transcribing the analyte or analyte derived molecule. In some embodiments, extending the second sequence of the padlock probe or snail probe includes using a reverse transcriptase (e.g., any of the reverse transcriptases described herein). In some embodiments, extending the second sequence of the padlock probe or snail probe includes using a Moloney Murine Leukemia Virus (M-MMLV) reverse transcriptase. In some embodiments, the reverse transcriptase includes strand displacement properties. In some embodiments, extending the second sequence of the padlock probe generates a sequence that is complementary to the analyte or the analyte derived molecule. In some embodiments, extending the second sequence of the padlock probe or snail probe generates an extended second sequence of the padlock probe or snail probe that is complementary to the analyte or analyte derived molecule. In some embodiments, second sequence of the padlock probe or snail probe generates a sequence that is adjacent to the first sequence of the padlock probe or snail probe.

In some embodiments, the ligation step includes ligating the second sequence to the first sequence of the padlock probe or snail probe using enzymatic or chemical ligation. In some embodiments where the ligation is chemical ligation, the ligation reaction comprises click chemistry. In some embodiments where the ligation is enzymatic, the ligase is selected from a T4 RNA ligase (Rnl2), a SplintR ligase, a single stranded DNA ligase, or a T4 DNA ligase. In some embodiments, the ligase is a T4 RNA ligase (Rnl2) ligase. In some embodiments, the ligase is a pre-activated T4 DNA ligase as described herein. A non-limiting example describing methods of generating and using pre-activated T4 DNA include U.S. Pat. No. 8,790,873, the entire contents of which are herein incorporated by reference.

(e) Amplification of Padlock Probes or Snail Probes

This disclosure features a method for determining the mislocalization of an analyte in a biological sample using amplification of a circularized padlock probe or snail probe. In a non-limiting example, the method includes an amplifying step where one or more amplification primers are hybridized to the circularized padlock probe or snail probe and the circularized padlock probe or snail probe is amplified using a polymerase. Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo Klen- Taq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes. The amplification product(s) can be detected by hybridization of detection probes to the amplification product, which identify the location of the mislocalized analyte in the biological sample. The location of the mislocalized analyte can then be compared against an initial (or original) location of an analyte based on imaging prior to permeabilization of the biological sample and migration of the analytes. In some embodiments, the amplifying step includes rolling circle amplification (RCA).

As used herein, rolling circle amplification (RCA) refers to a polymerization reaction carried out using a single-stranded circular DNA (e.g., a circularized padlock probe or snail probe) as a template and an amplification primer that is substantially complementary to the single-stranded circular DNA (e.g., the circularized padlock probe or snail probe) to synthesize multiple continuous single-stranded copies of the template DNA (e.g., the circularized padlock probe or snail probe). In some embodiments, RCA includes hybridizing one or more amplification primers to the circularized padlock probe or snail probe and amplifying the circularized padlock probe or snail probe using a DNA polymerase with strand displacement activity, for example Phi29 DNA polymerase. In some embodiments, a first RCA reaction includes a first padlock probe or snail probe and a first amplification primer (or plurality of first amplification primers). A first RCA reaction can include the first padlock probe or snail probe hybridizing to a first analyte or first analyte derived molecule.

In some embodiments, an RCA reaction is carried out using a DNA polymerase and a dNTP mix including uracil, adenine, guanine and cytosine. In such cases, the uracils are incorporated into the amplified padlock probe or snail probe. In some embodiments, an RCA reaction is carried out using a DNA polymerase and a dNTP mix including uracil, adenine, guanine, cytosine and thymine. In such cases, uracils and thymines are both incorporated into the amplified padlock probe or snail probe.

In some instances, the dNTP molecule is labeled. In some instances, the label is a fluorescent label that is chemically coupled to the nucleotide. A fluorescent label can be attached to any of the following nucleotides dATP, dCTP, dGTP, dUTP, and dTTP. The fluorescent label can be any fluorescent label known in the art, including but not limited to cyanine 5 dye (Cy-5), cyanine 3 dye (Cy-3), fluorescein, rhodamine, phosphor, coumarin, polymethadine dye, fluorescent phosphoramidite, Texas red, green fluorescent protein, acridine, cyanine, and 5-(2'-aminoethyl)-aminonaphthalene-1-sulfonic acid (EDANS).

In some embodiments, the method further includes a second RCA reaction. For example, following a first RCA reaction, a second padlock probe or snail probe and a second amplification primer are added to the substrate. In some embodiments, the second padlock probe or snail probe hybridizes to a second analyte or second analyte derived molecule and is ligated thereby creating a second circularized padlock probe or snail probe. The second circularized padlock probe or snail probe can then be amplified using RCA.

In some embodiments, the second padlock probes or snail probes include a third sequence and a fourth sequence where each are substantially complementary to sequences on a second analyte (e.g., a different analyte then was bound by the first padlock probe or snail probe in the first RCA reaction). In some embodiments, the second padlock probe or snail probe includes: (i) a third sequence substantially complementary to the second analyte or second analyte derived molecule, (ii) a backbone sequence comprising a barcode, and (iii) a fourth sequence that is substantially complementary to a sequence adjacent to the third sequence in the second analyte or second analyte derived molecule. In some embodiments, the third sequence is at least 70% identical (e.g., at least 75% identical, at least 80% identical, at least 85% identical, at least 90% identical, at least 95% identical, or at least 99% identical) to a portion of the second analyte or second analyte derived molecule. In some embodiments, the fourth sequence is at least 70% identical (e.g., at least 75% identical, at least 80% identical, at least 85% identical, at least 90% identical, at least 95% identical, or at least 99% identical) to a sequence adjacent to the third sequence in the second analyte or second analyte derived molecule.

In some embodiments, the method further includes digesting the amplified circularized padlock probe or snail probe by using an enzyme that cleaves a nucleic acid sequence (e.g., an enzyme that cleaves nucleic acid sequences that include uracil). Digesting and/or removing the amplified circularized padlock probe or snail probe after detection of the detection probes can alleviate crowding that may result from the physical size of the RCA product and/or the detection probe. In some embodiments, the enzymatic digestion of the amplified circularized padlock probe or snail probe includes a uracil-DNA glycosylase (UDG) that cleaves nucleic acid sequences that include uracil incorporated into the amplified padlock probe or snail probe. In some embodiments, the enzyme is a combination of enzymes, such as UDG and DNA glycosylase lyase such as Endonuclease VIII.

In some embodiments, an amplification primer includes a sequence that is substantially complementary to one or more of the first sequence, the backbone sequence, or the second sequence of the padlock probe or snail probe. For example, the amplification primer can be substantially complementary to the backbone sequence. In some embodiments, the amplification primer includes a sequence that is substantially complementary to the padlock probe or snail probe and an additional portion of the analyte or analyte derived molecule. For example, the amplification primer can be substantially complementary to the backbone sequence and a portion of the analyte or analyte derived molecule that does not include the first and second portion of the padlock probe or snail probe. In some embodiments, the amplification primer includes a sequence that is substantially complementary to two or more of the first sequence, the backbone sequence, or the second sequence of the padlock probe or snail probe and an additional portion of the analyte or analyte derived molecule. By substantially complementary, it is meant that the amplification primer is at least 70%, at least 75%, at least 80%, at least 85%, at least 90%, at least 91%, at least 92%, at least 93%, at least 94%, at least 95%, at least 96%, at least 97%, at least 98%, at least 99%, complementary to a sequence in the circularized padlock probe or snail probe. By substantially complementary, it is meant that the amplification primer is at least 70%, at least 75%, at least 80%, at least 85%, at least 90%, at least 91%, at least 92%, at least 93%, at least 94%, at least 95%, at least 96%, at least 97%, at least 98%, at least 99% complementary to a sequence in the analyte or analyte derived molecule.

(f) Detection Probes and Signal Detection

This disclosure features a method for determining the mislocalization of an analyte in a biological sample using detection of a signal that corresponds to an amplified circularized padlock probe or snail probe (which thereby corresponds to an analyte or analyte binding molecule). In some embodiments, the method includes a step of detecting a signal corresponding to the amplified circularized padlock probe or snail probe on the substrate, thereby identifying the location of the mislocalized analyte in the biological sample. In some embodiments, the method includes a detecting step that includes determining (i) all or a part of the sequence of the amplified circularized padlock probe or snail probe on the substrate and using the determined sequence of the padlock probe or snail probe to identify the location of the analyte in the biological sample.

In some embodiments, the detecting step includes contacting the amplified circularized padlock probe or snail probe with a plurality of detection probes. In some embodiments, a detection probe of the plurality of detection probes includes a sequence that is substantially complementary to a sequence of the padlock probe or snail probe, circularized padlock probe or snail probe, or amplified circularized padlock probe or snail probe and a detectable label. For example, the detection probe of the plurality of detection probes can include a sequence that is substantially complementary to a sequence of amplified circularized padlock probe or snail probe and a detectable label. By substantially complementary, it is meant that the detection probe is at least 70%, at least 75%, at least 80%, at least 85%, at least 90%, at least 91%, at least 92%, at least 93%, at least 94%, at least 95%, at least 96%, at least 97%, at least 98%, at least 99% complementary to a sequence in the amplified circularized padlock probe or snail probe.

In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350 (350 N-Hydroxysuccinimide ester, a fluorophore with an excitation wavelength of about 350 nm), Alexa Fluor® 430 (430 N-Hydroxysuccinimide ester, a fluorophore with an excitation wavelength of about 430 nm), Alexa Fluor® 488 (488 N-Hydroxysuccinimide ester, a fluorophore with an excitation wavelength of about 488 nm), Alexa Fluor® 532 (532 N-Hydroxysuccinimide ester, a fluorophore with an excitation wavelength of about 532 nm), Alexa Fluor® 546 (546 N-Hydroxysuccinimide ester, a fluorophore with an excitation wavelength of about 546 nm), Alexa Fluor® 555 (555 N-Hydroxysuccinimide ester, a fluorophore with an excitation wavelength of about 555 nm), Alexa Fluor® 568 (568 N-Hydroxysuccinimide ester, a fluorophore with an excitation wavelength of about 568 nm), Alexa Fluor® 594 (594 N-Hydroxysuccinimide ester, a fluorophore with an excitation wavelength of about 594 nm), Alexa Fluor® 633 (633 N-Hydroxysuccinimide ester, a fluorophore with an excitation wavelength of about 633 nm), Alexa Fluor® 647 (647 N-Hydroxysuccinimide ester, a fluorophore with an excitation wavelength of about 647 nm), Alexa Fluor® 660 (660 N-Hydroxysuccinimide ester, a fluorophore with an excitation wavelength of about 660 nm), Alexa Fluor® 680 (680 N-Hydroxysuccinimide ester, a fluorophore with an excitation wavelength of about 680 nm), Alexa Fluor® 700 (700 N-Hydroxysuccinimide ester, a fluorophore with an excitation wavelength of about 700 nm), Alexa Fluor® 750 (750 N-Hydroxysuccinimide ester, a fluorophore with an excitation wavelength of about 750 nm), Allophycocyanin (APC), AMCA/AMCA-X, 7-Amino-4-methylcoumarin, 6-Aminoquinoline, Aniline Blue, ANS (1-anilinonaphthalene-8-sulfonate), APC-Cy™7 (allophycocyanin-Cyanine 7), ATTO-TAG™ CBQCA (3-(4-carboxybenzoyl) quinoline-2-carboxaldehyde), ATTO-TAG™ FQ (3-(2-furoyl) quinoline-2-carboxaldehyde), Auramine O-Feulgen, BCECF (2',7'-bis-(2-carboxyethyl)-5-(and-6)-carboxyfluorescein) (high pH), BFP (Blue Fluorescent Protein), BFP/GFP (Green Fluorescent Protein) FRET (Fluorescence Resonance Energy Transfer), BOBO™-1/BO-PRO™-1 (a blue-emitting fluorescent nucleic acid stain with an excitation wavelength of about 462 nm), BOBO™-3/BO-PRO™-3 (nucleic acid stain with an excitation wavelength of about 470 nm), BODIPY® FL (borondipyrromethene dye for fluorescein channel), BODIPY® TMR (borondipyrromethene dye for tetramethylrhodamine channel), BODIPY® TR-X (borondipyrromethene dye for the Texas Red® (sulforhodamine 101 acid chloride) channel with a succinimidyl ester modification), BODIPY® 530/550 (530/550 N-Hydroxysuccinimide ester, borondipyrromethene dye with an excitation wavelength of about 530 nm), BODIPY® 558/568 (558/568 N-Hydroxysuccinimide ester, borondipyrromethene dye with an excitation wavelength of about 558 nm), BODIPY® 564/570 (564/570 N-Hydroxysuccinimide ester, borondipyrromethene dye with an excitation wavelength of about 564 nm), BODIPY® 581/591 (581/591 N-Hydroxysuccinimide ester, borondipyrromethene dye with an excitation wavelength of about 581 nm), BODIPY® 630/650-X (630/650-X N-Hydroxysuccinimide ester, borondipyrromethene dye with an excitation wavelength of about 630 nm and a succinimidyl ester modification), BODIPY® 650-665-X (650/660-X N-Hydroxysuccinimide ester, borondipyrromethene dye with an excitation wavelength of about 650 nm and a succinimidyl ester modification), BTC (bromothenylcytosine), Calcein (Fluorescein-bis(methyliminodiacetic acid), Calcein Blue (4-Methylumbelliferone-8-methyliminodiacetic acid), Calcium Crimson™ (5-{[4-(bis{2-[(acetyloxy)methoxy]-2-oxoethyl}amino)-3-{2-[2-(bis{2-[(acetyloxy)methoxy]-2-oxoethyl}amino)phenoxy]ethoxy}phenyl]sulfamoyl}-2-(2,3,6,7,12,13,16,17-octahydro-1H,5H,11H,15H-pyrido[3,2,1-ij]quinolizino[1',9':6,7,8]chromeno[2,3-f]quinolin-4-ium-9-yl) benzenesulfonate, a cell-permeant light-excitable $Ca^{+2}$ indicator), Calcium Green-I™ (2,2'-((2-(2-(2-(bis(carboxylatomethyl)amino)-5-(3-carboxylato-4-(2,7-dichloro-6-oxido-3-oxo-3H-xanthen-9-yl)benzamido)phenoxy)ethoxy)phenyl)azanediyl)diacetate, a cell-permeant light-excitable $Ca^{+2}$ indicator), Calcium Orange™ (9-[4-[[[4-[bis[2-[(acetyloxy)methoxy]-2-oxoethyl]amino]-3-[2-[2-[bis[2-[(acetyloxy)methoxy]-2-oxoethyl]amino]phenoxy]ethoxy]phenyl]amino]thioxomethyl]amino]-2-carboxyphenyl]-3,6-bis(dimethylamino), a cell-permeant light-excitable $Ca^{+2}$ indicator), Calcofluor® White (4,4'-bis((2-anilino-4-(bis(2-hydroxyethyl)amino)-1,3,5-triazin-6-yl)amino) stilbene-2,2'-disulfonic acid, a fluorescent polysaccharide indicator), 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue® (N-(4-{[4-(diethylamino)phenyl][4-(ethylamino)-2-naphthyl]methylene}cyclohexa-2,5-dien-1-ylidene)-N-ethylethanaminium, a sulfonated pyrene dye with an excitation wavelength of about 396 nm), Cascade Yellow™ (5-{2-[1-(3-{[(2,5-dioxopyrrolidin-1-yl)oxy]carbonyl}benzyl)pyridinium-4-yl]-1,3-oxazol-5-yl}-2-methoxybenzenesulfonate, a sulfonated pyrene dye with an excitation wavelength of about 402 nm), CCF2 (Coumarin cephalosporin fluorescein), GeneBLAzer™ kit using a β-lactamase substrate), CFP (Cyan Fluorescent Protein), CFP/YFP FRET, Chromomycin A3, CINERF (low pH), CPM (7-Diethylamino-3-(4'-Maleimidylphenyl)-4-Methylcoumarin), 6-CR (6-Carboxyrhodamine) 6G, CTC (5-Cyano-2,3-ditolyl tetrazolium chloride) Formazan (emission peak, 630 nm), Cy2® (Cyanine2 N-Hydroxysuccinimide ester, tetramethylindo(di)-carbocyanine dye with excitation wavelength of about 490 nm), Cy3® (Cyanine3, tetramethylindo(di)-carbocyanine dye with excitation wavelength of about 555 nm), Cy3.5® (Cyanine3.5, tetramethylindo(di)-carbocyanine dye with excitation wavelength of about 591 nm), Cy5® (Cyanine5, tetramethylindo(di)-carbocyanine dye with excitation wavelength of about 646 nm), Cy5.5® (Cyanine5.5, tetramethylindo(di)-carbocyanine dye with excitation wavelength of about 675 nm), Cy7® (Cyanine7, tetramethylindo(di)-carbocyanine dye with excitation wavelength of about 743 nm), Cychrome (PE-Cy5®), Dansyl amine, Dansyl cadaverine, Dansyl chloride, DAPI (4',6-diamidino-2-phenylindole), Dapoxyl (2-aminoethyl) sulfonamide, DCFH (Diacetyldichlorofluorescein), DHR (Dihydrorhodamine), DiA (4-Di-16-ASP), DiD (DiIC18 (5)), DIDS (DiIC18 (5); 1, 1'-dioctadecyl-3,3,3',3'-tetramethylindodicarbocyanine, 4-chlorobenzenesulfonate), DiI (1,1'-Dioctadecyl-3,3,3',3'-Tetramethylindocarbocyanine Perchlorate; DiIC18 (3)), DiO (DiOC18 (3)), DiR (DiIC18 (7)), Di-4 ANEPPS (AminoNaphthylEthenylPyridinium), Di-8 ANEPPS, DM-NERF (4.5-6.5 pH), DsRed (Red Fluorescent Protein), EBFP (Enhanced Blue Fluorescent Protein), ECFP (Enhanced Cyan Fluorescent Protein), EGFP (Enhanced Green Fluorescent Protein), ELF®-97 alcohol (a phosphatase substrate), Eosin, Erythrosin, Ethidium bromide, Ethidium homodimer-1 (EthD-1), Europium (III) Chloride, 5-FAM (5-Carboxyfluorescein), Fast Blue (4-Benzoylamino-2,5-dimethoxyaniline), Fluorescein-dT phosphoramidite, FITC (Fluorescein isothiocyanate), Fluo-3, Fluo-4, FluorX® (carboxyfluorescein derivative), Fluoro-Gold™ (Hydroxystilbamidine, high pH), Fluoro-Gold™ (Hydroxystilbamidine, low pH), Fluoro-Jade, FM® 1-43 (neuron-specific fluorochrome), Fura-2 (high calcium), Fura-2/BCECF (2',7'-Bis-(2-Carboxyethyl)-5-(and-6), Fura Red™ (fura-2 analog, high calcium), Fura Red™ I Fluo-3 (fura-2 analog), GeneBLAzer™ (CCF2 B-lactamase substrate), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS (N-(Iodoacetaminoethyl)-1-naphthylamine-5-sulfonic acid), Indo-1 (high calcium), Indo-1 (low calcium), Indodicarbocyanine, Indotricarbocyanine, JC-I (5,5',6,6'-tetrachloro-1,1',3,3'-tetraethylbenzimidazolylcarbocyanine iodide), 6-JOE (6-Carboxy-4',5'-Dichloro-2',7'-Dimethoxyfluorescein), JOJO™-1/JO-PRO™-1 (nucleic acid stain with an excitation wavelength of about 532 nm), LDS 751 (+DNA), LDS 751 (+RNA), LOLO™-1/LO-PRO™-1 (nucleic acid stain with an excitation wavelength of about 565 nm), Lucifer Yellow (6-Amino-2,3-dihydro-1,3-dioxo-2-hydrazinocarbonylamino-1H-benz[d,e]isoquinoline-5,8-disulfonic acid dilithium salt), LysoSensor™ Blue (pH-sensitive ratiometric probe, pH 5), LysoSensor™ Green (pH-sensitive ratiometric probe, pH 5), LysoSensor™ Yellow/Blue (pH-sensitive ratiometric probe, pH 4.2), LysoTracker® Green (fluorophore linked to a weak base), LysoTracker® Red (fluorophore linked to a weak base), LysoTracker® Yellow (fluorophore linked to a weak base), Furaptra (MagFura-2), Mag-Indo-1 (2-(4-Amino-3-hydroxyphenyl) indole-6-carboxylic acid N',N',O'-triacetic acid tetrapotassium salt, Indo 1 analog tetrapotassium salt), Magnesium Green™ (fluorescent magnesium indicator), Marina Blue® (1,2-Dihexadecanoyl-sn-Glycero-3-Phosphoethanolamine, fluorescent carbohydrazide dye), 4-Methylumbelliferone, Mithramycin, MitoTracker® Green (mitochondria-specific green-fluorescent stain), MitoTracker® Orange (mitochondria-specific orange-fluorescent stain), MitoTracker® Red (mitochondria-specific red-fluorescent stain), NBD (amine), Nile Red, Oregon Green® 488 (green-fluorescent dye with an excitation wavelength of about 488 nm), Oregon Green® 500 (green-fluorescent dye with an excitation wavelength of about 500 nm), Oregon Green® 514 (green-fluorescent dye with an excitation wavelength of about 506 nm), Pacific Blue (3-carboxy-6,8-difluoro-7-hydroxycoumarin), PBFI (Potassium-binding Benzofuran Isophthalate Acetoxymethyl ester), PE (Rphycoerythrin), PE-Cy5, PE-Cy7, PE-Texas Red®, PerCP (Peridinin chlorphyll protein), PerCP-Cy5.5 (Peridinin chlorophyll protein-Cyanine5.5, TruRed), PharRed (APC-Cy7), C-phycocyanin, R-phycocyanin, R-phycoerythrin (PE), PI (Propidium Iodide), PKH26, PKH67, POPO™-1/PO-PRO™-1 (high-affinity carbocyanine dimeric nucleic acid stain), POPO™-3/PO-PRO™-3 (high-affinity carbocyanine dimeric nucleic acid stain), PyMPO (1-(3-carboxybenzyl)-4-(5-(4-methoxyphenyl) oxazol-2-yl)pyridinium bromide), Pyrene, Pyronin Y, Quantam Red (PE-Cy5), Quinacrine mustard, R670 (PE-Cy5), Red 613 (PE-Texas Red®), Red Fluorescent Protein (DsRed), Resorufin, RH 414, Rhod-2, Rhodamine B, Rhodamine Green™ (triarylmethane dye), Rhodamine Red™ (triarylmethane dye), Rhodamine Phalloidin, Rhodamine 110, Rhodamine 123, 5-ROX (5-carboxy-X-rhodamine), S65A, S65C, 5 S65L, S65T, SBFI (Sodium-binding benzofuran isophthalate), SITS (Stilbene isothiosulphonic acid), SNAFL®-1 (5' (and 6')-carboxyseminaphthofluorescein, high pH), SNAFL®-2 (carboxy seminaphthofluorescein), SNARF®-1 (pH-dependent fluorescent dye, high pH), SNARF®-1 (pH-dependent fluorescent dye, low pH), Sodium Green™ (tetra (tetramethylammonium) salt, fluorescent sodium indicator), SpectrumAqua® (fluorophore with excitation wavelength of about 433 nm), SpectrumGreen™ #1 (fluorophore with excitation wavelength of about 497 nm), SpectrumGreen™ #2 (fluorophore with excitation wavelength of about 509 nm), SpectrumOrange™ (fluorophore with excitation wavelength of about 559 nm), SpectrumRed™ (fluorophore with excitation wavelength of about 587 nm), SYTOR 11 (fluorophore with excitation wavelength of about 508 nm), SYTOR 13 (fluorophore with excitation wavelength of about 488 nm), SYTO® 17 (fluorophore with excitation wavelength of about 621 nm), SYTOR 45 (fluorophore with excitation wavelength of about 452 nm), SYTOX® Blue (fluorophore with excitation wavelength of about 445 nm), SYTOX® Green (fluorophore with excitation wavelength of about 504 nm), SYTOX® Orange (fluorophore with excitation wavelength of about 547 nm), 5-TAMRA (5-Carboxytetramethylrhodamine), Tetramethylrhodamine (TRITC), Texas Red® I Texas Red®-X (fluorophore with excitation wavelength of about 595 nm), Texas Red®-X (fluorophore with excitation wavelength of about 595 nm and N-Hydroxysuccinimide Ester modification), Thiadicarbocyanine, Thiazole Orange, TOTO®-1/TO-PRO®-1 (thiazole orange homodimer nucleic acid stain), TOTO®-3 I TO-PRO®-3 (thiazole red homodimer nucleic acid stain), TO-PRO®-5 (carbocyanine-based nucleic acid stain), Tri-color (PE-Cy5), WW 781 ([3-methyl-1-p-sulfophenyl-5-pyrazolone-(4)]-[1,3-dibutylbarbit uric acid]-pentamethine oxonol), X-Rhodamine (XRITC), Y66F, Y66H, Y66 W, YFP (Yellow Fluorescent Protein), YOYOR-1/YO-PRO®-1 (monomethine cyanine nucleic acid stain), YOYO®-3/YO-PROR-3 (monomethine cyanine nucleic acid stain), 6-FAM (Fluorescein), 6-FAM (N-Hydroxysuccinimide ester), 6-FAM (Azide), HEX (Hexachlorofluorescein), TAMRA (Tetramethylrhodamine, N-Hydroxysuccinimide Ester), Yakima Yellow®, MAX, TET (Tetrachloro fluorescein), TEX615, ATTO 488, ATTO 532, ATTO 550, ATTO 565, ATTO Rholol, ATTO 590, ATTO 633, ATTO 647N, TYE 563, TYE 665, TYE 705, 5' IRDye® 700 (infrared fluorescent nucleic acid stain), 5' IRDye® 800 (infrared fluorescent nucleic acid stain), 5' IRDye® 800CW (infrared fluorescent nucleic acid stain with an N-Hydroxysuccinimide ester modification), Well-RED D4 Dye (cyanine-based near-infrared dye), WellRED D3 Dye (cyanine-based near-infrared dye), WellRED D2 Dye (cyanine-based near-infrared dye), Lightcycler® 640 (red fluorescent dye with an N-Hydroxysuccinimide ester modification), and Dy 750 (betainic dye with an N-Hydroxysuccinimide ester modification).

In some embodiments, a detection probe of the plurality of detection probes includes a nucleotide sequence that is different from other detection probes, thereby enabling detection of signals from two or more detection probe sequences (e.g., two or more different amplified circularized padlock probe or snail probe). In some embodiments, each of the two or more different nucleotide sequences is located on the same amplified circularized padlock probe or snail probe. In some embodiments, each of the two or more different sequences is located on two or more different amplified circularized padlock probe or snail probes (e.g., each amplified circularized padlock probe or snail probe is derived from a different analyte or analyte derived molecule).

In some embodiments, the detecting step includes contacting the amplified circularized padlock probe or snail probe with a detectable label that can hybridize to nucleic acid sequences in a non-sequence dependent manner. In such cases, the single-stranded copies of the template DNA produced by RCA can be detected using fluorescent dyes that non-specifically bind to the single-stranded nucleic acid (e.g., the amplified circularized padlock probe or snail probe). For example, in the case where an analyte is an amplified circularized padlock probe or snail probe, a fluorescent dye can bind, either directly or indirectly, to the single stranded nucleic acid of the RCA product. The dye can then be detected as a signal corresponding to the amplified circularized padlock probe or snail probe (i.e., the location and/or the abundance of the circularized padlock probe or snail probe). Non-limiting examples of fluorescent dyes that can bind to single stranded nucleic acids include: TOTOR-1/TO-PRO®-1, TOTO®-3/TO-PRO®-3, TO-PRO®-5, Ethidium bromide, Ethidium homodimer-1 (EthD-1), YOYO®-1/YO-PRO®-1, YOYO®-3/YO-PRO®-3, 7-AAD (7-Aminoactinomycin D), and Oli-Green®.

In some embodiments, the detecting step includes contacting the amplified circularized padlock probe or snail probe with a detection probe (e.g., any of the exemplary detection probes described herein (e.g., a detection probe that includes one or more fluorophores)) and a fluorescent dye that can label single-stranded DNA in a non-sequence dependent manner (e.g., any of the exemplary fluorescent dyes described herein). In such cases, the fluorescent dye can be used to normalize the fluorescent signal detected from the detection probe.

In some embodiments, detecting the signal or signals that correspond to the amplified circularized padlock probes or snail probes on the substrate include obtaining an image corresponding to the analyte and/or analyte derived molecule on the substrate. In some embodiments, the method further includes registering image coordinates to a fiducial marker.

In some embodiments, the method includes repeating the detecting step with a second plurality of detection probes. In such cases, the method includes removing the detection probes from the first detecting step (e.g., via enzymatic digestion) and contacting the amplified circularized padlock probe or snail probe with a second plurality of detection probes. A detection probe of the second plurality of detection probes includes a sequence that is substantially complementary to a sequence of the padlock probe or snail probe and that is non-overlapping, partially overlapping, or completely overlapping with the sequence to which a detection probe from the first plurality of detection probes is substantially complementary.

In some embodiments, determining (i) all or a part of the sequence of the amplified circularized padlock probe or snail probe on the substrate includes determining the barcode sequence on the padlock probe or snail probe, wherein the location of the analyte in the biological sample can be identified. In situ sequencing of the analyte or analyte derived molecule, the nucleic acid molecule, the analyte binding moiety barcode, or the ligation product process is described in PCT Patent Application Publication No. WO 2020/047005, which is incorporated by reference in its entirety.

(g) Slides, Biological Samples, Analytes, and Preparation of the Same (i) Slides, Biological Samples, and Analytes This disclosure features a method for identifying a location of an analyte in a biological sample using a substrate that includes a plurality of capture probes, where a capture probe of the plurality of capture probes include a capture domain. In some embodiments, the capture probe is affixed to the substrate at a 5' end. In some embodiments, the plurality of capture probes are uniformly distributed on a surface of the substrate, following no particular pattern. In some embodiments, the plurality of capture probes are located on a surface of the substrate but are distributed on the substrate according to a pattern. In some instances, the capture probes do not include spatial barcodes. Instead, to determine mislocalization of an analyte, spatial analysis is performed with the aid of fluorescent readout, as described herein. Thus, in some instances, the substrate comprises a lawn of capture probes that include a capture domain, but do not include a spatial barcode.

In other embodiments, the substrate includes a plurality of capture probes, where a capture probe of the plurality of capture probes includes a capture domain and a spatial barcode. In some embodiments, the substrate includes a fiducial marker (e.g., any of the fiducial markers described herein). The fiducial markers can be used as a point of reference on the substrate. For example, the spatial location of a signal detected from a detection probe can be determined by using the fiducial marker as a point of reference on the substrate. In some cases, the fiducial marker can be present on a substrate to aid in orientation of the biological sample. In some embodiments, a fiducial marker can be an immobilized molecule with which a detectable signal molecule (e.g., a detectable label from a detection probe) can interact to generate a signal. For example, a fiducial marker can comprise a nucleic acid linked or coupled to a chemical moiety capable of fluorescing when subjected to light of a specific wavelength (or range of wavelengths) at a fixed position on the substrate.

In some embodiments, the biological sample comprises a tissue section. In some embodiments, the biological sample comprises a fresh frozen sample. In some embodiments, the biological sample comprises live or fixed single cells. In some embodiments, the biological sample comprises a FFPE sample.

In some embodiments, the method includes obtaining an image of the biological sample; registering the image data to spatial locations on an array. In some embodiments, the imaging includes a brightfield image. In some embodiments, the method further includes contacting the biological sample with one or more stains. In some embodiments, the one or more stains comprise a histology stain (e.g., any of the histology stains described herein or known in the art). In some embodiments, the one or more stains comprises hematoxylin and/or eosin. In some embodiments, the one or more stains comprise one or more optical labels (e.g., any of the optical labels described herein). In some embodiments, the one or more optical labels are selected from the group consisting of: fluorescent, radioactive, chemiluminescent, calorimetric, or colorimetric labels.

In some embodiments, the methods are applied to analyte, or analyte derived molecules (e.g., an mRNA molecule, a gDNA molecule, a product of reverse transcription (e.g., an extended capture probe), and an analyte binding moiety barcode (e.g., a binding moiety barcode that identifies that analyte binding moiety (e.g., an antibody))). In some embodiments, the analyte or analyte derived molecules comprise RNA and/or DNA. In some embodiments, the analyte or analyte derived molecules comprise one or more proteins.

(ii) Imaging and Staining

In some instances, biological samples can be stained using a wide variety of stains and staining techniques. In some instances, the biological sample is stained before adding the probes to the biological sample. In some instances, the biological sample is stained after adding the probes to the biological sample.

In some instances, the biological sample is a section of a tissue (e.g., a 10 µm section). In some instances, the biological sample is dried after placement onto a glass slide. In some instances, the biological sample is dried at 42° C. In some instances, drying occurs for about 1 hour, about 2, hours, about 3 hours, or until the sections become transparent. In some instances, the biological sample can be dried overnight (e.g., in a desiccator at room temperature).

In some embodiments, a sample can be stained using any number of biological stains, including but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin. In some instances, the methods disclosed herein include imaging the biological sample. In some instances, imaging the sample occurs prior to deaminating the biological sample. In some instances, the sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation. In some instances, the stain is an H&E stain.

In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes identifying analytes using fluorescently-conjugated antibodies. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) for the same biological sample.

In some embodiments, biological samples can be destained. Methods of destaining or decoloring a biological sample are known in the art, and generally depend on the nature of the stain(s) applied to the sample. For example, H&E staining can be destained by washing the sample in HCl, or any other acid (e.g., selenic acid, sulfuric acid, hydroiodic acid, benzoic acid, carbonic acid, malic acid, phosphoric acid, oxalic acid, succinic acid, salicylic acid, tartaric acid, sulfurous acid, trichloroacetic acid, hydrobromic acid, hydrochloric acid, nitric acid, orthophosphoric acid, arsenic acid, selenous acid, chromic acid, citric acid, hydrofluoric acid, nitrous acid, isocyanic acid, formic acid, hydrogen selenide, molybdic acid, lactic acid, acetic acid, carbonic acid, hydrogen sulfide, or combinations thereof). In some embodiments, destaining can include 1, 2, 3, 4, 5, or more washes in an acid (e.g., HCl). In some embodiments, destaining can include adding HCl to a downstream solution (e.g., permeabilization solution). In some embodiments, destaining can include dissolving an enzyme used in the disclosed methods (e.g., pepsin) in an acid (e.g., HCl) solution. In some embodiments, after destaining hematoxylin with an acid, other reagents can be added to the destaining solution to raise the pH for use in other applications. For example, SDS can be added to an acid destaining solution in order to raise the pH as compared to the acid destaining solution alone. As another example, in some embodiments, one or more immunofluorescence stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., J. Histochem. Cytochem. 2017; 65 (8): 431-444, Lin et al., Nat Commun. 2015; 6:8390, Pirici et al., J. Histochem. Cytochem. 2009; 57:567-75, and Glass et al., J. Histochem. Cytochem. 2009; 57:899-905, the entire contents of each of which are incorporated herein by reference.

In some embodiments, immunofluorescence or immunohistochemistry protocols (direct and indirect staining techniques) can be performed as a part of, or in addition to, the exemplary spatial workflows presented herein. For example, tissue sections can be fixed according to methods described herein. The biological sample can be transferred to an array (e.g., capture probe array), wherein analytes (e.g., proteins) are probed using immunofluorescence protocols. For example, the sample can be rehydrated, blocked, and permeabilized (3×SSC, 2% BSA, 0.1% Triton X, 1 U/µl RNAse inhibitor for 10 minutes at 4° C.) before being stained with fluorescent primary antibodies (1:100 in 3×SSC, 2% BSA, 0.1% Triton X, 1 U/µl RNAse inhibitor for 30 minutes at 4° C.). The biological sample can be washed, coverslipped (in glycerol+1 U/µl RNAse inhibitor), imaged (e.g., using a confocal microscope or other apparatus capable of fluorescent detection), washed, and processed according to analyte capture or spatial workflows described herein.

In some instances, a glycerol solution and a cover slip can be added to the sample. In some instances, the glycerol solution can include a counterstain (e.g., DAPI).

As used herein, an antigen retrieval buffer can improve antibody capture in IF/IHC protocols. An exemplary protocol for antigen retrieval can be preheating the antigen retrieval buffer (e.g., to 95° C.), immersing the biological sample in the heated antigen retrieval buffer for a predetermined time, and then removing the biological sample from the antigen retrieval buffer and washing the biological sample.

In some embodiments, optimizing permeabilization can be useful for identifying intracellular analytes. Permeabilization optimization can include selection of permeabilization agents, concentration of permeabilization agents, and permeabilization duration. Tissue permeabilization is discussed elsewhere herein.

In some embodiments, blocking an array and/or a biological sample in preparation of labeling the biological sample decreases nonspecific binding of the antibodies to the array and/or biological sample (decreases background). Some embodiments provide for blocking buffers/blocking solutions that can be applied before and/or during application of the label, wherein the blocking buffer can include a blocking agent, and optionally a surfactant and/or a salt solution. In some embodiments, a blocking agent can be bovine serum albumin (BSA), serum, gelatin (e.g., fish gelatin), milk (e.g., non-fat dry milk), casein, polyethylene glycol (PEG), polyvinyl alcohol (PVA), or polyvinylpyrrolidone (PVP), biotin blocking reagent, a peroxidase blocking reagent, levamisole, Carnoy's solution, glycine, lysine, sodium borohydride, pontamine sky blue, Sudan Black, trypan blue, FITC blocking agent, and/or acetic acid. The blocking buffer/blocking solution can be applied to the array and/or biological sample prior to and/or during labeling (e.g., application of fluorophore-conjugated antibodies) to the biological sample.

(iii) Preparation of Sample for Application of Probes

In some instances, additional reagents are added to the biological sample, prior to the addition of the probes. Additional reagents can be any reagent known in the art, so long as it preserves the integrity of an analyte.

In some instances, the biological sample is deparaffinized. Deparaffinization can be achieved using any method known in the art. For example, in some instances, the biological sample is treated with a series of washes that include xylene and various concentrations of ethanol. In some instances, methods of deparaffinization include treatment with xylene (e.g., three washes at 5 minutes each). In some instances, the methods further include treatment with ethanol (e.g., 100% ethanol, two washes 10 minutes each; 95% ethanol, two washes 10 minutes each; 70% ethanol, two washes 10 minutes each; 50% ethanol, two washes 10 minutes each). In some instances, after ethanol washes, the biological sample can be washed with deionized water (e.g., two washes for 5 minutes each). It is appreciated that one skilled in the art can adjust these methods to optimize deparaffinization.

In some instances, the biological sample is decrosslinked. In some instances, the biological sample is decrosslinked in a solution containing TE buffer (comprising Tris and EDTA). In some instances, the TE buffer is basic (e.g., at a pH of about 9). In some instances, decrosslinking occurs at about 50° C. to about 80° C. In some instances, decrosslinking occurs at about 70° C. In some instances, decrosslinking occurs for about 1 hour at 70° C. Just prior to decrosslinking, the biological sample can be treated with an acid (e.g., 0.1M HCl for about 1 minute). After the decrosslinking step, the biological sample can be washed (e.g., with 1×PBST).

In some instances, the methods of preparing a biological sample for probe application include permeabilizing the sample. In some instances, the biological sample is permeabilized using a phosphate buffer. In some instances, the phosphate buffer is PBS (e.g., 1×PBS). In some instances, the phosphate buffer is PBST (e.g., 1×PBST). In some instances, the permeabilization step is performed multiple times (e.g., 3 times at 5 minutes each).

In some embodiments of any of the methods for identifying a location of an analyte in a biological sample, the method includes permeabilizing (e.g., using any of the exemplary permeabilization methods described herein) the biological sample before, contemporaneously with, or after exposing the biological sample to the capture probe. In some embodiments of any of the methods for identifying a location of an analyte in a biological sample, the method includes processing the biological sample using any of the methods described herein. For example, the method can include selecting a region of interest of the biological sample by laser-capture microdissection prior to exposing the biological sample to the capture probe.

In some instances, the methods of preparing a biological sample for probe application include steps of equilibrating and blocking the biological sample. In some instances, equilibrating is performed using a pre-hybridization (pre-Hyb) buffer. In some instances, the pre-Hyb buffer is RNase-free. In some instances, the pre-Hyb buffer contains no bovine serum albumin (BSA), solutions like Denhardt's, or other potentially nuclease-contaminated biological materials.

In some instances, the equilibrating step is performed multiple times (e.g., 2 times at 5 minutes each; 3 times at 5 minutes each). In some instances, the biological sample is blocked with a blocking buffer. In some instances, the blocking buffer includes a carrier such as tRNA, for example yeast tRNA (e.g., at a final concentration of 10-20 μg/mL). In some instances, blocking can be performed for 5, 10, 15, 20, 25, or 30 minutes.

Any of the foregoing steps can be optimized for performance. For example, one can vary the temperature. In some instances, the pre-hybridization methods are performed at room temperature. In some instances, the pre-hybridization methods are performed at 4° C. (in some instances, varying the timeframes provided herein).

(h) Substrates and Capture Probes

This disclosure features a method of identifying a location of an analyte in a biological sample using a substrate that includes a plurality of capture probes, where a capture probe of the plurality of capture probes includes a capture domain. In some embodiments, the capture probe does not include a spatial barcode. In some embodiments, the capture probe includes a spatial barcode.

In some embodiments, a capture probe of the plurality of capture probes is affixed to the substrate at the 5' end of the capture probe. In such cases, in order to prevent extension of the capture probe during the amplifying step, the capture probe includes a blocking moiety on the 3' end. Blocking or modifying the capture probes, particularly at the free 3' end of the capture domain, prior to contacting the biological sample with the array, prevents (1) modification of the capture probes, e.g., prevents the addition of a poly(A) tail to the free 3' end of the capture probes and (2) extension of the capture probe during amplification of the circularized padlock probe or snail probe.

In some embodiments, the ability to prevent capture probe extension is temporary (e.g., blocking extension of the capture probe during the amplifying step but allowing extension during, for example, a step that purposely extends the capture probe). In such cases, the blocking moiety on the 3' end can be removed and the capture probe can be extended. For example, the method can include a reversible blocking moiety on the 3' end of the capture probe in a blocking position during amplification but in a non-blocking position (e.g., removed by cleavage) during a capture probe extension step.

In some embodiments where a capture probe of the plurality of capture probes is attached to the substrate at the 5' end, the capture probe is blocked at the 3' end. In some embodiments, the capture probes can be reversibly masked or modified such that the capture domain of the capture probe does not include a free 3' end. In some embodiments, the 3' end is removed, modified, or made inaccessible so that the capture domain is not susceptible to the process used to modify the nucleic acid of the biological sample, e.g., ligation or extension. A capture probe can be blocked at the 3' end by a blocking moiety. The blocking moiety can be a reversible blocking moiety. In some cases, the 3' end of the capture probe includes a removable hairpin. In some cases, the 3' end includes a 3' blocking group present on the sugar moiety of the nucleotide at the 3' end. In such cases, the 3' blocking group can be chemically removed from the nucleic acid.

In some embodiments, the free 3' end of the capture domain can be blocked by chemical modification, e.g., addition of an azidomethyl group as a chemically reversible capping moiety such that the capture probes do not include a free 3' end. Non-limiting examples of 3' modifications include dideoxy C-3' (3'-ddC), 3' inverted dT, 3' C3 spacer, 3'Amino, and 3' phosphorylation.

In some embodiments where a capture probe of the plurality of capture probes is attached to the substrate at the 5' end and the 3' is blocked, additional nucleotides are added to the 3' end in order to reveal and/or restore the blocked 3' end of the capture probe, thereby creating a free 3' end.

In some embodiments, the capture domain includes a sequence that is at least partially complementary to the analyte or the analyte derived molecule. In some embodiments, the capture domain of the capture probe includes a poly-dT sequence. In some embodiments, the capture domain of the capture probe includes a sequence complementary to an analyte of interest (e.g., Secretoglobin Family 1A Member 1 (scgb1a1) or hippocalcin (HPCA),).

In some embodiments, the capture domain includes a functional domain. In some embodiments, the functional domain includes a primer sequence. In some embodiments, the capture probe includes a cleavage domain. In some embodiments, the cleavage domain includes a cleavable linker from the group consisting of a photocleavable linker, a UV-cleavable linker, an enzyme-cleavable linker, or a pH-sensitive cleavable linker.

In some embodiments, the capture domain of the capture probe comprises a non-homopolymeric sequence. In some embodiments, the capture domain is a defined sequence. In such cases, the defined sequence can be substantially complementary to a portion of the amplified padlock probe or snail probe. When the capture probe is substantially complementary to a portion of the amplified oligonucleotide, the capture domain can be used to capture all or a portion of the padlock probe or snail probe. In some instances, a defined sequence is about 5 to 50 nucleotides in length (e.g., about 5 to 25, about 5 to 20, about 10 to 25, about 10 to 20). In some instances, the length of the defined sequence is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides long. Defined sequences can include natural or synthetic nucleic acids. It is appreciated that a skilled artisan can design the defined sequence in order to capture a particular target or particular targets of interest.

In preferred embodiments the capture probe is blocked on the 3' end using any blocking method as previously described. The analyte or analyte derived molecule is captured by the capture domain of the capture probe, padlock probes or snail probes are hybridized and circularized and RCA performed, and detection of the analyte or analyte derived molecule determined via one or more detection probes. In this particular embodiment, a blocked capture probe mitigates any modification or extension of the capture probe during amplification of the circularized padlock probe or snail probe.

(i) Methods of Performing RNA Analysis on a Related Biological Sample

In some embodiments, after determining the mislocalization of analytes in a biological sample, RNA analysis can be performed on a related biological sample (e.g., a serial biological section) using a spatial array. In some instances, the related biological sample, for example a serial section taken from a tissue block that was used to determine mislocalization of analytes, is placed on a second substrate and analytes are captured using methods disclosed herein. The methods include determining abundance and/or location of a plurality of analytes in a related biological sample. In some examples, determining the abundance and/or location includes: (a) contacting a second spatial array comprising a comprising a plurality of second spatial capture probes with the related (e.g., serial) biological section, wherein a second spatial capture probe of the plurality of second spatial capture probes comprises a second spatial barcode and a second capture domain, (b) hybridizing an analyte from the related (e.g., serial) biological section to a second capture domain, and (c) determining: (i) all or a part of a sequence of the analyte from the related (e.g., serial) biological section, or a complement thereof, and (ii) the sequence of the second spatial barcode, or a complement thereof, and using the determined sequence of (i) and (ii) to determine the abundance and/or the location of the analyte from the serial biological section.

The methods of RNA analysis include preparation of the related biological sample, which includes but is not limited to sectioning the sample, staining and deparaffinizing the sample, imaging the sample, and permeabilizing the sample. In some instances, permeabilization includes treatment with a solution comprising proteinase K, pepsin, or a combination of both. Preparation of biological samples is disclosed in WO 2020/176788 and/or U.S. Patent Application Publication No. 2020/0277663, each of which is incorporated by reference in its entirety.

In some instances, analytes are captured by capture probes on the second spatial array. After an analyte from the sample has hybridized or otherwise been associated with a capture probe according to any of the methods described above in connection with the general spatial cell-based analytical methodology, the barcoded constructs that result from hybridization/association are analyzed.

In some embodiments, after contacting a biological sample with a substrate that includes capture probes, a removal step can optionally be performed to remove all or a portion of the biological sample from the substrate. In some embodiments, the removal step includes enzymatic and/or chemical degradation of cells of the biological sample. For example, the removal step can include treating the biological sample with an enzyme (e.g., a proteinase, e.g., proteinase K) to remove all or at least a portion of the biological sample from the substrate. In some embodiments, the removal step can include ablation of the tissue (e.g., laser ablation).

In some embodiments, provided herein are methods for spatially detecting an analyte (e.g., detecting the location of an analyte, e.g., a biological analyte) from a biological sample (e.g., present in a biological sample), the method comprising: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; wherein the biological sample is fully or partially removed from the substrate.

In some embodiments, a biological sample is not removed from the substrate. For example, the biological sample is not removed from the substrate prior to releasing a capture probe (e.g., a capture probe bound to an analyte) from the substrate. In some embodiments, such releasing comprises cleavage of the capture probe from the substrate (e.g., via a cleavage domain). In some embodiments, such releasing does not comprise releasing the capture probe from the substrate (e.g., a copy of the capture probe bound to an analyte can be made and the copy can be released from the substrate, e.g., via denaturation). In some embodiments, the biological sample is not removed from the substrate prior to analysis of an analyte bound to a capture probe after it is released from the substrate. In some embodiments, the biological sample remains on the substrate during removal of a capture probe from the substrate and/or analysis of an analyte bound to the capture probe after it is released from the substrate. In some embodiments, the biological sample remains on the substrate during removal (e.g., via denaturation) of a copy of the capture probe (e.g., complement). In some embodiments, analysis of an analyte bound to capture probe from the substrate can be performed without subjecting the biological sample to enzymatic and/or chemical degradation of the cells (e.g., permeabilized cells) or ablation of the tissue (e.g., laser ablation).

In some embodiments, at least a portion of the biological sample is not removed from the substrate. For example, a portion of the biological sample can remain on the substrate prior to releasing a capture probe (e.g., a capture probe bound to an analyte) from the substrate and/or analyzing an analyte bound to a capture probe released from the substrate. In some embodiments, at least a portion of the biological sample is not subjected to enzymatic and/or chemical degradation of the cells (e.g., permeabilized cells) or ablation of the tissue (e.g., laser ablation) prior to analysis of an analyte bound to a capture probe from the substrate.

In some embodiments, provided herein are methods for spatially detecting an analyte (e.g., detecting the location of an analyte, e.g., a biological analyte) from a biological sample (e.g., present in a biological sample) that include: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; where the biological sample is not removed from the substrate.

In some embodiments, provided herein are methods for spatially detecting a biological analyte of interest from a biological sample that include: (a) staining and imaging a biological sample on a substrate; (b) providing a solution comprising a permeabilization reagent to the biological sample on the substrate; (c) contacting the biological sample with an array on a substrate, wherein the array comprises one or more capture probe pluralities thereby allowing the one or more pluralities of capture probes to capture the biological analyte of interest; and (d) analyzing the captured biological analyte, thereby spatially detecting the biological analyte of interest; where the biological sample is not removed from the substrate.

In some embodiments, the method further includes subjecting a region of interest in the biological sample to spatial transcriptomic analysis. In some embodiments, one or more of the capture probes includes a capture domain. In some embodiments, one or more of the capture probes comprises a unique molecular identifier (UMI). In some embodiments, one or more of the capture probes comprises a cleavage domain. In some embodiments, the cleavage domain comprises a sequence recognized and cleaved by a uracil-DNA glycosylase, apurinic/apyrimidinic (AP) endonuclease (APE1), U uracil-specific excision reagent (USER), and/or an endonuclease VIII. In some embodiments, one or more capture probes do not comprise a cleavage domain and is not cleaved from the array.

In some embodiments, a capture probe can be extended (an "extended capture probe," e.g., as described herein). For example, extending a capture probe can include generating cDNA from a captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending a capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, a capture domain of a capture probe includes a primer for producing the complementary strand of a nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA (e.g., cDNA) molecule is generated. In some embodiments, a "full-length"

DNA molecule refers to the whole of the captured nucleic acid molecule. However, if a nucleic acid (e.g., RNA) was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Lucigen, Middleton, WI). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9°N) DNA ligase (9°N™ DNA ligase, New England Biolabs), Ampligase™ (available from Lucigen, Middleton, WI), and SplintR (available from New England Biolabs, Ipswich, MA). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g., sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to a substrate specific for the affinity group. In some embodiments, the substrate can include an antibody or antibody fragment. In some embodiments, the substrate includes avidin or streptavidin and the affinity group includes biotin. In some embodiments, the substrate includes maltose and the affinity group includes maltose-binding protein. In some embodiments, the substrate includes maltose-binding protein and the affinity group includes maltose. In some embodiments, amplifying the extended capture probes can function to release the extended probes from the surface of the substrate, insofar as copies of the extended probes are not immobilized on the substrate.

In some embodiments, the extended capture probe or complement or amplicon thereof is released. The step of releasing the extended capture probe or complement or amplicon thereof from the surface of the substrate can be achieved in a number of ways. In some embodiments, an extended capture probe or a complement thereof is released from the array by nucleic acid cleavage and/or by denaturation (e.g., by heating to denature a double-stranded molecule).

In some embodiments, the extended capture probe, complement, or amplicon thereof is released from the surface of the substrate (e.g., array) by physical means. For example, where the extended capture probe is indirectly immobilized on the array substrate, e.g., via hybridization to a surface probe, it can be sufficient to disrupt the interaction between the extended capture probe and the surface probe. Methods for disrupting the interaction between nucleic acid molecules include denaturing double stranded nucleic acid molecules are known in the art. A straightforward method for releasing the DNA molecules (i.e., of stripping the array of extended probes) is to use a solution that interferes with the hydrogen bonds of the double stranded molecules. In some embodiments, the extended capture probe is released by an applying heated solution, such as water or buffer, of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the substrate.

In some embodiments, where the extended capture probe includes a cleavage domain, the extended capture probe is released from the surface of the substrate by cleavage. For example, the cleavage domain of the extended capture probe can be cleaved by any of the methods described herein. In some embodiments, the extended capture probe is released from the surface of the substrate, e.g., via cleavage of a cleavage domain in the extended capture probe, prior to the step of amplifying the extended capture probe.

In some embodiments, probes complementary to the extended capture probe can be contacted with the substrate. In some embodiments, the biological sample can be in contact with the substrate when the probes are contacted with the substrate. In some embodiments, the biological sample can be removed from the substrate prior to contacting the substrate with probes. In some embodiments, the probes can be labeled with a detectable label (e.g., any of the detectable labels described herein). In some embodiments, probes that do not specially bind (e.g., hybridize) to an extended capture probe can be washed away. In some embodiments, probes complementary to the extended capture probe can be detected on the substrate (e.g., imaging, any of the detection methods described herein).

In some embodiments, probes complementary to an extended capture probe can be about 4 nucleotides to about 100 nucleotides long. In some embodiments, probes (e.g., detectable probes) complementary to an extended capture probe can be about 10 nucleotides to about 90 nucleotides long. In some embodiments, probes (e.g., detectable probes) complementary to an extended capture probe can be about 20 nucleotides to about 80 nucleotides long. In some embodiments, probes (e.g., detectable probes) complementary to an extended capture probe can be about 30 nucleotides to about 60 nucleotides long. In some embodiments, probes (e.g., detectable probes) complementary to an extended capture probe can be about 40 nucleotides to about 50 nucleotides long. In some embodiments, probes (e.g., detectable probes) complementary to an extended capture probe can be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 nucleotides long.

In some embodiments, about 1 to about 100 probes can be contacted to the substrate and specifically bind (e.g., hybridize) to an extended capture probe. In some embodiments, about 1 to about 10 probes can be contacted to the substrate and specifically bind (e.g., hybridize) to an extended capture probe. In some embodiments, about 10 to about 100 probes can be contacted to the substrate and specifically bind (e.g., hybridize) to an extended capture probe. In some embodiments, about 20 to about 90 probes can be contacted to the substrate and specifically bind (e.g., hybridize) to an extended capture probe. In some embodiments, about 30 to about 80 probes (e.g., detectable probes) can be contacted to the substrate and specifically bind (e.g., hybridize) to an extended capture probe. In some embodiments, about 40 to about 70 probes can be contacted to the substrate and specifically bind (e.g., hybridize) to an extended capture probe. In some embodiments, about 50 to about 60 probes can be contacted to the substrate and specifically bind (e.g., hybridize) to an extended capture probe. In some embodiments, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 probes can be contacted to the substrate and specifically bind (e.g., hybridize) to an extended capture probe.

In some embodiments, the probes can be complementary to a single analyte (e.g., a single gene). In some embodiments, the probes can be complementary to one or more analytes (e.g., analytes in a family of genes). In some embodiments, the probes (e.g., detectable probes) can be for a panel of genes associated with a disease (e.g., cancer, Alzheimer's disease, Parkinson's disease).

In some instances, the analyte and capture probe can be amplified or copied, creating a plurality of cDNA molecules. In some embodiments, cDNA can be denatured from the capture probe template and transferred (e.g., to a clean tube) for amplification, and/or library construction. The spatially-barcoded cDNA can be amplified via PCR prior to library construction. The cDNA can then be enzymatically fragmented and size-selected in order to optimize for cDNA amplicon size. P5 and P7 sequences directed to capturing the amplicons on a sequencing flowcell (Illumina sequencing instruments) can be appended to the amplicons, i7, and i5 can be used as sample indexes, and TruSeq Read 2 can be added via End Repair, A-tailing, Adaptor Ligation, and PCR. The cDNA fragments can then be sequenced using paired-end sequencing using TruSeq Read 1 and TruSeq Read 2 as sequencing primer sites. The additional sequences are directed toward Illumina sequencing instruments or sequencing instruments that utilize those sequences; however a skilled artisan will understand that additional or alternative sequences used by other sequencing instruments or technologies are also equally applicable for use in the aforementioned methods.

In some embodiments, where a sample is barcoded directly via hybridization with capture probes or analyte capture agents hybridized, bound, or associated with either the cell surface, or introduced into the cell, as described above, sequencing can be performed on the intact sample.

A wide variety of different sequencing methods can be used to analyze barcoded analyte. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based single plex methods, emulsion PCR), and/or isothermal amplification. Non-limiting examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods.

(j) Kits

In some instances, disclosed herein are compositions and systems that are used to carry out the methods described herein. In some embodiments, the kit includes a padlock probe or snail probe and a ligase (e.g., a T4 DNA ligase (Rnl2), a SplintR ligase, a single stranded DNA ligase, or a T4 DNA ligase). In some embodiments, the kit further includes one or more primers (e.g., two or more primers, three or more primers, four or more primers, five or more primers, six or more primers, seven or more primers, eight or more primers, nine or more primers, or ten or more primers) and a polymerase (e.g., a Phi29 DNA polymerase or other strand displacing polymerase).

In some embodiments, the kit further includes a substrate including a plurality of capture probes, where a capture probe of the plurality capture probes includes a capture domain, wherein the analyte is capable of hybridizing to the capture domain. In some embodiments, the kit includes a substrate including a plurality of capture probes, where a capture probe of the plurality of capture probes includes a capture domain and a spatial barcode. In some instances, the capture probe is specific to a target analyte. In some instances, the target analyte is Scgb1a1. In some instances, the target analyte is HPCA. It is appreciated that the kit can include any of the elements of the substrate, array, or capture probes as described herein.

In some embodiments, the kit further includes a plurality of detection probes, wherein a detection probe from the plurality of detection probes comprises a sequence that is substantially complementary to a sequence of the padlock probe or snail probe and a detectable label (e.g., any of the exemplary detectable labels described herein (e.g., a fluorophore)).

In some embodiments, a kit used to carry out the methods described herein includes:
(a) one or more padlock probes or snail probes and a ligase; (b) one or more primers and a polymerase;
(c) a substrate including a plurality of capture probes, wherein a capture probe of the plurality of capture probes includes a capture domain; and (d) instructions for performing the methods described herein.

In some embodiments, a kit used to carry out the methods described herein includes: (a) one or more padlock probes or snail probes and a ligase; (b) one or more primers and a polymerase; (c) a substrate including a plurality of capture probes, wherein a capture probe of the plurality of capture probes includes a capture domain; (d) one or more fluorescent dyes and/or one or more detection probes; and (e) instructions for performing the methods described herein.

In some embodiments, a kit used to carry out the methods described herein includes: (a) one or more padlock probes or snail probes and a ligase; (b) one or more primers and a polymerase; (c) a substrate including a plurality of capture probes, wherein a capture probe of the plurality of capture probes includes a capture domain; (d) one or more fluorescent dyes and/or one or more detection probes; (e) a uracil-DNA glycosylase enzyme; and (f) instructions for performing the methods described herein.

EXAMPLES

Example 1—Method for Determining the Mislocalization of an Analyte Using RCA

This example provides a method of identifying the mislocalization of an analyte (e.g., an mRNA molecule) in a biological sample (e.g., a fresh frozen tissue section) where the mRNA molecule is hybridized to a capture domain of a capture probe and the capture probe is extended using the mRNA as a template for extension. As an overview, prior to mRNA capture, the sample is stained using H&E, immunofluorescence, or immunohistochemistry. Then, the sample is imaged to provide a first image (also referred to as a "ground truth" or "baseline reference" image). After imaging, analytes (e.g., mRNA transcripts) are captured on an array comprising capture probes. The capture probe is extended using a polymerase (e.g., a reverse transcriptase) and one or more fluorescently labelled dNTPs maybe optionally incorporated into the extension product. After generating the extended capture probe, KOH is added to remove the mRNA molecule, and then either a padlock probe or a snail probe is hybridized to the extended capture probe.

The hybridized padlock probe or snail probe is ligated (e.g., using T4 DNA ligase), and the padlock probe or snail probe is amplified using rolling circle amplification (RCA) (e.g., using phi29 DNA polymerase) and a signal (e.g., fluorescence) corresponding to the amplified RCA product (e.g., microscopy puncta) is detected using labeled detection probes. A second image of the biological sample is taken to quantify and/or quantitate the signal from the detection probes hybridized to the RCA product. Comparing the first (ground truth) image to the second image after RCA product detection, one can determine the distance of mislocalization of the analyte during analyte capture on the array.

The assay further allows determination of analyte mislocalization rates as various experimental parameters are altered. For instance, permeabilization time (e.g., 0-30 minutes), permeabilization enzymes and/or concentrations, permeabilization temperature (e.g., room temperature; 37° C.), and tissue section thickness can be altered, and the effect of each experimental parameter on analyte mislocalization can be calculated.

Figure 7A:
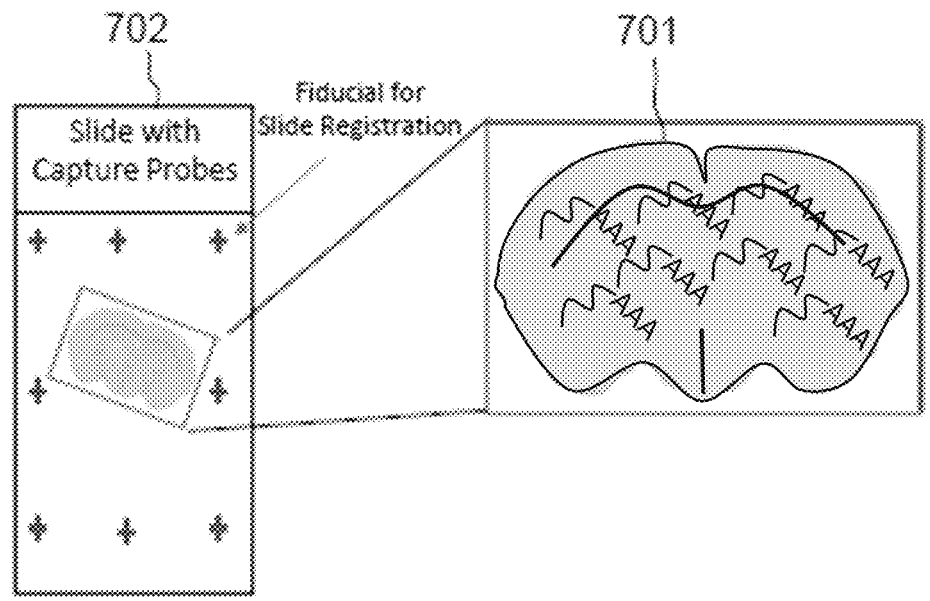
FIG. 7A is a schematic diagram of an exemplary substrate 702 and biological sample 701.
Figure 7B:
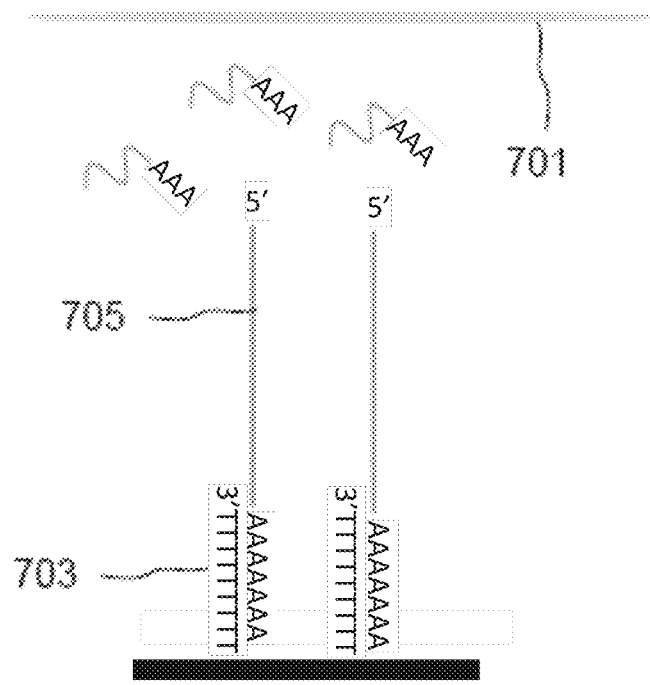
FIG. 7B is a schematic illustrating a cross-sectional view of the exemplary substrate having capture probes 703 and biological sample 701 having analytes 705 in FIG. 7A.

As shown in FIGS. 7A-7B, a biological sample 701 is contacted with a substrate 702 including a plurality of capture probes, where each capture probe includes a capture domain (in this example, a poly-dT sequence 703). In some instances, the probe is specific for a target such as Scgb1a1 or HPCA or any other desired target. The biological sample is permeabilized and the mRNA molecules are released from the biological sample. In particular, after 30 minutes the tissue is washed and permeabilized by adding various concentrations of proteinase K (e.g., 1 mg/ml; 1.25 mg/ml; 1.5 mg/ml Proteinase K), incubated at various temperatures (e.g., room temperature; 37° C.) for various times (e.g., 1 minute; 5 minutes; 10 minutes; 20 minutes; 30 minutes). After, the samples are washed to remove the protease. The released mRNA molecules 705 are allowed to hybridize to the capture domain on the capture probe 703 immobilized on the array via the polyadenylated tail on the 3' end of the mRNA molecule. Excess mRNA molecules not hybridized to a capture probe are washed off.

The mRNA hybridized to the capture probe is contacted with a padlock probe or a snail probe under conditions that allow the padlock probe or snail probe to hybridize to the extended capture probe.

Figure 8A:
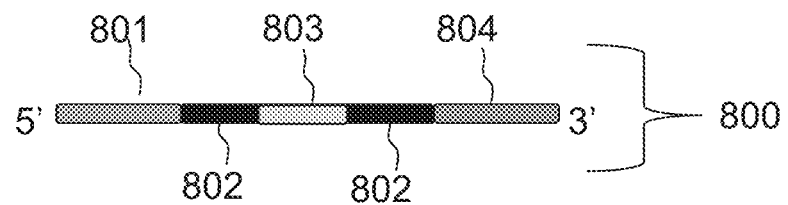
FIG. 8A is a schematic diagram of an exemplary padlock oligonucleotide 800.
Figure 8B:
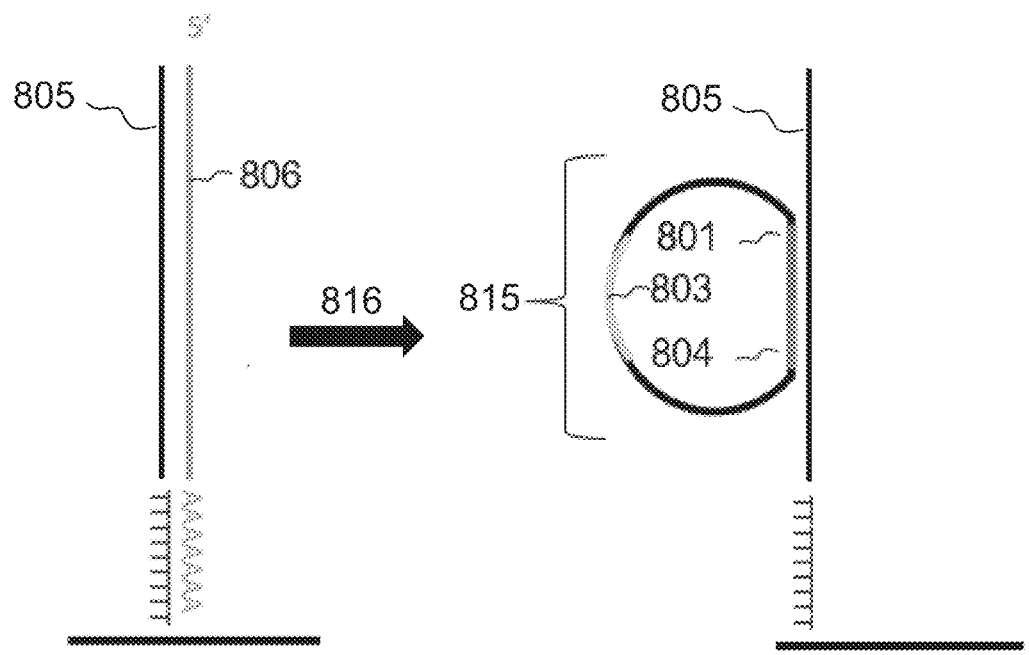
FIG. 8B is a schematic diagram of an exemplary padlock oligonucleotide 815 hybridized to an extended capture probe 805 bound to a substrate.

As a brief overview, a padlock probe (800 in FIG. 8A) or snail probe is hybridized to an extended capture probe molecule 815 in FIG. 8B. In some instances, a snail probe is tethered to the capture probe in order to retain the spatial location of any subsequent amplification product. The padlock probe or snail probe is ligated to create a circularized padlock probe or a circularized snail probe and amplified using RCA 810 in FIG. 8D. The amplified circularized padlock probe or snail probe is contacted with a plurality of detection probes 811 in FIG. 8E. The sample (e.g., a tissue section) is imaged (e.g., brightfield imaging to detect H&E stain; fluorescent stain for a protein marker). For example, an analyte can be associated with a stain (e.g., H&E; immunofluorescence), allowing a user to identify where the analyte is found in the biological sample.

More particularly, in some instances, the sample is decrosslinked to remove formaldehyde crosslinks within the sample thereby releasing mRNA molecules from the sample. Briefly, the tissue samples are incubated with an HCl solution for 1 minute, repeated twice for a total of 3 minutes. Following HCl incubations, the tissue sections are incubated at 70° C. for 1 hour in TE pH 9.0. TE is removed and the tissues are incubated in 1×PBS-Tween for 15 minutes.

As shown in FIG. 8A, a padlock probe 800 (or a snail probe) includes a first sequence 801 that is substantially complementary to a first portion of the extended capture probe 805, a backbone sequence 802 that includes a barcode sequence 803, and a second sequence 804 that is substantially complementary to a second portion of the extended capture probe. After capture of an analyte (e.g., mRNA molecule) 705 in FIG. 7B, the capture probe 703 (as shown in FIG. 7B) is extended using reverse transcriptase and the analyte as a template, thereby generating an extended capture probe 805. The padlock probe 800 or snail probe is added to the substrate and hybridizes to the extended capture probe 805. In this example, the first sequence and second sequence are adjacent when hybridized to the extended capture probe 805. As a result, as shown in FIG. 8B, the second sequence 804 can be directly ligated to the first sequence 801, thereby creating a circularized padlock probe 815 or snail probe.

Figures 8C, 8D:
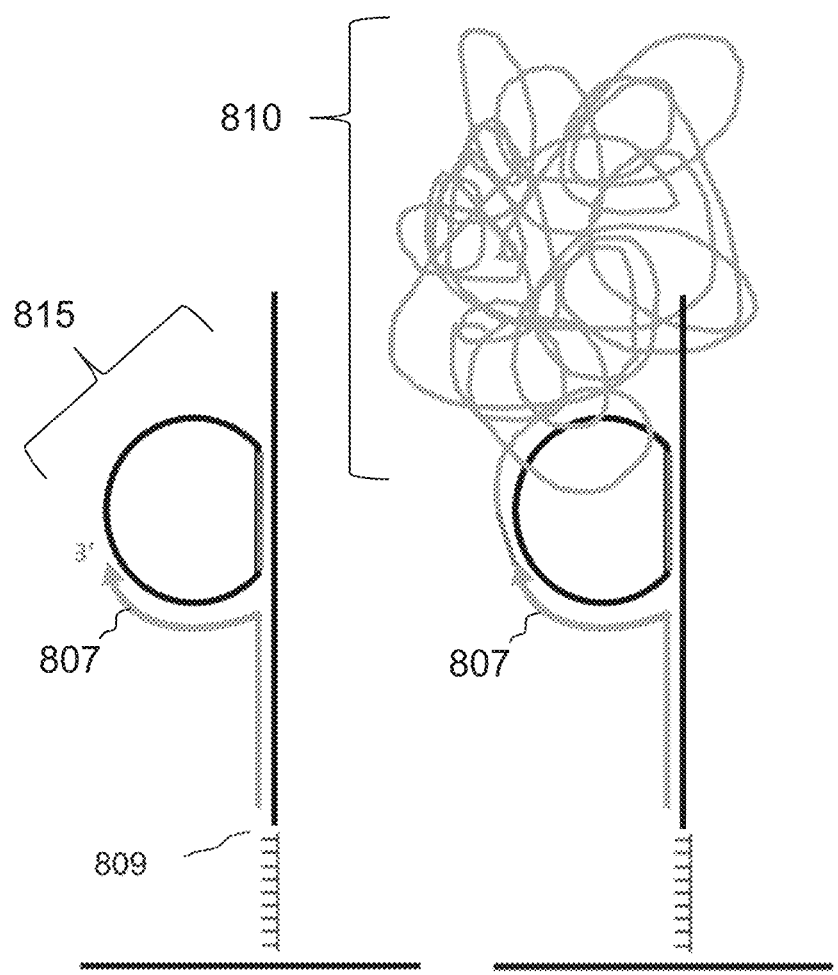
FIG. 8C is a schematic diagram of an exemplary primer 807 hybridized to an exemplary circularized padlock oligonucleotide 815.
FIG. 8D is a schematic illustrating the product 810 of a rolling circle amplification reaction (i.e., amplified circularized padlock oligonucleotide).

As shown in FIG. 8C, following circularization of the padlock probe or snail probe, a primer 807 is hybridized to the circularized padlock probe 815 or snail probe. The primer 807 includes a sequence that is substantially complementary to the circularized padlock probe or snail probe and, in some instances, a sequence that is substantially complementary to the extended capture probe. In some embodiments, the primer 807 is ligated 809 to the free 3' end of the capture probe. Rolling circle amplification (RCA), as shown in FIG. 8D, is used to amplify the circularized padlock probe 815 or snail probe using a Phi29 DNA polymerase. In some instances, the amplified circularized padlock probe 810 or snail probe remains tethered to the extended capture probe where the continuous single-stranded copies produced by RCA remains associated with the location on the substrate via the tether to the extended capture probe. In other embodiments, no snail probe is used, and amplification proceeds using the circularized padlock probe 810 as shown in FIG. 8E.

Figure 8E:
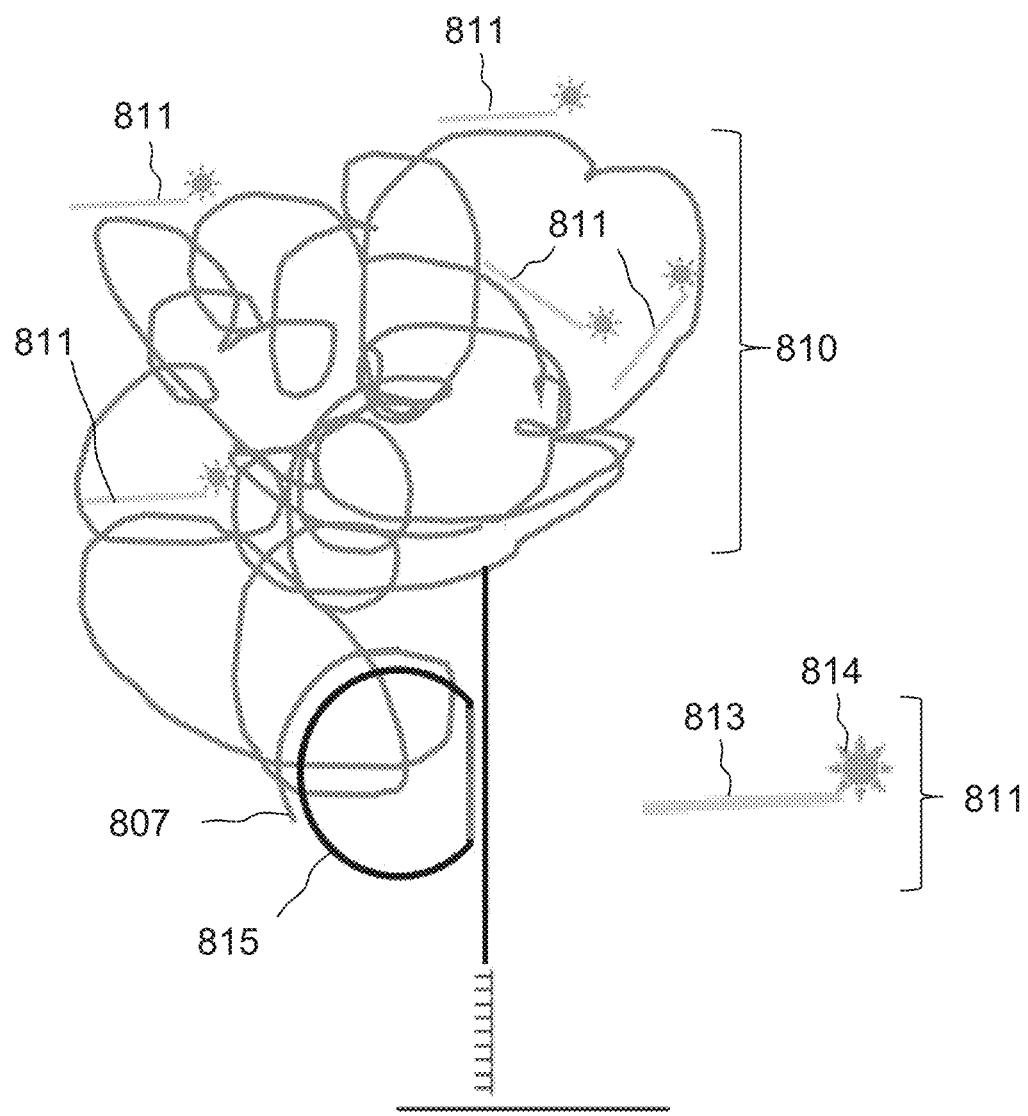
FIG. 8E is a schematic showing a plurality of detection probes 811 bound to multiple regions of the amplified circularized padlock oligonucleotide 810.

After amplification, labeled detection probes are used as a proxy to detect the analyte 811 in FIG. 8E. As shown in FIG. 8E, the continuous single-stranded copies (e.g., amplified circularized padlock probe or snail probe) of the circularized padlock probe 810 or snail probe produced by RCA are contacted with a plurality of detection probes 811, wherein a detection probe 811 includes a sequence 813 that is substantially complementary to a sequence of the padlock probe or snail probe and a fluorophore 814. Fluorescent detection of the fluorophore can be measured and the distance of the fluorescent label as compared to the analyte's original position in the biological sample can be mapped to the first image taken prior to analyte capture (i.e., the ground truth H&E or IF image).

Figure 9:
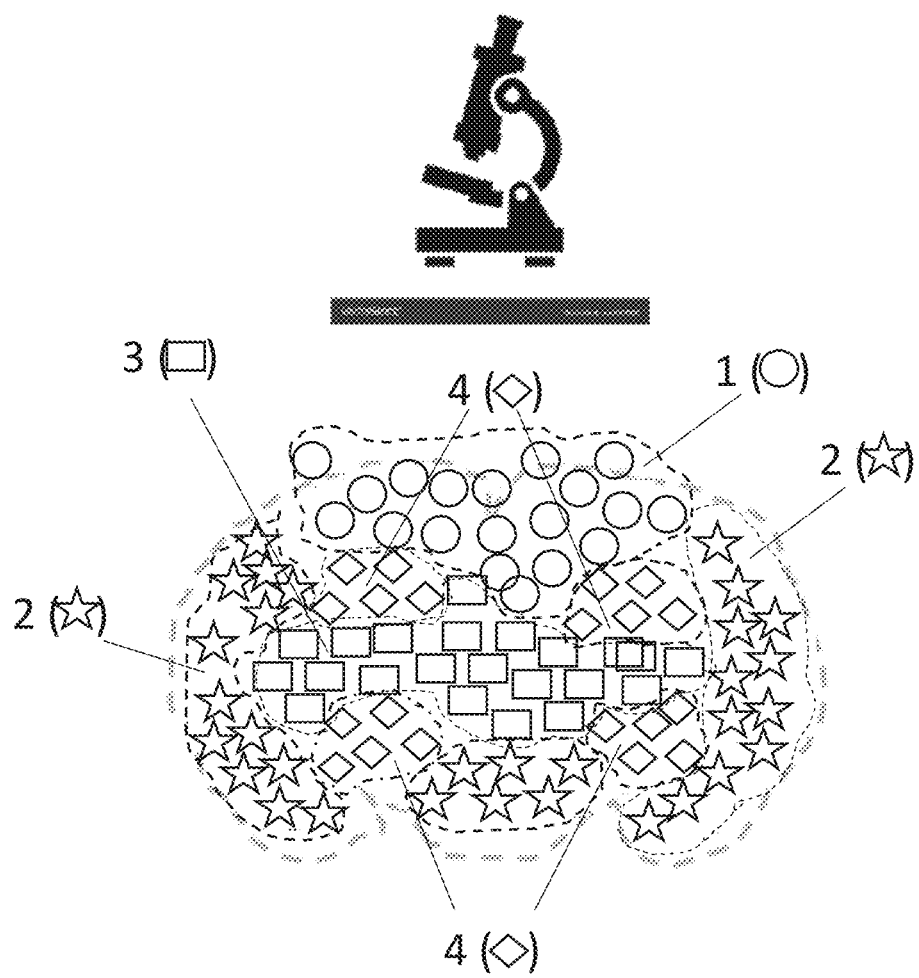
FIG. 9 is a schematic illustrating detected signal from a plurality of amplified circularized padlock oligonucleotides shown as regions 1 (circles), 2 (stars), 3 (rectangles), and 4 (diamonds).

FIG. 9 shows the detected signals from a plurality of amplified circularized padlock probes or snail probe on the substrate, each numerical area (1 through 4) representing a different analyte or analyte derived molecule (each area is indicated by a dotted line and a corresponding numeral and shape). The optimal parameters for a specific tissue are determined based on identifying the experimental conditions giving rise to lowest or minimalist amount of analyte mislocalization (i.e., where the detection probe signal (e.g., from the second image) and the first image of the analyte (e.g., H&E stain) substantially overlap.

Figure 10:
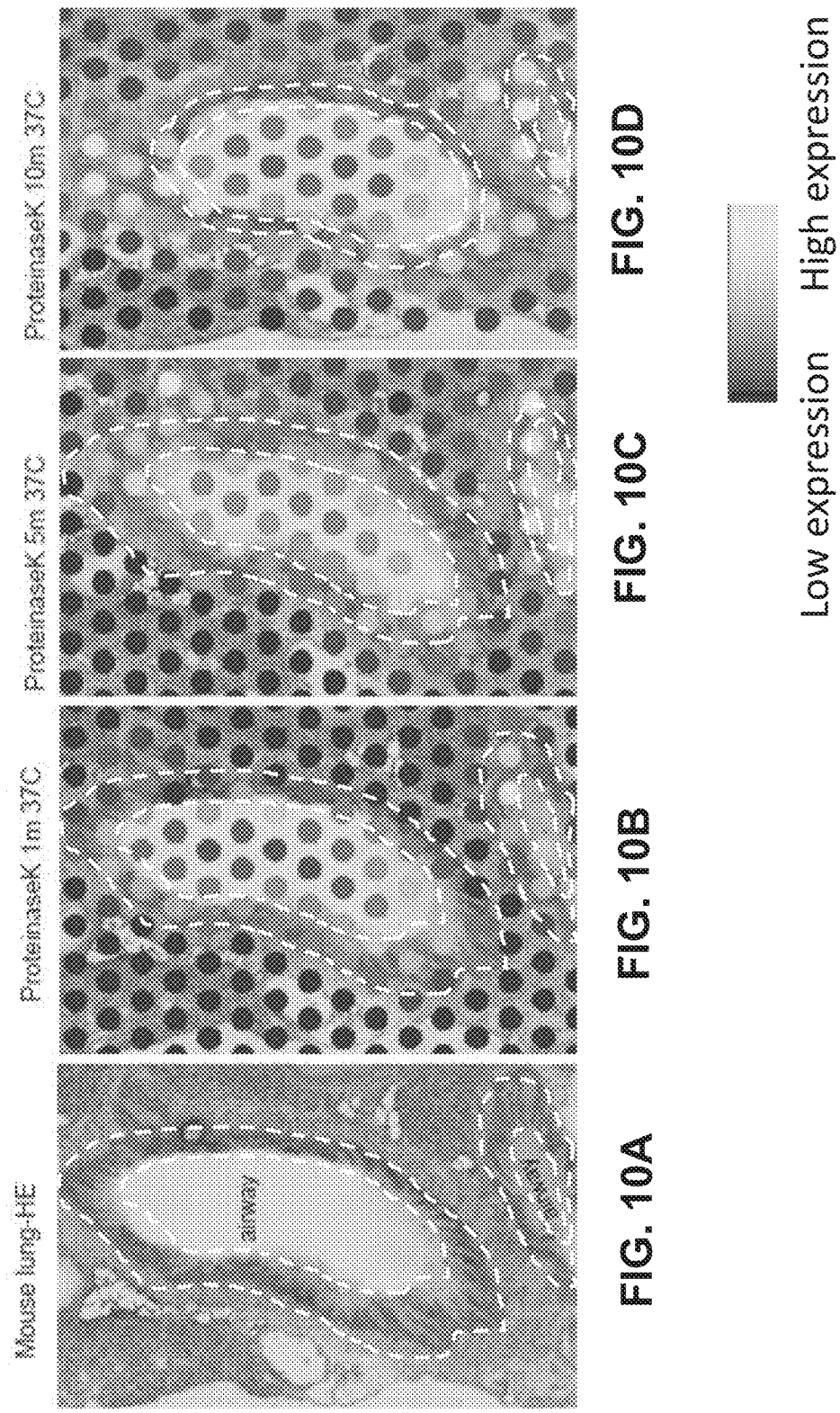
FIGS. 10A-10D show gene expression heat maps for Scgb1a1 across serial mouse lung tissue sections following different permeabilization conditions.

An example of mRNA transcript mislocalization is shown in FIGS. 10A-10D, which shows a gene expression heat map of Scgb1a1 mRNA molecules following different permeabilization times. Scgb1a1 is expressed only in the cells lining the airway of mouse lung (see FIGS. 12D and 12E). Here, a mouse lung tissue section was permeabilized using proteinase K at 37° C. for 1 minute, 5 minute, or 10 minutes. Referring to FIGS. 10B-10D, the gene expression heat maps showed that Scgb1a1 transcripts mislocalized from their predicted locations (i.e., diffused away from the cells lining the lung airway) within the biological sample and that the amount of mislocalization (e.g., distance travelled from its predicted location) correlated with permeabilization time, where increased permeabilization time resulted in increased analyte mislocalization. For example, in FIG. 10D there are multiple gene expression data points (green dots) having elevated gene expression at positions distal to cells lining the lung airway. In comparison, similar levels of gene expression (green dots) were found only in area in or adjacent to cells lining the lung airway in FIG. 10B. The area between the two white dashed lines in FIGS. 10A-10D indicate the predicted location for Scgb1a1 mRNA expression (i.e., the lining of the lung airway) in each of the image panes in FIGS. 10A-10D). Each image pane in FIGS. 10A-10D includes two sets of two white dashed lines, each indicating the lining of a lung airway.

As shown in FIG. 11 and FIGS. 12A-C, the methods provided herein can be used to measure mRNA transcript mislocalization. Padlock probes were designed to hybridize to extended capture probes following capture of Scgb1a1 mRNA transcripts on the array. Following padlock probe hybridization and circularization, RCA was used to amplify the circularized padlock probe. Fluorescent probes having a sequence at least substantially complementary to a portion of the amplified circularized padlock probe were added to the sample to detect the RCA product. The RCA product serves as a proxy for the location of Scgb1a1 mRNA molecules and thus any mislocalization of the Scgb1a1 mRNA molecules from their original position in the biological sample.

Figure 11:
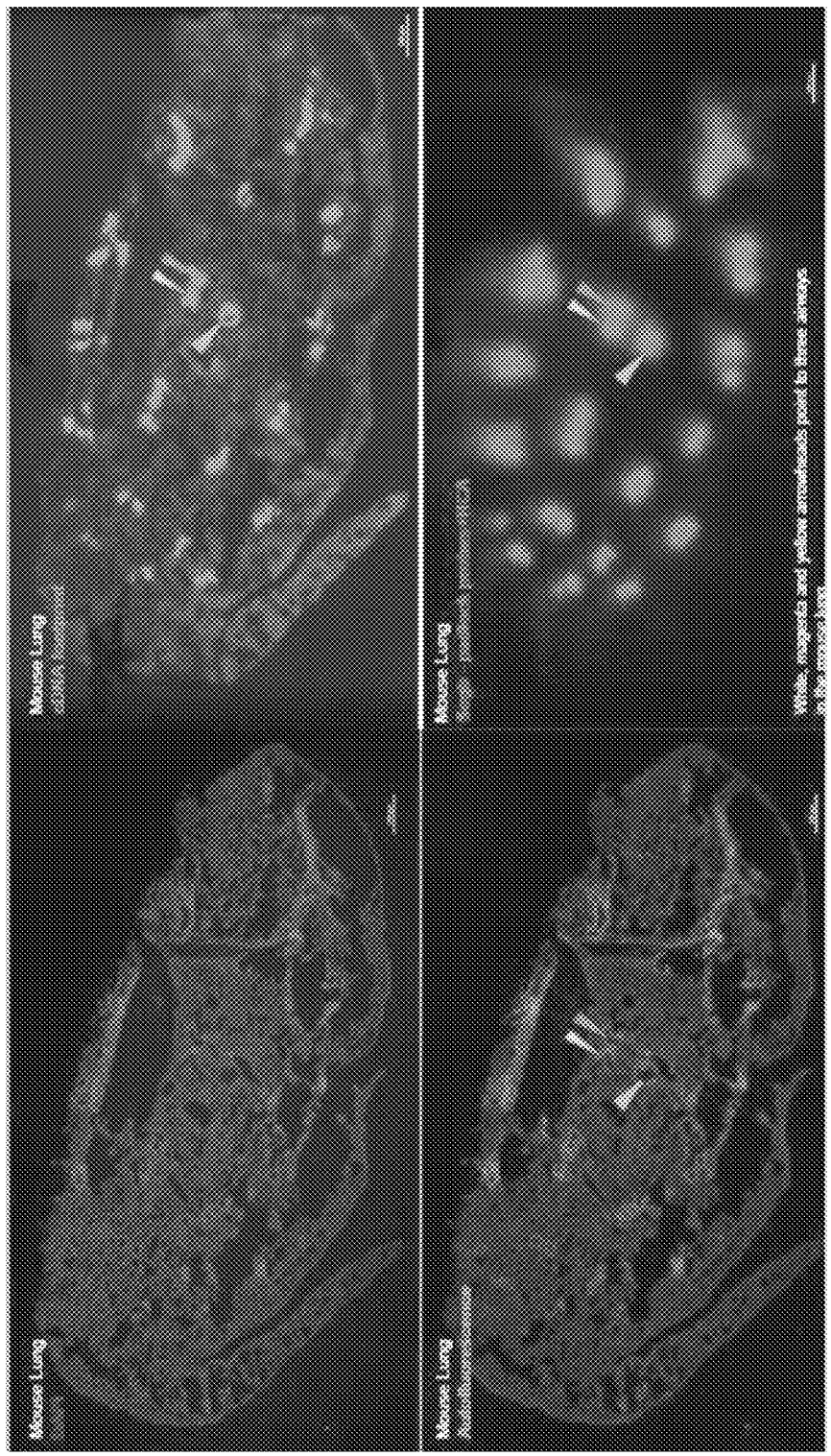
FIG. 11 shows fluorescent images of mouse lung: upper left-DAPI, lower left-auto fluorescence, upper right-cDNA footprint from spatial array analysis, and lower right-fluorescent probes hybridized to the product of an RCA reaction. Arrows indicate three exemplary lung tissue airways.
Figures 12A, 12B, 12C:
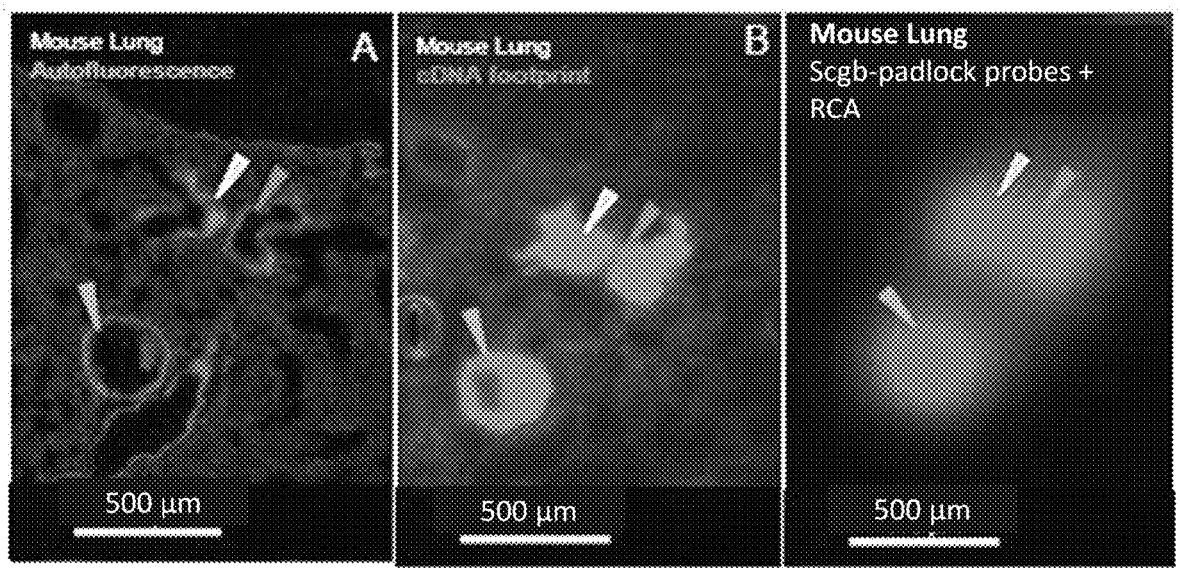
FIGS. 12A-12E shows immunofluorescence images of mouse lung.
Figures 12D, 12E:
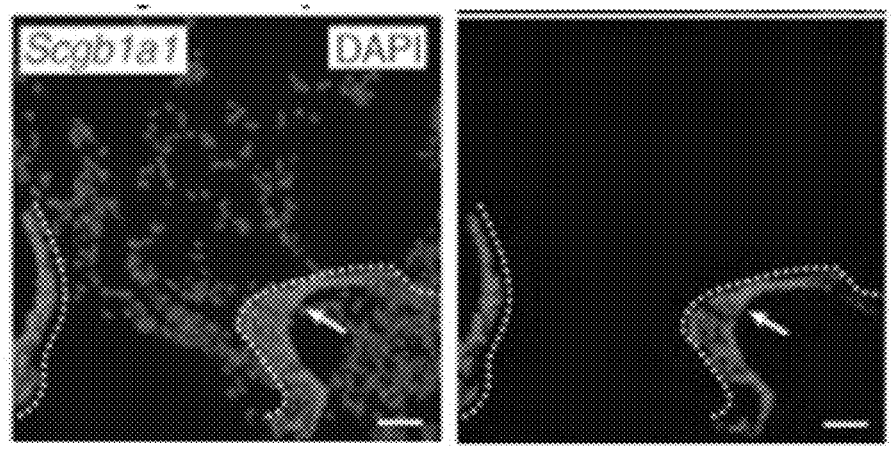

FIG. 11 shows the signal from the fluorescent probes hybridized to the RCA product (bottom right panel) as compared to nuclear staining of the biological sample (DAPI, upper left panel), auto fluorescence of the biological sample (bottom left panel), and a fluorescent cDNA footprint (e.g., incorporation of one or more fluorescent nucleotides into extended capture probes that hybridize to mRNAs) (upper right panel). The arrows point to three different airways in the mouse lung. FIGS. 12A-12C show magnified images of the three lung airways highlighted in FIG. 11. FIG. 12D and FIG. 12E show single molecule Fluorescent In Situ Hybridization (smFISH) images for Scgb1a1 mRNA molecules confirming that the Scgb1a1 mRNA molecules were detected only in the cells lining the airway. The data from FIGS. 12A-12C was then used to calculate the mislocalization of the Scgb1a1 mRNA molecules following different permeabilization conditions.

In a second experiment, mislocalization of Prox1, which encodes for Prospero homeobox protein 1 (PROX1), was examined in fresh frozen mouse brain sections. 10 µm sections were placed on tissue optimization slides (Visium Tissue Optimization Slides, 10× Genomics, Pleasanton, CA). The fresh frozen mouse brain samples were fixed in methanol for 20 minutes at −20° C. The mouse brain samples were stained with DAPI for nuclear detection (or alternately with H&E) and imaged. The sample was treated with a permeabilization buffer comprising pepsin or proteinase K to allow migration of analytes from the mouse brain sample to the tissue optimization slides. mRNA was captured on the capture probes of the tissue optimization slide, and a reverse transcription reaction was performed to convert the captured mRNA into cDNA. After, the tissue optimization slide was treated with 0.8M KOH to denature and remove the mRNA from the capture probes.

Figures 13A, 13B:
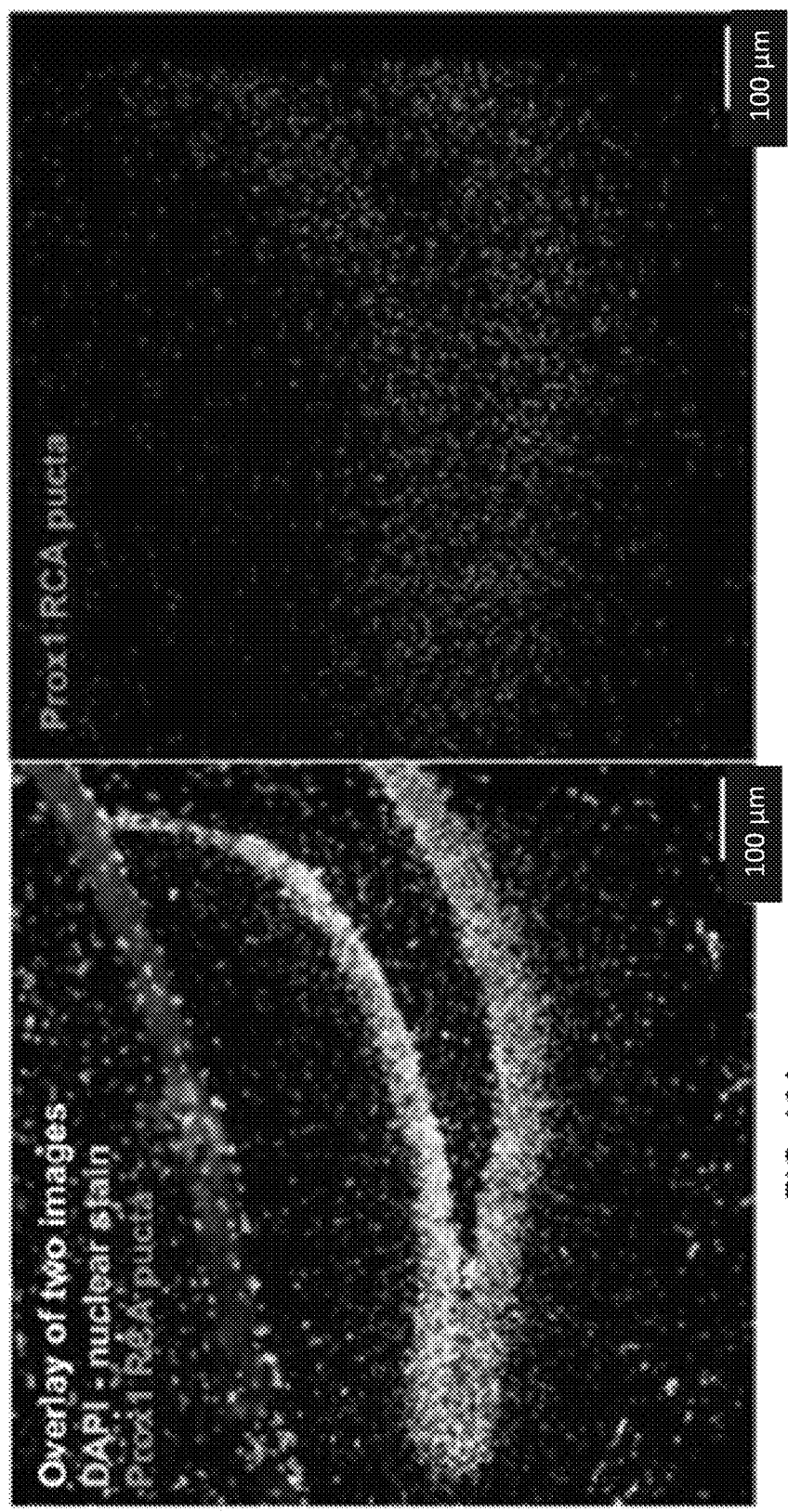
FIGS. 13A-13B show representative images of (FIG. 13A) DAPI (i.e., nuclear) staining and Prox1 mRNA expression after RCA reaction and (FIG. 13B) Prox1 mRNA expression after RCA reaction alone in fresh frozen mouse brain samples.

Snail probes for Prox1 cDNA were hybridized to the generated cDNA molecules affixed to the tissue optimization slide, followed by ligation, rolling circle amplification, and detection of the RCA product using fluorescently-tagged probes hybridized to the RCA product. The results are shown in FIG. 13A (overlay of DAPI and Prox1 using RCA) and FIG. 13B (Prox1 using RCA only). Using RCA, detection of Prox1 was seen outside areas of DAPI stain, demonstrating in this example, the Prox1 mRNA transcripts had mislocalized during mRNA capture on the tissue optimization slide. Using location and intensity of the RCA product signal, one can determine (e.g., calculate) an average mislocalization distance of Prox1 after RCA.

The data in the above experiments show that methods described herein can be used to measure mislocalization of analytes, including mRNA transcripts. In particular, these data show that the methods described herein can be used to determine analyte mislocalization as various experimental parameters are altered (e.g., permeabilization time (e.g., 0-30 minutes), permeabilization concentration, permeabilization temperature (e.g., room temperature; 37° C.).

Figure 14:
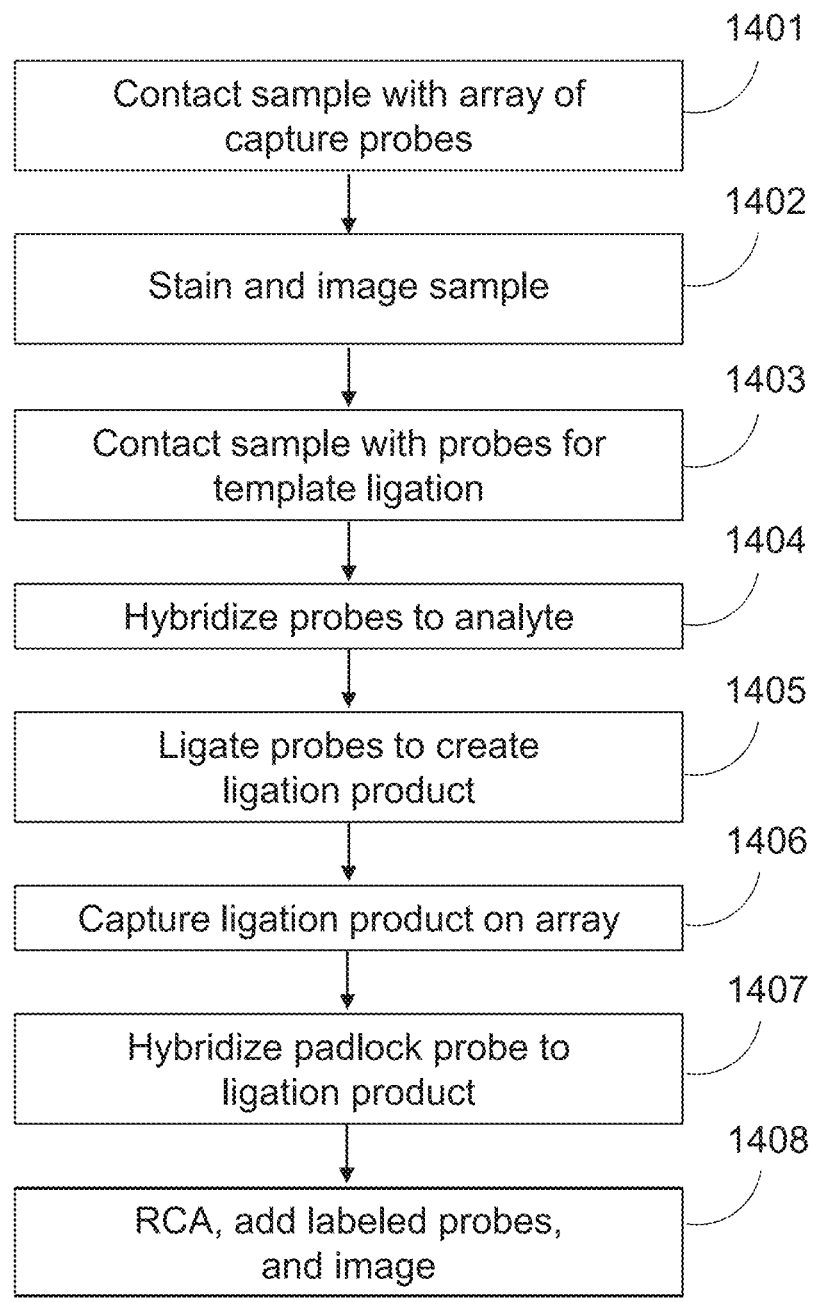
FIG. 14 shows an exemplary templated ligation and RCA workflow.

Example 2—Method for Determining the Mislocalization of an Analyte Using Templated Ligation This example provides a method of identifying the mislocalization of an analyte (e.g., an mRNA molecule) in a biological sample (e.g., a tissue section) using a templated ligation product as a proxy for detection of the analyte. Here, a padlock probe or snail probe hybridizes directly to the ligation product after the ligation product hybridizes to a capture domain of a capture probe on an array (e.g., tissue optimization slide). Briefly, as shown in FIG. 14, the methods include 1401 contacting a biological sample with array of capture probes. The sample is stained (e.g., using H&E, immunofluorescence, or immunohistochemistry), and imaged 1402. Samples are destained (e.g., using HCl) and decrosslinked. Following decrosslinking, samples are treated with pre-hybridization buffer (e.g., hybridization buffer without the first and second probes). Then, the biological sample 1403 is contacted with a first probe and a second probe, wherein the first probe and the second probe each include one or more sequences that are substantially complementary to sequences of the analyte, and wherein the second probe includes a capture probe capture domain. The first probe and the second probe 1404 hybridize to complementary sequences in the analyte. After hybridization, a ligation product comprising the first probe and the second probe 1405 is generated, and the ligation product is released from the biological sample (e.g., using RNAse H). The biological sample is permeabilized and the liberated ligation product is then available 1406 to hybridize to the capture domain of a probe on the array (e.g., Visium Tissue Optimization or Visium Gene Expression slide). A padlock probe (e.g., 800 in FIG. 8A) or snail probe hybridize 1407 directly to the captured ligation product. Optionally, a snail probe is tethered to the capture probe. The padlock probe or snail probe is ligated to create a circularized padlock probe or snail probe and amplified using RCA.

Figure 15:
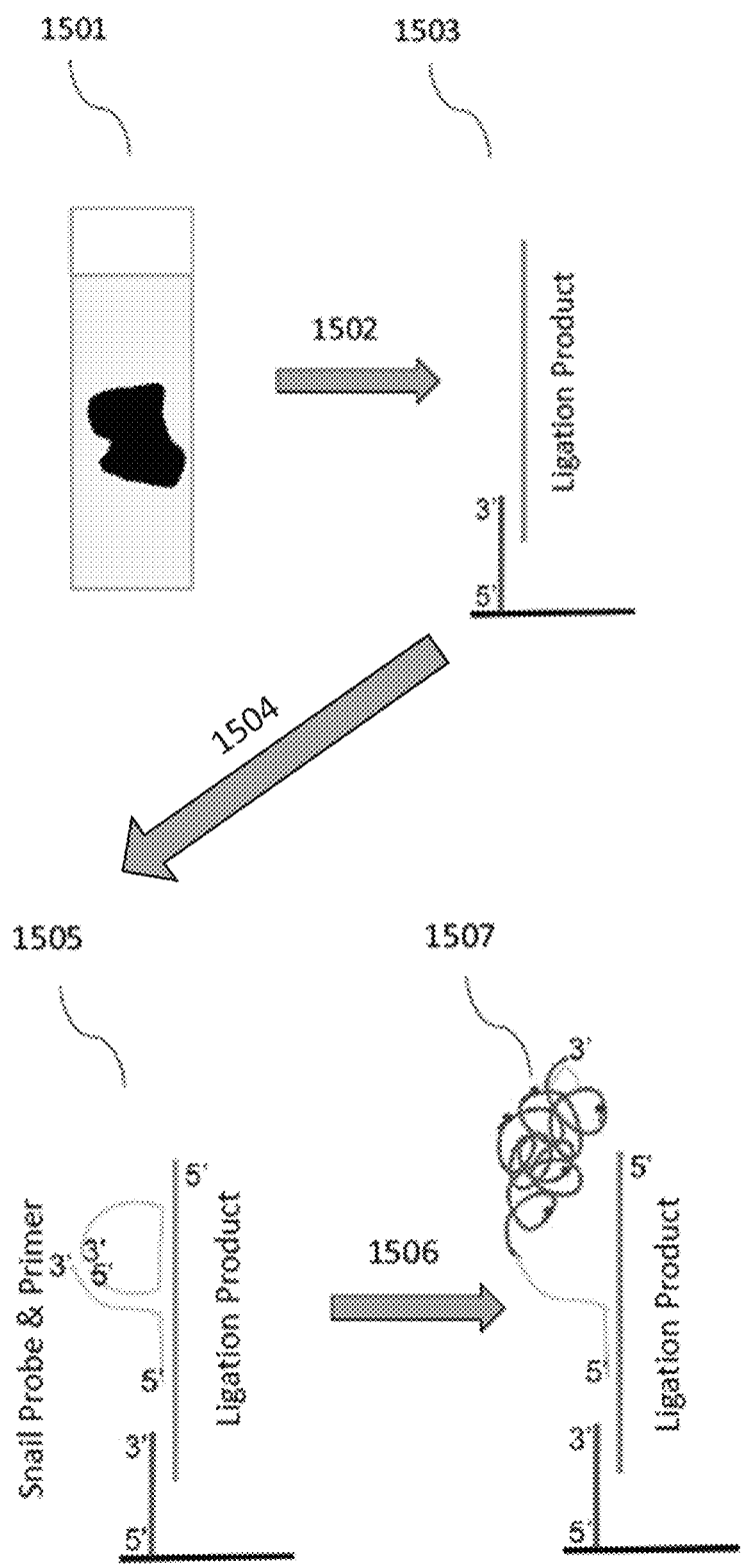
FIG. 15 shows a schematic of the methods of templated ligation and RCA using a snail probe.

The method described here is depicted in FIG. 15. In 1501, a biological sample (e.g., a tissue section) is placed on a slide comprising capture probes (e.g., Visium Tissue Optimization or Visium Gene Expression slide), stained and imaged. After imaging, template ligation probes are added to the biological sample, where the probes hybridize to a target and are ligated 1502. After permeabilization of the biological sample, the ligation product is captured 1503 on the slide (e.g., hybridized to the capture domain of a capture probe). A snail probe and primer is added 1504 to the array, where the snail probe hybridizes 1505 to the captured ligation product. After padlock probe or snail probe ligation, rolling circle amplification 1506 is performed, and labeled probes are added 1507 to hybridize to the RCA product.

Then, the sample is imaged for a second time 1408. One can measure the distance of an analyte imaged in 1402 to the distance of the analyte imaged in 1408 (e.g., via overlay of the images) to determine mislocalization of the analyte.

Example 3—Method for Determining the Mislocalization of a Protein Analyte

This example provides a method of identifying the mislocalization of an analyte (e.g., a protein molecule) in a biological sample (e.g., a tissue section) after (1) binding of an analyte capture agent to a protein and (2) capture of an oligonucleotide of the analyte capture agent by a capture probe on an array.

Briefly, a formalin-fixed, paraffin-embedded tissue sample is sectioned and mounted on an array slide (e.g., Visium Gene Expression Slides, 10× Genomics, CA) comprising capture probes, and is deparaffinized using a series of xylene and ethanol washes prior to drying at room temperature. Next, the array slides are heated, followed by a series of ethanol washes (e.g., 100%, 96%, 96%, and 70% ethanol). The tissue section is H&E stained and brightfield imaged. Alternatively, tissues can be stained (e.g., immunofluorescence stained) instead of H&E staining.

After staining, the tissue section is washed and decrosslinked. After decrosslinking, analyte capture agents are added to the tissue section to allow the analyte capture agents to bind to protein targets in the tissue section. After washing to remove unbound analyte capture agents, the tissue section is permeabilized and the oligonucleotide of the analyte capture agent hybridizes to a capture domain of the capture probes on the array. Optionally, the analyte binding agent oligonucleotides are extended to create an extended capture probe. Then, a padlock probe (e.g., 800 in FIG. 8A) or snail probe is hybridized either directly to oligonucleotide of the analyte capture agent or to the extended capture probe. A second snail probe is tethered to the extended capture probe. The padlock probe or snail probe is ligated to create a circularized padlock probe or snail probe and amplified using RCA. Then, the amplified circularized padlock probe or snail probe is contacted with a plurality of detection probes. The sample (e.g., a tissue section) is imaged for a second time (e.g., brightfield imaging to detect H&E stain; fluorescent stain for a protein marker). For example, an analyte can be associated with a stain (e.g., H&E; immunofluorescence), allowing a user to identify where the analyte is located in the biological sample. The second image can be compared to the first image generated prior to addition of the analyte capture agents. By comparing the two images, one can measure mislocalization of the protein analyte using the analyte capture agent.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining mislocalization of a nucleic acid within a tissue sample, the method comprising:
   (a) obtaining a first image of the tissue sample, wherein the tissue sample is stained with a biomarker that is specific for a second analyte having colocalized expression with the nucleic acid;
   (b) hybridizing the nucleic acid to a capture domain of a capture probe on an array, wherein the array comprises a plurality of capture probes, wherein the plurality of capture probes comprise a capture domain;

(c) extending the capture probe using the nucleic acid as a template, thereby generating an extended capture probe on the array;

(d) hybridizing a padlock probe or a snail probe to the extended capture probe on the array;

(e) circularizing the padlock probe or the snail probe on the array;

(f) amplifying the padlock probe or the snail probe on the array, thereby generating an amplified circularized padlock probe or an amplified circularized snail probe on the array;

(g) hybridizing a plurality of detection probes to the amplified circularized padlock probe or the amplified circularized snail probe on the array, wherein a detection probe from the plurality of detection probes comprises:
a nucleic acid sequence that is substantially complementary to a sequence of the padlock probe or the snail probe, and
a detectable label;

(h) obtaining a second image of the tissue sample and detecting a signal intensity from the plurality of detection probes in the second image; and (i) determining mislocalization of the nucleic acid within the tissue sample by comparing detection of the biomarker in the first image to the signal intensity of the detectable label in the second image.

2. The method of claim 1, wherein the padlock probe or the snail probe comprises:
(i) a first sequence that is substantially complementary to a first portion of the extended capture probe, or a complement thereof;
(ii) a backbone sequence; and
(iii) a second sequence that is substantially complementary to a second portion of the extended capture probe, or a complement thereof.

3. The method of claim 2, wherein the first sequence and the second sequence are substantially complementary to adjacent sequences of the extended capture probe, or a complement thereof.

4. The method of claim 2, wherein the first sequence and the second sequence are substantially complementary to sequences of the extended capture probe, or a complement thereof, that are about 2 to 50 nucleotides apart.

5. The method of claim 4, wherein the circularizing the padlock probe or the snail probe comprises filling in a gap between the first sequence and the second sequence using a polymerase.

6. The method of claim 2, wherein the backbone sequence comprises a backbone barcode sequence unique to the padlock probe or the snail probe.

7. The method of claim 1, wherein the circularizing the padlock probe or the snail probe comprises ligating the padlock probe or the snail probe.

8. The method of claim 7, wherein the ligating comprises enzymatic ligation or chemical ligation.

9. The method of claim 8, wherein the enzymatic ligation utilizes a T4 DNA ligase.

10. The method of claim 1, wherein the amplifying comprises rolling circle amplification.

11. The method of claim 10, wherein the amplifying comprises:
hybridizing one or more primers to the padlock probe or the snail probe; and
amplifying the padlock probe or the snail probe with a polymerase.

12. The method of claim 11, wherein the polymerase is a Phi29 DNA polymerase.

13. The method of claim 11, wherein the one or more primers are substantially complementary to a portion of the padlock probe or the snail probe.

14. The method of claim 1, wherein the detection probe is about 10 to about 60 nucleotides in length.

15. The method of claim 1, wherein the detectable label comprises a fluorophore.

16. The method of claim 2, wherein the detection probe is substantially complementary to (i) a portion of the first sequence; (ii) a portion of the second sequence; (iii) a portion of the backbone sequence; and/or (iv) a portion of the nucleic acid or a complement thereof.

17. The method of claim 1, wherein the tissue sample is permeabilized using a permeabilization agent prior to step (b).

18. The method of claim 17, wherein the permeabilization agent comprises proteinase K or pepsin.

19. The method of claim 1, wherein the tissue sample comprises a formalin-fixed paraffin embedded sample.

20. The method of claim 1, wherein the tissue sample comprises a fresh frozen sample.

21. The method of claim 1, wherein the tissue sample comprises a tissue section.

22. The method of claim 1, further comprising varying thickness of the tissue sample to determine an optimal tissue thickness to minimize nucleic acid mislocalization in the tissue sample.

23. The method of claim 1, wherein the tissue sample is stained prior to obtaining the first image of the tissue sample.

24. The method of claim 23, wherein the tissue sample is stained in (a) using 4',6-diamidino-2-phenylindole (DAPI), immunofluorescence, immunohistochemistry, hematoxylin, or eosin.

25. The method of claim 1, further comprising varying permeabilization time to determine an optimal permeabilization time for minimizing nucleic acid mislocalization in the tissue sample.

26. The method of claim 1, further comprising varying permeabilization temperature to determine an optimal permeabilization temperature for minimizing nucleic acid mislocalization in the tissue sample.

27. The method of claim 1, wherein determining the mislocalization of the nucleic acid comprises measuring signal intensity from the plurality of detection probes in the second image and comparing the signal intensity to detection of the biomarker in the first image of the tissue sample.

28. The method of claim 1, wherein the capture domain of the capture probe comprises a poly(T) sequence.

29. The method of claim 1, wherein the nucleic acid is mRNA.

30. The method of claim 1, wherein the nucleic acid is an mRNA molecule and the second analyte is a protein translated from the nucleic acid.

* * * * *